United States Patent
Sancilio

(10) Patent No.: US 12,157,743 B2
(45) Date of Patent: Dec. 3, 2024

(54) SOLID FORMS OF ALPHA-1062 GLUCONATE

(71) Applicant: Alpha Cognition Inc., Vancouver (CA)

(72) Inventor: Fred D. Sancilio, Stuart, FL (US)

(73) Assignee: Alpha Cognition Inc., Vancouver (CA)

( * ) Notice: Subject to any disclaimer, the term of this patent is extended or adjusted under 35 U.S.C. 154(b) by 0 days.

(21) Appl. No.: 18/463,157

(22) Filed: Sep. 7, 2023

(65) Prior Publication Data

US 2023/0416267 A1    Dec. 28, 2023

Related U.S. Application Data

(63) Continuation of application No. 17/575,025, filed on Jan. 13, 2022, now Pat. No. 11,795,176.

(30) Foreign Application Priority Data

Jan. 13, 2021 (EP) .................... 21151412
Jan. 19, 2021 (EP) .................... 21152317

(51) Int. Cl.
*C07D 491/06* (2006.01)
*A61J 1/03* (2023.01)

(52) U.S. Cl.
CPC ............ *C07D 491/06* (2013.01); *A61J 1/035* (2013.01); *C07B 2200/13* (2013.01)

(58) Field of Classification Search
CPC ............ C07D 491/06; C07D 489/04; C07D 491/048; A61J 1/035; C07B 2200/13; Y02A 50/30; A61K 31/55; A61P 25/00; A61P 25/16; A61P 25/28
See application file for complete search history.

(56) References Cited

U.S. PATENT DOCUMENTS

| 6,316,439 B1 | 11/2001 | Kosley, Jr. et al. |
| 2005/0258065 A1 | 11/2005 | Stroppolo et al. |

FOREIGN PATENT DOCUMENTS

| WO | WO 2014/016430 A1 | 1/2014 |

OTHER PUBLICATIONS

Extended European Search Report in EP21152317.0 issued Apr. 1, 2021.
Caira, Mino R. "Crystalline polymorphism of organic compounds." Topics in Current Chemistry; *Design of Organic Solids* (1998): 163-208.
International Search Report and Written Opinion in PCT/CA2022/050046 issued Apr. 14, 2022.
Maelicke, Alfred, et al., "Memogain is a Galantamine Pro-drug having Dramatically Reduced Adverse Effects and Enhanced Efficacy", J Mol Neurosci (2010) 40:135-137.

*Primary Examiner* — Susanna Moore
*Assistant Examiner* — Luisalberto Gonzalez
(74) *Attorney, Agent, or Firm* — Knobbe, Martens, Olson & Bear, LLP

(57) ABSTRACT

The invention relates to crystalline forms of Alpha-1062 gluconate. In one aspect, the invention relates to a crystalline solid form of Alpha-1062 gluconate (Form C), wherein said crystalline form has prominent peaks at 3.90, 9.74, 10.35 and 21.43 degrees 2-theta (±0.2) in a powder X-ray diffraction pattern. The invention further relates to methods for treating a brain disease associated with cognitive impairment and/or with a cholinergic deficit in a subject, including administering the crystalline forms of Alpha-1062 gluconate to a subject in need thereof.

13 Claims, 30 Drawing Sheets

Top to bottom:
    Lot CA19-1444, Form A
    Lot QCL-PLC-I-96, Mixture of Forms A, B, & D
    Lot CA19-0673, Form A Top to bottom:
 Lot QCL-PLC-I-96, Mixture of Forms A, B, & D
 Form A, Lot CA19-1144
 Form B, 8235-85-01
 Form D, 8235-86-01

Top to bottom:
    Lot QCL-PLC-I-96, Mixture of Forms A, B, & D
    Form A, Lot CA19-1144
    Form B, 8235-85-01
    Form D, 8235-86-01

Top to bottom:
    Form A: Alpha-1062 Gluconate, Lot CA19-1144
    Form B: Alpha-1062 Gluconate, 8235-85-01
    Form C: Alpha-1062 Gluconate, 8235-87-02
    Form D: Alpha-1062 Gluconate, 8235-86-01
    Material E: 8235-76-04
    Material F: 8235-76-07
    Material G: Alpha-1062 Gluconate, 8235-100-02

| Target RH (%) | Sample RH (%) | Sorp Mass Change (%) | Sample RH (%) | Desorp Mass Change (%) | Hysteresis |
|---|---|---|---|---|---|
| 5.0 | 5.2 | 0.00 | 5.4 | 7.49 | |
| 15.0 | 15.6 | 0.02 | 16.3 | 8.50 | 8.48 |
| 25.0 | 25.1 | 0.04 | 25.8 | 8.64 | 8.60 |
| 35.0 | 34.7 | 0.06 | 35.6 | 8.77 | 8.71 |
| 45.0 | 44.9 | 0.10 | 45.8 | 8.92 | 8.82 |
| 55.0 | 54.6 | 0.17 | 55.6 | 9.12 | 8.96 |
| 65.0 | 64.6 | 0.26 | 65.6 | 9.38 | 9.12 |
| 75.0 | 74.4 | 0.57 | 75.4 | 9.78 | 9.21 |
| 85.0 | 84.8 | 3.53 | 85.7 | 10.47 | 6.94 |
| 95.0 | 96.0 | 12.20 | 96.0 | 12.20 | |

|  | Memogain Gluconate |
| --- | --- |
| Bravais Type | Primitive Orthorhombic |
| a [Å] | 6.906 |
| b [Å] | 8.726 |
| c [Å] | 51.202 |
| α [deg] | 90 |
| β [deg] | 90 |
| γ [deg] | 90 |
| Volume [Å³/cell] | 3,085.5 |
| Chiral Contents? | Chiral |
| Extinction Symbol | P $2_1$ $2_1$ $2_1$ |
| Space Group(s) | P$2_1 2_1 2_1$ (19) |
| Source | Manual Input |

| Target RH (%) | Sample RH (%) | Sorp Mass Change (%) | Sample RH (%) | Desorp Mass Change (%) | Hysteresis |
|---|---|---|---|---|---|
| 5.0 | | | 5.5 | -7.035 | |
| 15.0 | | | 16.2 | -0.254 | |
| 25.0 | | | 25.6 | -0.180 | |
| 35.0 | | | 35.4 | -0.123 | |
| 45.0 | | | 45.5 | -0.043 | |
| 50.0 | 49.6 | 0.002 | | | |
| 55.0 | 54.6 | 0.042 | 55.3 | 0.057 | 0.014 |
| 65.0 | 64.5 | 0.173 | 65.3 | 0.182 | 0.010 |
| 75.0 | 74.2 | 0.363 | 75.1 | 0.372 | 0.009 |
| 85.0 | 84.1 | 0.679 | 85.2 | 0.692 | 0.013 |
| 95.0 | 95.4 | 1.545 | 95.4 | 1.545 | |

| | Memogain Gluconate |
|---|---|
| Bravais Type | Primitive Monoclinic |
| a [Å] | 9.077 |
| b [Å] | 6.930 |
| c [Å] | 22.460 |
| α [deg] | 90 |
| β [deg] | 92.46 |
| γ [deg] | 90 |
| Volume [Å³/cell] | 1,411.5 |
| Chiral Contents? | Chiral |
| Extinction Symbol | P 1 2$_1$ 1 |
| Space Group(s) | P2$_1$ (4) |
| Source | Triads® Algorithm |

| Target RH (%) | Sample RH (%) | Sorp Mass Change (%) | Sample RH (%) | Desorp Mass Change (%) | Hysteresis |
|---|---|---|---|---|---|
| 5.0 | 5.1 | 0.000 | 6.6 | 2.803 | |
| 15.0 | 15.5 | -0.004 | 16.5 | 2.835 | 2.839 |
| 25.0 | 24.9 | -0.012 | 25.9 | 2.869 | 2.881 |
| 35.0 | 34.5 | -0.017 | 35.8 | 2.907 | 2.924 |
| 45.0 | 44.8 | -0.018 | 45.9 | 2.950 | 2.968 |
| 55.0 | 54.5 | -0.015 | 55.7 | 3.003 | 3.017 |
| 65.0 | 64.3 | 0.001 | 65.6 | 3.070 | 3.069 |
| 75.0 | 74.0 | 0.048 | 75.2 | 3.234 | 3.186 |
| 85.0 | 84.4 | 0.322 | 85.4 | 3.691 | 3.369 |
| 95.0 | 95.8 | 4.692 | 95.8 | 4.692 | |

Top to bottom:
 Generated from a melt quench of Form A
 Reanalysis of material after 5 weeks

SOLID FORMS OF ALPHA-1062 GLUCONATE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The invention relates to the field of solid forms of pharmaceutical agents and methods of preparation thereof. The invention relates to crystalline forms of Alpha-1062 gluconate. In one aspect, the invention relates to a crystalline solid form of Alpha-1062 gluconate (Form A), wherein said crystalline form has prominent peaks at 3.61, 10.98, 14.41 and 18.44 degrees 2-theta (±0.2) in a powder X-ray diffraction pattern. The invention further relates to methods for manufacturing crystalline forms and compositions comprising said crystalline forms.

Description of the Related Art

Alzheimer's disease (AD) is the most common form of dementia in the elderly. It is characterized by progressive memory loss, with impairment of attentiveness, semantic memory, abstract thinking and other cognitive functions. Several experimental therapies having potential of disease modification are currently undergoing investigation, with the most prominent involving antibodies targeting abnormal accumulation of proteins such as extracellular beta amyloid oligomers and plaques, and intracellular tau protein. However, recent phase III clinical studies of antibody therapies targeting beta-amyloid have failed to show sufficient therapeutic efficacy.

Another early marker of AD is the increasing loss of cholinergic neurons and reduced density of nicotinic acetylcholine receptors (nAChRs) in the course of the disease. Cholinergic enhancement is therefore considered a symptomatic therapy to improve cognitive function through enhancement of cholinergic transmission. Drugs licensed for this purpose are tacrine, donepezil, rivastigmine and galantamine, namely inhibitors of the enzyme acetylcholinesterase (AChE) and to a varying extent, butyryl cholinesterase (BuChE), which normally metabolize and thereby inactivate the cholinergic transmitter, acetylcholine (ACh). The enhancement of cholinergic function in the brain resulting from the action of these drugs enhances cognition and improves various behavioral aspects in AD.

Galantamine is a tertiary amide, which occurs naturally in some bulb plants. In addition to inhibition of AChE, galantamine also enhances cholinergic activity by non-competitive, allosteric modulation of the nAChR. It was introduced as a drug for AD in 2000 and now is approved in more than 70 countries. The indication is generally 'mild to moderate dementia of the Alzheimer's type'. It is currently marketed as Razadyne® in the USA, and as Reminyl® elsewhere.

In contrast to rivastigmine and donepezil, galantamine however does not significantly enrich in the human brain in comparison to blood plasma. This is because galantamine, a plant alkaloid, is much less lipophilic than the other two cholinesterase inhibitors used as drugs in AD and hence exhibits in steady-state only a rather low brain-to-blood concentration ratio (BBCR<2). Similar to other cholinesterase inhibitors, galantamine has a clinically significant level of gastro-intestinal (GI) side effects, including nausea, vomiting and diarrhoea. To accommodate patients, cholinesterase inhibitors are often initially administered at a low (non-efficacious) dose, and then adjusted to what the patients experience as an acceptable level of GI side effects, making it likely that most, if not all, patients never achieve treatment with the most therapeutically effective levels.

To enhance the lipophilicity of acetylcholinesterase inhibitors, such as galantamine, and improve their passage through the blood-brain barrier, hydrophobic side chains have been appended to the basic alkaloid structures, as described in EP1940817, WO2009/127218 and US 2009/0253654.

The galantamine pro-drug Alpha-1062 (also known as GLN-1062 or Memogain®) was therefore developed as a benzoic ester of galantamine, to enhance the hydrophobicity of galantamine. Alpha-1062 exhibits essentially no pharmacological activity until it is cleaved by a carboxyesterase, resulting in the release of galantamine. There is substantial evidence from animal studies that intravenous, intranasal, buccal or sublingual administration of Alpha-1062 rapidly achieves higher brain concentrations of Alpha-1062 and galantamine than intravenous or oral administration of galantamine, and with a proportionally higher brain:blood concentration ratio. Alpha-1062 enhances delivery of galantamine to the brain, reduces GI side effects and therefore offers advantages over other drugs currently available for AD.

WO2014/016430 discloses transmucosal administration of Alpha-1062 (Alpha-1062) via intranasal, buccal or sublingual modes, in addition to various formulations and salts of Alpha-1062, including for example lactate, gluconate, maleate and saccharate salts. WO2014/016430 also teaches two methods of producing a gluconic acid salt of Alpha-1062 and provides powder X-ray diffraction patterns for the solid forms obtained from these methods.

The Alpha-1062 gluconate salts described in WO2014/016430 show solubility in water above 10% weight per volume (w/v). Despite showing good solubility, these gluconate salts are metastable in solution and the fully dissolved homogenous solutions are only recovered by warming the aqueous mixtures to e.g. >50° C. until precipitations disappear. Precautions must therefore be taken to reduce or avoid precipitation seeding in such formulations.

Despite the solid forms and formulations of Alpha-1062 known in the art, further developments are required for improved or more efficient means of preparing and/or formulating Alpha-1062 to provide soluble and/or stable forms for formulation and medical administration.

SUMMARY OF THE INVENTION

In light of the prior art the technical problem underlying the invention was the provision of improved or alternative means for providing soluble and/or stable forms of Alpha-1062.

This problem is solved by the features of the independent claims. Preferred embodiments of the present invention are provided by the dependent claims.

In one aspect, the invention therefore relates to a crystalline solid form of Alpha-1062 gluconate (referred to as Form A).

Alpha-1062 gluconate (FIG. 1) is under development and use as a pharmaceutical drug substance. Many organic drug substances can exist in a solid state as polymorphs, pseudo-polymorphs (hydrates/solvates), or amorphous forms, each with differing physiochemical properties. These physiochemical properties of the drug substance affect the solubility, dissolution, stability, and bioavailability of the drug substance and are crucial to the development and performance of a drug product. Thus, polymorphic studies were undertaken on three lots of Alpha-1062 gluconate (Table 1) to investigate and identify its stable solid forms (polymorphs) and determine the relative relationship and interconversion with other purported hydrates/solvates (pseudopolymorphs).

From the wide variety of analytical techniques available for characterization of materials several are the most definitive for the determination and elucidation of polymorphic materials. These methods include X-Ray Diffraction (Single Crystal and Powder Diffraction [XRPD]); Thermal Analysis (Thermogravimetric Analysis [TGA] and Differential Scanning calorimetry [DSC]); and Vibrational Spectroscopy (Infrared [FTIR], Near-Infrared [FT-NIR], and Raman).

The preferred technique for determination of polymorphism is X-Ray Diffraction. The identification and release of the crystalline Forms of Alpha-1062 gluconate can therefore be enabled using the 2-theta positions of the prominent peaks found in the transmission mode XRPD patterns.

During these polymorphic studies utilizing a variety of solvents and crystallization conditions (Table 5), and subsequent XRPD analyses, seven unique crystalline materials were observed and isolated and are designated as Forms A, B, C, D and Materials E, F and G (FIG. 6). Amorphous material has also been observed.

Detailed representations are provided below for each of the identified solid forms (for example in Table 8 an overlay of prominent peaks is shown for Forms A-D).

Water activity ($a_w$) slurries (Table 6) along with relative humidity stressing (Table 7) were used to define the regions of stability for the hydrates of Alpha-1062 gluconate. The data indicates that at low water activities of less than 0.12 $a_w$, the most stable form is the Anhydrous Form A. As water activity increases to about 0.5 $a_w$, the most stable form is the Monohydrate Form C. At water activities above about 0.5 $a_w$, the most stable form is the Tetrahydrate Form B. Form D does not appear stable at any of the conditions evaluated and readily converts to the other dependent Forms dependent upon the storage humidity.

A summary of the identified forms is provided below:

Form A is an anhydrous crystalline material with concomitant melt/decomposition onset near 117° C. Form A appears kinetically stable in the solid state at 43% RH (RT) and was sustained up to 5 days at that condition.

Form B forms a tetrahydrate crystalline lattice. At least one of the lattice water sites is labile and is not fully hydrated, usually present at about 3.6 to 3.9 water molecules.

Form C forms a monohydrate crystalline lattice. The lattice water site is labile and is not fully hydrated, usually present at about 0.4 to 0.5 water molecules.

Form D forms a dihydrate crystalline lattice that is not thermodynamically stable and readily converts to other more stable hydrates, relative to the storage RH condition.

Materials E and F appear to be unidentified decomposition products and are generated when dichloromethane is used as a crystallization solvent.

Material G is an unknown but suspected metastable hydrate. Material G can be isolated by evaporation from either THF or 1,4-dioxane. Partial conversion to Form B was observed upon storage.

Based upon the data found during these studies, anhydrous Form A, stored under appropriate temperature and humidity conditions to maintain its Form and stability, appears best suited as the drug substance to be used in formulation and manufacture of drug products. The present invention therefore discloses multiple novel solid forms of Alpha-1062 gluconate salts. The present invention is therefore, in some embodiments, based on the discovery of hydrate forms of Alpha-1062 gluconate, which are, in some embodiments, to be avoided due to relatively lower solubility in water compared to the anhydrous Form A. The present invention, in some embodiments, relates to the unexpected finding of multiple solid forms of Alpha-1062 gluconate, each with distinct properties, and the identification of Form A, which appears best suited for pharmaceutical development.

Form A:

In one aspect, the invention relates to a crystalline solid form of Alpha-1062 gluconate (Form A), wherein said crystalline form has prominent peaks at 3.61, 10.98, 14.41 and 18.44 degrees 2-theta (±0.2) in a powder X-ray diffraction pattern.

These 4 peaks are selected from the prominent peak list provided below and appear to exhibit no substantial overlap with prominent peaks in the XRPD patterns for Forms B-D, or Materials E-G. In one embodiment, Form A can therefore be reliably distinguished using one or more prominent peaks, for example as mentioned above or as in FIG. 8 or Table 8, upon comparison of the corresponding powder X-ray diffraction patterns. In one embodiment, the presence of these peaks in a powder X-ray diffraction pattern may be used to identify Form A and/or distinguish Form A from the solid forms described previously in the art, for example those described in WO2014/016430.

In one embodiment, Form A has one or more additional prominent peaks at 15.20, 17.31, 17.79, 22.77, 23.64, 24.88 and 34.31 degrees 2-theta (±0.2) in a powder X-ray diffraction pattern. As outlined below, these peaks are selected from the prominent peak list and appear to exhibit no substantial overlap with prominent peaks in the XRPD patterns for Forms B-D, or Materials E-G.

In one embodiment, Form A has at least five prominent peaks selected from the list consisting of 3.61, 10.98, 13.80, 14.41, 14.56, 15.08, 15.20, 17.02, 17.31, 17.79, 18.44, 19.24, 20.18, 20.91, 21.22 and 22.40 degrees 2-theta (±0.2) in a powder X-ray diffraction pattern.

This peak list represents a list of prominent peaks from Table 8 for Form A. Typically, not all peaks from this list need be detected in order to determine the presence of Form A in any given preparation. According to the invention, for example in some embodiments, 1, 2, 3, 4, 5, 6, 7, 8, 9, 10 or more peaks, preferably those with relatively high signal intensity, may be employed to determine any given crystal form. For example, the 4, 5, 6, 7, 8, 9 or 10 most intense peaks may be employed to identify any given crystal form. In one embodiment, sufficient identification of any given crystal form, such as Form A, is achieved when the presence of at least four prominent peaks can be determined based on XRPD comparisons.

Typically, prominent XRPD peaks are the strongest low angle, non-overlapping peaks observed in a XRPD pattern. In some embodiments, the "prominent peaks" have preferably a ≥20% relative intensity, preferably ≥30% relative intensity, more preferably ≥40% relative intensity, in a powder X-ray diffraction pattern. The values of relative intensity may however vary depending on device or analysis mode and are not inherently limiting to the solid forms described herein.

In one embodiment, Form A has peaks at 7.25 and/or 12.67 degrees 2-theta (±0.2) in a powder X-ray diffraction pattern. These peaks are of relatively low intensity compared to the peaks outlined above as predominant peaks. However, peaks at 7.25 and/or 12.67 degrees 2-theta appear to be absent in all other patterns for Forms B-D or Materials E-G.

In one embodiment, the peaks are determined using powder X-ray diffraction analysis in transmission mode.

In one embodiment, Form A has at least three peaks selected from the list consisting of 10.98, 14.41, 17.31, 18.44 and 22.40 degrees 2-theta (±0.2) in a powder X-ray diffraction pattern. In one embodiment, said three peaks are within the five peaks with the highest relative intensity in a powder X-ray diffraction pattern obtained using analysis in transmission mode. In one embodiment, these five peaks are the most intense peaks in the XRPD pattern using transmission mode, as outlined in the examples below.

In one embodiment, the peaks are determined using powder X-ray diffraction analysis in reflectance mode.

In one embodiment, Form A has at least three peaks selected from the list consisting of 3.61, 7.25, 10.98, 14.56 and 22.40 degrees 2-theta (±0.2) in a powder X-ray diffraction pattern. In one embodiment, said three peaks are preferably within the five peaks with the highest relative intensity in a powder X-ray diffraction pattern obtained using analysis in reflectance mode. In one embodiment, these five peaks are the most intense peaks in the XRPD pattern using reflectance mode, as outlined in the example below.

In one embodiment, Form A has one or more peaks selected from the list consisting of 3.61, 7.25, 10.98, 14.56, 22.40 degrees 2-theta (±0.2) in a powder X-ray diffraction pattern. These peaks are also observable from the XRPD pattern using reflectance mode.

In one embodiment, Form A has one or more doublets selected from the list consisting of 14.41 and 14.56, 15.08 and 15.20, and 24.88 and 25.09 degrees 2-theta (±0.2) in a powder X-ray diffraction pattern. These doublets may be used to identify Form A, and optionally distinguish the Form from other forms.

Provided below is a Table of the typically observed XRPD pattern peaks for Form A collected in transmission mode.

Peak list Form A: Peak list determined from the powder X-ray diffraction pattern of Form A, according to FIG. 8. Accuracy of degrees 2-theta is provided at 2 decimal points, some variation dependent on batch or device may be evident.

| 2θ (°) | d (Å) | I (%) |
|---|---|---|
| 3.61* | 24.5 | 47 |
| 7.25 | 12.2 | 18 |
| 10.52 | 8.40 | 14 |
| 10.98* | 8.05 | 100 |
| 11.71 | 7.55 | 4 |
| 12.67 | 6.98 | 23 |
| 13.46 | 6.57 | 10 |
| 13.80* | 6.41 | 45 |
| 14.41* | 6.14 | 71 |
| 14.56* | 6.08 | 52 |
| 15.08* | 5.87 | 40 |
| 15.20* | 5.82 | 46 |
| 16.16 | 5.48 | 25 |
| 16.44 | 5.39 | 22 |
| 17.02* | 5.20 | 46 |
| 17.31* | 5.12 | 66 |
| 17.79* | 4.98 | 41 |
| 18.24 | 4.86 | 8 |
| 18.44* | 4.81 | 67 |
| 19.24* | 4.61 | 56 |
| 19.43 | 4.56 | 10 |
| 19.80 | 4.48 | 24 |
| 20.18* | 4.40 | 40 |
| 20.91* | 4.24 | 64 |
| 21.22* | 4.18 | 57 |
| 21.54 | 4.12 | 19 |
| 22.09 | 4.02 | 19 |
| 22.40* | 3.97 | 86 |
| 22.77* | 3.90 | 41 |
| 23.64* | 3.76 | 39 |
| 24.30 | 3.66 | 13 |
| 24.88* | 3.58 | 41 |
| 25.09* | 3.55 | 44 |
| 25.44 | 3.50 | 9 |
| 25.76 | 3.46 | 15 |
| 25.89 | 3.44 | 25 |
| 26.37 | 3.38 | 12 |
| 26.62 | 3.35 | 5 |
| 26.91 | 3.31 | 5 |
| 27.19 | 3.28 | 17 |
| 27.37 | 3.26 | 19 |
| 27.82 | 3.20 | 23 |
| 27.99 | 3.18 | 35 |
| 28.95 | 3.08 | 14 |
| 29.34 | 3.04 | 11 |
| 29.83 | 2.99 | 21 |
| 30.37 | 2.94 | 15 |
| 30.92 | 2.89 | 17 |
| 31.68 | 2.82 | 6 |
| 32.44 | 2.76 | 9 |
| 33.39 | 2.68 | 5 |
| 34.31 | 2.61 | 34 |

*Peaks may in some embodiments be considered as prominent peaks observed in the XRPD pattern.

In one embodiment, Form A exhibits an onset of melting at a temperature of 116-120° C., preferably at about 117° C., when assessed using differential scanning calorimetry (DSC).

In one embodiment, Form A exhibits a weight loss of <1%, preferably <0.5%, more preferably less than <0.3%, or <0.2%, prior to the onset of melt using DSC when assessed using Thermo-Gravimetric Analysis (TGA).

As is known to a skilled person, melting temperatures and weight loss of defined properties can be used to identify particular solid Forms. As described in detail below, DSC and TGA analyses were performed in order to determine defining characteristics of the solid forms described herein.

In one embodiment, Form A exhibits a solubility in water of above 100 mg/mL, preferably above 120 mg/mL, more preferably about 123 mg/mL. Methods for determining solubility in water are known to a skilled person and may be carried out without undue burden. Form A therefore exhibits unexpectedly good aqueous solubility.

In one embodiment, Form A is stable and shows no or negligible conversion to any one of Forms B-D or Materials E-G when stored at a relative humidity (RH) of less than 75%, preferably less than 50%, more preferably Form A is stable at an RH of about 43% or less.

As demonstrated in the examples below, Form A exhibits hygroscopicity above 75% RH. A 0.57% weight gain was observed from 5 to 75% RH. Weight significantly increased above 75% RH with 2.97% weight gained from 75 to 85% RH and an additional 8.7% weight gained from 85 to 95% RH. The data suggests that Form A converted to Form B when above 85% RH. Of note is that the material was held at 5% RH once the DVS experiment was completed and dehydrated back to Form A. Form A therefore has low hygroscopicity at RH values below 75%.

Form A represents an advantageous form of the Alpha-1062 gluconate salt. Due to its high stability when stored under low humidity (preferably at RH at about or less than 43% RH, or at low water activities of less than 0.12 $a_w$) and good solubility in water, it represents an ideal form for preparation of a pharmaceutical agent. Although Form A has improved solubility in water over Forms B-D, and is preferred, Forms B-D may in some embodiments also have good solubility in water and be suitable for formulation. The pseudopolymorph hydrate forms B-D tend to convert to Form A when stored at low humidity, thereby making the maintenance of the specific polymorph form, which is a very important part of preparation and formulation of pharmaceutical drugs, a reliable process, Form A thereby appears to be the optimal Form.

Form B:

In another aspect, the invention relates to a crystalline solid form of Alpha-1062 gluconate, designated Form B.

The invention therefore relates to a crystalline solid form of Alpha-1062 gluconate (Form B), wherein said crystalline form has prominent peaks at 10.69, 17.17, 21.00 and 24.67 degrees 2-theta (±0.2) in a powder X-ray diffraction pattern.

These 4 peaks are selected from the prominent peak list provided below and appear to exhibit no substantial overlap with prominent peaks in the XRPD patterns for Forms A, C or D or Materials E-G. In one embodiment, Form B can therefore be reliably distinguished using one or more prominent peaks, for example as mentioned above or as in FIG. 14 or Table 8, upon comparison of the corresponding powder X-ray diffraction patterns. In one embodiment, the presence of these peaks in a powder X-ray diffraction pattern may be used to distinguish Form B from the solid forms described previously in the art, for example those described in WO2014/016430.

In one embodiment, Form B has at least five prominent peaks selected from the list consisting of 10.69, 12.92, 13.26, 14.56, 16.45, 17.17 and 21.00 degrees 2-theta (±0.2) in a powder X-ray diffraction pattern. This peak list represents a list of prominent peaks from Table 8 for Form B.

In one embodiment, Form B has at least three prominent peaks selected from the list consisting of 10.69, 16.45, 17.17, 21.00 and 24.67 degrees 2-theta (±0.2) in a powder X-ray diffraction pattern. This peak list represents a list of the 5 most intense peaks from Table 8 for Form B.

Typically, not all peaks from this list need be detected in order to determine the presence of Form B in any given preparation. According to the invention, for example in some embodiments, 1, 2, 3, 4, 5, 6, 7, 8, 9, 10 or more peaks, preferably those with relatively high signal intensity, may be employed to determine any given crystal form. For example, the 4, 5, 6, 7, 8, 9 or 10 most intense peaks may be employed to identify any given crystal form. In one embodiment, sufficient identification of any given crystal form, such as Form B, is achieved when the presence of at least four prominent peaks can be determined based on XRPD In one embodiment, Form B has peaks at 12.92 and/or 15.46 degrees 2-theta (±0.2) in a powder X-ray diffraction pattern. These peaks are of relatively low intensity compared to the peaks outlined above as predominant peaks. However, peaks at 12.92 and/or degrees 2-theta appear to be absent in all other patterns for Forms A, C or D or Materials E-G.

In one embodiment, Form B exhibits an onset of melting at a temperature of 60-70° C., preferably at about 66° C., when assessed using differential scanning calorimetry (DSC). In one embodiment, Form B exhibits a second onset of melting at a temperature of 110-120° C., preferably at about 114° C., when assessed using differential scanning calorimetry (DSC). In one embodiment, Form B exhibits a third onset of melting at a temperature of 148-156° C., preferably at about 152° C., when assessed using differential scanning calorimetry (DSC).

In one embodiment, Form B exhibits a weight loss of 3-4%, more preferably about 3.3%, up to 114° C. when assessed using Thermo-Gravimetric Analysis (TGA). In one embodiment, Form B exhibits a weight loss of 5-6%, more preferably about 5.2%, up to 147° C. when assessed using Thermo-Gravimetric Analysis (TGA). In one embodiment, Form B has a good solubility in water and may be suitable for pharmaceutical formulation and administration.

Peak list Form B: Peak list determined from the transmission powder X-ray diffraction pattern of Form B, according to FIG. 14. Accuracy of degrees 2-theta is provided at 2 decimal points, some variation dependent on batch or device may be evident.

| 2θ (°) | d (Å) | I (%) |
|---|---|---|
| 3.43 | 25.7 | 7 |
| 6.88 | 12.8 | 4 |
| 10.27 | 8.61 | 5 |
| 10.69* | 8.27 | 100 |
| 11.37 | 7.78 | 5 |
| 12.92* | 6.85 | 20 |
| 13.26* | 6.67 | 21 |
| 13.82 | 6.40 | 6 |
| 14.56* | 6.08 | 22 |
| 15.46 | 5.73 | 12 |
| 16.45* | 5.38 | 42 |
| 16.72 | 5.30 | 9 |
| 17.17* | 5.16 | 38 |
| 17.77 | 4.99 | 17 |
| 18.52 | 4.79 | 8 |
| 18.89 | 4.69 | 3 |
| 19.40 | 4.57 | 16 |
| 20.39 | 4.35 | 13 |
| 20.63 | 4.30 | 8 |
| 21.00* | 4.23 | 54 |
| 21.48 | 4.13 | 8 |
| 22.14 | 4.01 | 3 |
| 22.65 | 3.92 | 9 |
| 22.87* | 3.88 | 22 |
| 23.73 | 3.75 | 7 |
| 23.90 | 3.72 | 5 |
| 24.17* | 3.68 | 29 |
| 24.37 | 3.65 | 13 |
| 24.67* | 3.61 | 44 |
| 25.11 | 3.54 | 6 |
| 25.18 | 3.53 | 5 |
| 25.66 | 3.47 | 7 |
| 25.78 | 3.45 | 6 |
| 25.85 | 3.44 | 4 |
| 26.32 | 3.38 | 15 |
| 27.06 | 3.29 | 6 |
| 27.82 | 3.20 | 13 |
| 27.99 | 3.18 | 6 |
| 28.27 | 3.16 | 10 |
| 28.56 | 3.12 | 9 |
| 28.64 | 3.12 | 11 |
| 29.13 | 3.06 | 3 |
| 29.25 | 3.05 | 4 |

-continued

Peak list Form B: Peak list determined from the transmission powder X-ray diffraction pattern of Form B, according to FIG. 14. Accuracy of degrees 2-theta is provided at 2 decimal points, some variation dependent on batch or device may be evident.

| 2θ (°) | d (Å) | I (%) |
|---|---|---|
| 29.34 | 3.04 | 3 |
| 29.45 | 3.03 | 2 |
| 29.71 | 3.00 | 4 |
| 29.83 | 2.99 | 7 |

*Peaks may in some embodiments be considered as prominent peaks observed in the XRPD pattern.

Form C:

In another aspect, the invention relates to a crystalline solid form of Alpha-1062 gluconate, designated Form C.

The invention therefore relates to a crystalline solid form of Alpha-1062 gluconate (Form C), wherein said crystalline form has prominent peaks at 3.90, 9.74, 10.35 and 21.43 (also optionally 15.66 and/or 23.90) degrees 2-theta (±0.2) in a powder X-ray diffraction pattern.

These 4 peaks are selected from the prominent peak list provided below and appear to exhibit no substantial overlap with prominent peaks in the XRPD patterns for Forms A, B or D or Materials E-G. In one embodiment, Form C can therefore be reliably distinguished using one or more prominent peaks, for example as mentioned above or as in FIG. 20 or Table 8, upon comparison of the corresponding powder X-ray diffraction patterns. In one embodiment, the presence of these peaks in a powder X-ray diffraction pattern may be used to distinguish Form C from the solid forms described previously in the art, for example those described in WO2014/016430.

In one embodiment, Form C has at least five prominent peaks selected from the list consisting of 3.90, 9.74, 10.35, 10.65, 13.35, 15.01, 15.66, 16.08, 16.46, 17.43, 19.77, 21.43 and 22.32 degrees 2-theta (±0.2) in a powder X-ray diffraction pattern. This peak list represents a list of prominent peaks from Table 8 for Form C.

In one embodiment, Form C has at least three prominent peaks selected from the list consisting of 10.35, 13.35, 15.01, 16.08 and 16.46 degrees 2-theta (±0.2) in a powder X-ray diffraction pattern. This peak list represents a list of the 5 most intense peaks from Table 8 for Form C.

Typically, not all peaks from this list need be detected in order to determine the presence of Form C in any given preparation. According to the invention, for example in some embodiments, 1, 2, 3, 4, 5, 6, 7, 8, 9, 10 or more peaks, preferably those with relatively high signal intensity, may be employed to determine any given crystal form. For example, the 4, 5, 6, 7, 8, 9 or 10 most intense peaks may be employed to identify any given crystal form. In one embodiment, sufficient identification of any given crystal form, such as Form C, is achieved when the presence of at least four prominent peaks can be determined based on XRPD comparisons.

In one embodiment, Form C has a peak at 7.85 degrees 2-theta (±0.2) in a powder X-ray diffraction pattern. This peak is of relatively low intensity compared to the peaks outlined above as predominant peaks. However, a peak at 7.85 degrees 2-theta appears to be absent in all other patterns for Forms A, B or D or Materials E-G.

In one embodiment, Form C exhibits an onset of melting at a temperature of 115-125° C., preferably at about 119° C., when assessed using differential scanning calorimetry (DSC).

In one embodiment, Form C exhibits a weight loss of 0.5-1.5%, preferably about 0.9%, up to 121° C., when assessed using Thermo-Gravimetric Analysis (TGA).

In one embodiment, Form C has a good solubility in water and may be suitable for pharmaceutical formulation and administration.

Peak list Form C: Peak list determined from the transmission powder X-ray diffraction pattern of Form C, according to FIG. 20. Accuracy of degrees 2-theta is provided at 2 decimal points, some variation dependent on batch or device may be evident.

| 2θ (°) | d (Å) | I (%) |
|---|---|---|
| 3.90* | 22.6 | 50 |
| 7.85 | 11.3 | 19 |
| 9.74* | 9.07 | 31 |
| 10.35* | 8.54 | 65 |
| 10.65* | 8.30 | 55 |
| 12.27 | 7.21 | 12 |
| 13.35* | 6.63 | 76 |
| 15.01* | 5.90 | 100 |
| 15.66* | 5.65 | 36 |
| 15.78 | 5.61 | 26 |
| 16.08* | 5.51 | 75 |
| 16.46* | 5.38 | 91 |
| 17.43* | 5.08 | 36 |
| 18.12 | 4.89 | 22 |
| 18.22 | 4.86 | 19 |
| 18.95 | 4.68 | 9 |
| 19.77* | 4.49 | 54 |
| 20.14 | 4.40 | 18 |
| 20.25 | 4.38 | 20 |
| 21.43* | 4.14 | 36 |
| 22.32* | 3.98 | 53 |
| 22.91 | 3.88 | 18 |
| 23.36 | 3.80 | 15 |
| 23.63* | 3.76 | 29 |
| 23.90* | 3.72 | 54 |
| 24.48 | 3.63 | 11 |
| 25.03 | 3.56 | 15 |
| 25.26 | 3.52 | 32 |
| 25.72 | 3.46 | 11 |
| 25.99 | 3.43 | 31 |
| 26.70 | 3.34 | 17 |
| 26.91 | 3.31 | 10 |
| 27.08 | 3.29 | 14 |
| 27.79 | 3.21 | 13 |
| 27.88 | 3.20 | 14 |
| 28.54 | 3.12 | 19 |
| 28.84 | 3.09 | 12 |
| 29.54 | 3.02 | 8 |
| 29.94 | 2.98 | 10 |
| 30.29 | 2.95 | 19 |

*Peaks may in some embodiments be considered as prominent peaks observed in the XRPD pattern.

Form D:

In another aspect, the invention relates to a crystalline solid form of Alpha-1062 gluconate, designated Form D.

The invention therefore relates to a crystalline solid form of Alpha-1062 gluconate (Form D), wherein said crystalline form has prominent peaks at 3.76, 10.16, 14.77 and 19.03 (also optionally 17.96, 18.86 and/or 28.14) degrees 2-theta (±0.2) in a powder X-ray diffraction pattern.

These 4 peaks are selected from the prominent peak list provided below and appear to exhibit no substantial overlap with prominent peaks in the XRPD patterns for Forms A-C or Materials E-G. In one embodiment, Form D can therefore be reliably distinguished using one or more prominent peaks, for example as mentioned above or as in FIG. 28 or Table 8, upon comparison of the corresponding powder X-ray diffraction patterns. In one embodiment, the presence of these peaks in a powder X-ray diffraction pattern may be used to distinguish Form D from the solid forms described previously in the art, for example those described in WO2014/016430.

In one embodiment, Form D has at least five prominent peaks selected from the list consisting of 3.76, 10.16, 13.35, 13.75, 14.77, 16.27, 16.70, 17.24, 17.96, 18.86, 19.03, 19.87 and 20.15, 21.21 degrees 2-theta (±0.2) in a powder X-ray diffraction pattern. This peak list represents a list of prominent peaks from Table 8 for Form D.

In one embodiment, Form D has at least three prominent peaks selected from the list consisting of 3.76, 10.16, 13.35, 14.77 and 19.03 degrees 2-theta (±0.2) in a powder X-ray diffraction pattern. This peak list represents a list of the 5 most intense peaks from Table 8 for Form D.

Typically, not all peaks from this list need be detected in order to determine the presence of Form D in any given preparation. According to the invention, for example in some embodiments, 1, 2, 3, 4, 5, 6, 7, 8, 9, 10 or more peaks, preferably those with relatively high signal intensity, may be employed to determine any given crystal form. For example, the 4, 5, 6, 7, 8, 9 or 10 most intense peaks may be employed to identify any given crystal form. In one embodiment, sufficient identification of any given crystal form, such as Form D, is achieved when the presence of at least four prominent peaks can be determined based on XRPD comparisons.

In one embodiment, Form D has peaks at 7.53 and/or 12.09 degrees 2-theta (±0.2) in a powder X-ray diffraction pattern. These peaks are of relatively low intensity compared to the peaks outlined above as predominant peaks. However, peaks at 7.53 and/or 12.09 degrees 2-theta appear to be absent in all other patterns for Forms A-C or Materials E-G.

In one embodiment, Form D is a metastable form. As demonstrated in the examples below, Form D eventually converts to Form B with extended exposure to relative humidity ≥52% RH or converts to Form C at exposure to relative humidity <52% RH. In one embodiment, Form D has a good solubility in water and may be suitable for pharmaceutical formulation and administration.

Peak list Form D: Peak list determined from the transmission powder X-ray diffraction pattern of Form D, according to FIG. 28. Accuracy of degrees 2-theta is provided at 2 decimal points, some variation dependent on batch or device may be evident.

| 2θ (°) | d (Å) | I (%) |
|---|---|---|
| 3.76* | 23.5 | 48 |
| 7.53 | 11.7 | 11 |
| 9.62 | 9.19 | 6 |
| 10.16* | 8.70 | 100 |
| 11.00 | 8.04 | 20 |
| 12.09 | 7.32 | 11 |
| 13.35* | 6.63 | 49 |
| 13.75* | 6.44 | 36 |
| 14.42 | 6.14 | 5 |
| 14.77* | 5.99 | 42 |
| 15.15 | 5.84 | 17 |
| 15.22 | 5.82 | 15 |
| 16.27* | 5.44 | 32 |
| 16.70* | 5.30 | 39 |
| 17.24* | 5.14 | 40 |
| 17.44 | 5.08 | 18 |
| 17.96* | 4.94 | 24 |
| 18.86* | 4.70 | 41 |
| 19.03* | 4.66 | 75 |
| 19.52 | 4.54 | 14 |
| 19.87* | 4.46 | 29 |
| 20.15* | 4.40 | 39 |
| 20.42 | 4.35 | 20 |
| 21.21* | 4.19 | 30 |
| 21.63 | 4.10 | 13 |
| 22.30 | 3.98 | 22 |
| 22.79 | 3.90 | 8 |
| 23.21* | 3.83 | 27 |
| 23.49 | 3.78 | 20 |
| 23.88 | 3.72 | 13 |
| 24.40 | 3.64 | 17 |
| 24.79 | 3.59 | 7 |
| 25.08 | 3.55 | 30 |
| 25.88 | 3.44 | 6 |
| 26.51 | 3.36 | 7 |
| 26.91 | 3.31 | 4 |
| 27.79 | 3.21 | 5 |
| 28.14 | 3.17 | 36 |
| 28.33 | 3.15 | 10 |
| 28.58 | 3.12 | 6 |
| 28.91 | 3.09 | 23 |
| 29.34 | 3.04 | 7 |
| 29.81 | 3.00 | 12 |
| 30.15 | 2.96 | 4 |
| 30.59 | 2.92 | 5 |
| 31.39 | 2.85 | 14 |
| 31.67 | 2.82 | 9 |

*Peaks may in some embodiments be considered as prominent peaks observed in the XRPD pattern.

Preparations:

In another aspect, the invention relates to a preparation comprising the crystalline solid Form A as described herein, wherein said preparation is essentially free of, or comprises at negligible levels, one or more additional crystalline solid forms of Alpha-1062 gluconate (such as Forms B, C and/or D, or Materials E-G).

In one embodiment, the preparation is essentially free of, or comprises at negligible levels, one or more additional crystalline solid forms selected from the group consisting of:
  i. Form B, wherein said Form B is as described herein, and preferably has prominent peaks at 10.69, 17.17, 21.00 and 24.67 degrees 2-theta (±0.2) in a powder X-ray diffraction pattern,
  ii. Form C, wherein said Form C is as described herein, and preferably has prominent peaks at 3.90, 9.74, 10.35 and 21.43 degrees 2-theta (±0.2) in a powder X-ray diffraction pattern, and
  iii. Form D, wherein said Form D is as described herein, and preferably has prominent peaks at 3.76, 10.16, 14.77 and 19.03 degrees 2-theta (±0.2) in a powder X-ray diffraction pattern.

As described at length in the examples, Form A is anhydrous and appears to be the most stable of Forms A-D when maintained in suitable conditions. Form A can therefore be maintained in an essentially "pure" form, or in a form essentially free of, or comprising at negligible levels, one or more additional crystalline solid forms B-D and/or Materials E-G.

From examples described herein, Form A (anhydrate) appears to be the most stable Form at low water activities of less than about 0.12 $a_w$ (12% RH). Furthermore, Form A appears kinetically stable in the solid state at 43% RH (RT) and was sustained up to 5 days at that condition. Above this water activity, up to about 0.5 $a_w$, Form A converts to Form C (Monohydrate). Above 0.5 $a_w$, Form B (Tetrahydrate) is formed. Form D (Dihydrate) was only observed from exposure at about 75% RH or by drying. Form D does not appear stable at any of the conditions evaluated and readily converts to other Forms dependent upon the storage humidity.

The invention therefore relates to Form A preparations either free of Forms B-G, or preparations that include them at low or negligible levels, thereby covering "pure" Form A compositions or compositions that may transition depending on water content. Most preferred are compositions comprising Form A in an essentially stable anhydrous form without (significant) conversion to the pseudopolymorph hydrate forms.

Methods:

In another aspect, the invention relates to a method for preparing the crystalline solid Form A, comprising contacting an Alpha-1062 gluconate with an organic solvent, preferably selected from the list consisting of methyl ethyl ketone (MEK), 1,4-dioxane (dioxane), ethyl acetate (EtOAc) and tetrahydrofuran (THF), preferably forming a slurry and subsequently filtering and/or drying the slurry, obtaining a crystalline solid form.

In one embodiment, the method comprises combining Alpha-1062 gluconate and a solvent and inducing the salt to crystallize under suitable crystallization conditions.

In one embodiment, the crystallization conditions comprise contacting the gluconic acid (gluconate) salt of Alpha-1062 with a solvent to form a slurry and/or suspension.

In one embodiment, the Alpha-1062 gluconate is provided in solid form. Preferred methods of preparing Alpha-1062 gluconate are disclosed in the examples below Preferably, the solid form of Alpha-1062 gluconate is mixed to create a slurry and/or suspension. Optionally, the slurry may be stirred and/or heated. In a preferred embodiment, the slurry is formed and stirred at a temperature of 15 to 25° C., more preferably between 18 to 22° C., such as at about 20° C. In one embodiment, the slurry is formed and stirred at room temperature, e.g. under common laboratory conditions.

In one embodiment, the method for forming Form A comprises using an organic solvent to form a suspension and/or slurry with the Alpha-1062 gluconate.

In one embodiment, the method for forming Form A comprises using an organic solvent without water to form a suspension and/or slurry.

In one embodiment, the method for forming Form A of the Alpha-1062 gluconate, comprises using methyl ethyl ketone (MEK), also known as butanone, as a solvent to form a suspension and/or slurry.

As described in the examples below, the inventors observed that forming a slurry with the Alpha-1062 gluconate and MEK at 20° C. formed a yellowish, beige or light orange suspension that maintained its visual properties and thickness throughout stirring. Filtering and drying of the solid form produced a light yellow/orange colored solid material with Form A, defined by the powder X-ray diffraction patterns for Form A outlined above and in the examples below.

In one embodiment, the invention therefore relates to a method for preparing the crystalline solid Form A, as described herein, comprising contacting an Alpha-1062 gluconate with MEK, forming a slurry, and filtering and/or drying the slurry to obtain a solid crystal form.

In one embodiment, the invention therefore relates to a method for preparing the crystalline solid Form A, as described herein, comprising contacting an Alpha-1062 gluconate with MEK, forming a slurry, stirring the slurry at a temperature between 15-25° C., preferably at about 20° C., filtering the slurry to remove the MEK, optionally washing the solid form obtained via filtering with MEK and repeating filtering, and drying the slurry to obtain Form A. In a preferred embodiment, the solvent used to form the slurry is MEK without water.

A method for producing the pseudopolymorph hydrate forms described herein (Forms B-D) of the Alpha-1062 gluconate is also disclosed herein, comprising contacting an Alpha-1062 gluconate with MEK and water, forming a slurry, and filtering and/or drying the slurry to obtain a solid crystal form.

As described in the examples below, the inventors observed that forming a re-slurry with the Alpha-1062 gluconate and MEK mixed with water at 20° C. formed a yellow or orange suspension that led to a thick suspension throughout stirring. Filtering of the solid form was difficult and relatively slow. Drying of the material produced an orange colored solid material with a hydrate form defined by the powder X-ray diffraction patterns for Forms B-D outlined above and in the examples below. The Forms B-D can be produced by transition between forms due to moisture in the atmosphere as described herein.

Form A is advantageous over Forms B-D for many applications because the properties that Form A offers include, for example, in some embodiments, greater thermodynamic stability, higher crystallinity, and/or higher solubility than other Forms.

Numerous factors affect crystallization conditions, and they are well known to one of skill in the art. Alternative means for crystallization may therefore be employed. Such factors include, for example the concentration of the salt in the solvent (crystallization solution), the difference, if any, between the initial and final temperatures of the crystallization solution, the rate of cooling, if any, the solvent vaporization rate, if any, potential seeding, a potential supersaturation ratio, and/or the presence of a precipitant, if any. With guidance from the disclosure provided herein, one of skill in the art, without undue experimentation, may select and/or adjust one or more appropriate factors to arrive at crystallization conditions to provide one of the Forms A-D described herein.

Pharmaceutical Compositions and Medical Use:

In another aspect, the invention relates to a pharmaceutical composition comprising the crystalline solid Form A as described herein and/or a preparation with Form A as described herein, wherein said composition additionally comprises one or more pharmaceutically acceptable excipients. Pharmaceutical excipients are known to a skilled person and may be selected depending on, for example, medical indication, patient, administration route, dose and formulation.

In one embodiment, the pharmaceutical composition of the invention and/or the preparation of the invention, comprising the crystalline solid Form A as described herein, is packaged to reduce atmospheric moisture in contact with said composition. Suitable packaging is known to a skilled person. In some embodiments, aluminium foil blister packaging (Alu-Alu), packaging with polymeric films with aluminium layers(s) and/or using a desiccant are employed.

In one embodiment, the pharmaceutical composition is suitable for oral or transmucosal administration.

In one embodiment, the pharmaceutical composition is for use in the treatment of a brain disease associated with cognitive impairment. The invention further relates to methods for treating brain disease associated with cognitive impairment comprising administering a composition or a preparation of the invention to a subject in need thereof.

In one embodiment, the brain disease is associated with a cholinergic deficit. In one embodiment, the composition is used as or for use as a nicotinic acetylcholine receptor sensitizing agent.

In one embodiment, the brain disease is selected from the group consisting of a brain disease with a cholinergic deficit, Alzheimer's disease, Parkinson's disease, dementia, schizophrenia, epilepsy, stroke, poliomyelitis, neuritis, myopathy, oxygen and nutrient deficiencies in the brain after hypoxia, anoxia, asphyxia, cardiac arrest, chronic fatigue syndrome, poisoning, anaesthesia, spinal cord disorders, central inflammatory disorders, autism, Rett's syndrome, postoperative delirium, neuropathic pain, abuse of alcohol and drugs, addictive alcohol and/or nicotine craving, and effects of radiotherapy.

A further aspect of the invention relates to a kit, or kit-of-parts, comprising a preparation of the Form A as described herein and one or more other components useful in preparing a pharmaceutical composition. Preferably, Form A is packaged and/or prepared to reduce atmospheric moisture in contact with said solid form.

In some embodiments, such a kit may comprise one or more additional solvents, such as water, in order to prepare a solution or other formulation of the Alpha-1062 gluconate for administration to a patient.

In some embodiments, Form A as described herein shows a higher solubility in water and improved stability upon storage compared to other solid forms of the Alpha-1062 gluconate described in the art.

In one embodiment, Form A as described herein is prepared for formulation in solution, preferably for transmucosal administration.

In one embodiment, Form A as described herein is prepared for formulation in a tablet for administration in the oral cavity, such as a sub-lingual or buccal tablet or film formulation, preferably for transmucosal administration.

Preferred but non-limiting modes of transmucosal administration are selected preferably from oral, intranasal, sublingual or buccal administration, of a therapeutically effective amount of Alpha-1062 gluconate. The enhanced solubility of Form A as described herein represents a surprising and beneficial development. The high solubility enables higher concentrations of the compound to be administered in smaller volumes, thereby further enhancing administration via e.g. transmucosal administration.

The preferred transmucosal administration represents a beneficial mode of delivery due to a combination of factors. The enhanced solubility allows higher concentrations of Alpha-1062 to be administered, thereby enabling larger amounts of the active substance after cleavage (galantamine) to be active in the brain. The transport of Alpha-1062 (measured either by Alpha-1062 itself in the brain or by galantamine levels in the brain after cleavage of the prodrug) is improved over galantamine, thereby enabling galantamine to be delivered more effectively to the brain than was previously possible. The prodrug properties of Alpha-1062 are exploited and enhanced in a beneficial manner by the transmucosal application of the gluconate salt. Form A as described herein further enhances these modes of administration by its high solubility.

The invention therefore also relates to a method for treating a brain disease associated with cognitive impairment in a subject, the method comprising administering a therapeutically effective amount of the Alpha-1062 gluconate to a subject in need thereof.

In one embodiment, the gluconate salt of Alpha-1062 is administered at a dosage of from 0.1 to 200 mg, 1 to 100 mg, preferably 2 to 40 mg, preferably from one to three times daily, more preferably twice daily, and even more preferably only once daily.

In one embodiment, the gluconate salt of Alpha-1062 is administered intranasally, bucally or sublingually, preferably as a 2 to 40% weight per volume (w/v) solution, for example at an amount of 20 to 100 microliters, preferably in a single (intranasal or oral (sub-lingual/buccal)) spray event, for example from one to three times daily.

In one embodiment, the brain disease to be treated is Alzheimer's disease, and the gluconate salt of Alpha-1062 of or obtained from the crystal form I is administered intranasally, buccally or sublingually, as an about 10% weight per volume (w/v) solution at an amount of 20-100 microliters, e.g. about 50 microliters, in 1-3, preferably in a single administration event, twice daily.

In one embodiment, the intranasal application is carried out by administering a therapeutically effective amount of the gluconate salt of Alpha-1062 of or obtained from the crystal form I using a suitable metered dose device such as a atomizer, sprayer, pump spray, dropper, squeeze tube, squeeze bottle, pipette, ampule, nasal cannula, metered dose device, nasal spray inhaler, nasal continuous positive air pressure device, and/or breath actuated bi-directional delivery device.

In one embodiment, the sublingual administration is carried out by administering a therapeutically effective amount of the gluconate salt of Alpha-1062 of or obtained from Form A under the tongue by placing one or more drops of a solution, or an amount of particulate in the form of freeze-dried powder or emulsion underneath the tongue, or using a sub-lingual tablet or film formulation, and/or by spraying the underside of the tongue with a preselected volume of a liquid composition comprising the gluconate salt of Alpha-1062 of or obtained from Form A.

In one embodiment, the buccal administration is carried out by administering a therapeutically effective amount of the gluconate salt of Alpha-1062 of or obtained from Form A to the buccal vestibule inside the mouth between the cheek and the gums, such as via a powder or emulsion, or a tablet or film formulation, or an orally disintegrating or orodispersible tablet (ODT).

DETAILED DESCRIPTION OF THE INVENTION

The invention relates to a stable, crystalline form of a gluconic acid salt of Alpha-1062. The invention therefore relates to a crystalline solid form of Alpha-1062 gluconate (Form A), wherein said crystalline form has prominent peaks at 3.61, 10.98, 14.41 and 18.44 degrees 2-theta (±0.2) in a powder X-ray diffraction pattern.

Drug Substance:

The pharmaceutical substance of the present invention is Alpha-1062 (also known as Memogain®, GLN-1062, PubChem CID 44240142, galantamine benzoate, CAS: 224169-27-1). The salt employed in the present invention is the gluconate salt of Alpha-1062. FIG. 1 provides the chemical structure of Alpha-1062 gluconate.

Chemical Name (IUPAC, computed by LexiChem 2.6.6): [(1S,12S,14R)-9-methoxy-4-methyl-11-oxa-4-azatetracyclo[8.6.1.01,12.06,17]heptadeca-6(17),7,9,15-tetraen-14-yl] benzoate.

Molecular formula of free base: $C_{24}H_{25}NO_4$; Molecular formula of gluconic acid: $C_6H_{12}O_7$; Molecular weight of free base: 391.47 g/mol; Molecular weight of Alpha-1062 gluconate: 587.61 g/mol; Conversion factor: 1 mg base=1.501 mg salt.

There are three chiral centres present in the galantamine benzoyl ester cation and four chiral centres present in the gluconate anion. The gluconate salt is a white to pale yellow powder.

There is substantial evidence from pre-clinical studies in several animal species that intravenous, intranasal, sublingual or buccal administration of Alpha-1062 rapidly achieves higher brain concentrations of galantamine than oral administration of galantamine and with a proportionally higher brain:blood concentration ratio. The data generated in pre-clinical and clinical phase I studies suggest that greater effectiveness (potency) with improved tolerability is achievable by administration of Alpha-1062, over galantamine administered by the established oral route.

The present invention now provides a novel, beneficial crystalline form of Alpha-1062, suitable for use in pharmaceutical preparations.

Solid Forms:

As used herein, amorphous solids are not crystalline due to the disordered arrangements of the drug substance molecules in the solid state.

As used herein, polymorphism is the existence of a drug substance in multiple crystalline forms which exhibit differing arrangements/conformations of the molecules in a crystal lattice which can affect the solid-state properties of the material. For example, Form A as described herein may be considered a polymorph of the Alpha-1062 gluconate.

As used herein, pseudo-polymorphism is the existence of a drug substance in a crystalline form which contains solvates/hydrates bound within a crystal lattice with the drug substance. For example, the hydrate Forms B-D may be considered pseudopolymorphs of Alpha-1062 gluconate.

As used herein, hydrates are crystalline forms that include water molecules in their crystal lattice. In addition to polymorphs and the amorphous solid state, other examples of possible solid states are solvates and hydrates. Hydrates are frequently encountered solvates in pharmacy, because water is applied for many processing steps. APIs when exposed to water may form hydrates and hydrates may lose their water under high temperature or low humidity.

As used herein, crystalline preferably means a material that has an ordered, long range molecular structure. The degree of crystallinity of a crystal form can be determined by many techniques including, for example, powder X-ray diffraction, moisture sorption, differential scanning calorimetry, solution calorimetry, and dissolution properties.

Crystalline organic compounds consist of a large number of atoms that are arranged in a periodic array in three-dimensional space. The structural periodicity normally manifests distinct physical properties, such as sharp, explicit spectral features by most spectroscopic probes (e.g., X-ray diffraction, infrared and solid-state NMR). X-ray diffraction (XRD) is acknowledged to be one of the most sensitive methods to determine the crystallinity of solids. Crystals yield explicit diffraction maxima that arise at specific angles consistent with the lattice interplanar spacings, as predicted by Bragg's law. On the contrary, amorphous materials do not possess long-range order. They often retain additional volume between molecules, as in the liquid state. Amorphous solids normally unveil a featureless XRD pattern with broad, diffuse halos because of the absence of the long-range order of repeating crystal lattice.

Crystalline forms are preferred in many pharmaceutical applications. Crystalline forms are generally thermodynamically more stable than amorphous forms of the same substance. This thermodynamic stability is preferably reflected in the improved physical stability of the crystalline form. The regular packing of the molecules in the crystalline solid preferably denies the incorporation of chemical impurities. Hence crystalline materials generally possess higher chemical purity than their amorphous counterparts. The packing in the crystalline solid generally constrains the molecules to well defined lattice positions and reduces the molecular mobility that is the prerequisite for chemical reactions. Hence, crystalline solids, with very few notable exceptions, are chemically more stable than amorphous solids of the same molecular composition. Preferably, the crystalline forms of the Alpha-1062 gluconate disclosed in the present application possess one or more of the advantageous chemical and/or physical properties disclosed herein.

As used herein, the term stable may relate to either chemical stability or to polymorph stability. Polymorph stability refers to the likelihood of a polymorph form remaining in its specific crystalline state under suitable storage conditions. For example, a stable polymorph form will maintain at least about 95% by weight, preferably at least about 98% by weight, and more preferably at least about 99% by weight or more of the crystalline form, in other words the form remains unchanged after storage under the indicated conditions for the indicated time. In the context of the present invention, Form A of the Alpha-1062 gluconate appears to show good stability for example under conditions of storage at room temperature, and at low water activities, such at or under about 43% RH or of less than 0.12 $a_w$, for multiple months. In some embodiments, Form A shows good chemical stability. In other words, Alpha-1062 gluconate as Form A shows low, negligible or no conversion to distinct chemical structures, after storage under the appropriate conditions.

Powder X-Ray Diffraction (PXRD):

Powder X-ray diffraction (PXRD) measures the diffraction pattern of a crystalline material. Each active pharmaceutical ingredient (API) will produce a specific pattern depending on the structure of its crystal lattice. Each polymorph, pseudopolymorph, polymorph salt, or co-crystalline material will have its own specific pattern. For this reason, PXRD of an API can be carried out in controlled conditions to assess the presence or absence of crystalline material and any form conversions.

PXRD can also be used to determine if any change in crystalline form in the drug product has occurred during e.g. storage or stability studies. The identification of a crystalline form therefore relies on the presence of detectable diffraction peaks for any given crystalline form. In addition, the API peaks must be distinguishable from any crystalline excipient peaks, should a composition be assessed post-formulation. PXRD can also be used as a qualitative and sometime quantitative assessment of the degree of crystallinity of a pure API. A skilled person can assess PXRD patterns and identifying the presence and/or absence of suitable peaks that can be employed to characterize any given crystalline form of an API without undue effort.

In some embodiments, the peaks determined by a PXRD analysis are essentially the same as those presented in the examples below. The term "essentially the same" with reference to PXRD means that variabilities in peak positions and relative intensities of the peaks are to be taken into account. For example, a typical precision of the 2-Theta values is in the range of ±0.2° 2-Theta.

As used herein, characteristic XRPD peaks are a subset of the representative peaks from XRPD patterns of a crystalline form of a material that statistically can be proven to differentiate it from the other crystalline forms of that material. Not all crystalline polymorphs of a material necessarily have characteristic peaks.

As used herein, prominent XRPD peaks are typically the strongest low angle, non-overlapping peaks observed in the XRPD pattern. In some embodiments, the "prominent peaks" have preferably a ≥20% relative intensity, preferably ≥30% relative intensity, more preferably ≥40% relative intensity, in a powder X-ray diffraction pattern.

As used herein, representative XRPD Peaks are peaks from XRPD patterns of a crystalline form of a material that statistically show no bias from particle size/shape or preferred orientation during repeated samples and measurements.

As used herein, preferred orientation is phenomena observed in XRPD analyses where due to size/shape of the particles and the pattern collection technique employed it is very difficult or impossible to randomly orient the particles of the material during collection to achieve a pattern with statistically consistent intensities.

With respect to the relative intensities and the prominent peaks of the powder X-ray diffraction patterns mentioned above, the provided values of relative intensity are not intended as limiting for the identification of the prominent or characteristic peaks mentioned. As is known to a skilled person, the relative peak intensities will show some inter-apparatus variability, batch-to-batch variability, as well as variability due to degree of crystallinity, preferred orientation, sample preparation, and as such are provided as an indication and as a qualitative measure only, but not a limiting definition, of the intensities of the peaks in the powder X-ray diffraction patterns.

The term "prominent peak" in the context of defining the present invention is therefore not limited to the respective relative intensities provided above, and any one or more of the respective peaks may be determined as a prominent peak for any given form of Alpha-1062 gluconate. Preferably at least 1, 2, 3 or 4 prominent peaks are used to characterize a crystalline form, in other embodiments, at least 5, 6, 7, 8 9 or 10 prominent peaks may be employed. A prominent peak is therefore also not limited to a peak unique to any given crystal form, rather the peak can, optionally in combination with a number of other peaks from the PXRD pattern, be used to identify a crystal form. In the context of the present invention, crystal Forms A-D may share multiple prominent peaks, but also exhibit peaks distinct from one another that can be used to differentiate between any two forms. In some embodiments, the prominent peaks mentioned in the embodiments of the invention may also be characteristic peaks and/or representative peaks.

Analytical Techniques and Terms:

As used herein, ATR (Attenuated Total Reflectance) is an FTIR data collection technique in which a small amount of a solid or liquid sample is placed in direct contact with the ATR crystal such that the IR beam can be internally reflected through the sample creating an evanescent wave that is used to measure the spectrum of the sample.

As used herein, DSC (Differential Scanning calorimetry) is a thermodynamic technique for assessment of the heat energy changes occurring in a sample undergoing a physical or chemical change with a controlled change in temperature.

As used herein, DVS (Dynamic Vapor Sorption) is a gravimetric technique to measure the rate and amount of absorption of a solvent by a sample under controlled conditions.

As used herein, FTIR (Fourier Transform Infrared Spectroscopy) is a simple and reliable technique widely used in the pharmaceutical industry for identification and characterization of materials. The Infrared spectrum can be used for identification of materials because the functional groups of the material give rise to characteristic vibrational bands in terms of both intensity and frequency.

As used herein, NMR (Nuclear Magnetic Resonance) is a technique in which the sample is placed in a strong magnetic field and the NMR active nuclei absorb electromagnetic radiation at a frequency characteristic of the sample. The most common types are proton (1H) and carbon (13C) NMR.

As used herein, TGA (Thermo-Gravimetric Analysis) is a thermogravimetric technique to monitor the changes in the mass of a sample as a function of time and/or temperature.

As used herein, XRPD (X-Ray Powder Diffraction) is a technique for identification and characterization of crystalline materials to ensure the proper phase or polymorph is present. The technique can be used to measure the sample in either a transmission or reflectance mode for analysis.

As used herein, RH (relative humidity) refers to the ratio of the partial pressure of water vapor to the equilibrium vapor pressure of water at a given temperature. In order to determine RH, a hygrometer may be used for measuring the humidity of air. Relative humidity is expressed as a percentage; a higher percentage means that the air-water mixture is more humid.

Compositions and Administration:

The term "active ingredient" or "API" herein refers to the relevant drug molecule (e.g. Alpha-1062) as well as its pharmaceutically acceptable and therapeutically active salts, esters, amides, prodrugs, metabolites, enantiomers, polymorphs, analogs, etc. that induce a desired pharmacological or physiological effect. Terms like "active", "active agent", "active substance" may be used synonymously for "active ingredient". In the context of the present application, Alpha-1062 is considered as an API, although not active itself prior to enzymatic cleavage, it is the pro-drug molecule to be prepared and/or formulated.

The term "effective amount" or "therapeutically effective amount" used interchangeably, is defined to mean the amount or quantity of the drug (e.g. Alpha-1062), which is sufficient to elicit an appreciable biological response when administered to the patient. It will be appreciated that the precise therapeutic dose will depend on the age and condition of the patient, nature of the condition to be treated and will be at the ultimate discretion of the attendant physician.

The pharmaceutical composition may include one or more pharmaceutically acceptable carriers, or excipients. The term "excipient" means a pharmacologically inactive component such as a diluent, disintegrant, carrier, and the like, of a pharmaceutical product. The excipients that are useful in preparing a pharmaceutical composition are generally safe, non-toxic and are acceptable for veterinary as well as human pharmaceutical use. Reference to an excipient includes both one excipient and more than one excipient. The excipients are described herein in some embodiments according to "wt %", or "percentage by weight".

As used herein, "administer" or "administration" refers to the delivery of an API for example in the form of a crystalline form of the present invention or a pharmaceutical composition thereof to an organism for the purpose of prevention or treatment of a brain disease associated with cognitive impairment.

Suitable routes of administration may include, without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. The preferred routes of administration are transmucosal or intravenous.

Pharmaceutical compositions of the present invention may be manufactured by processes well known in the art, e.g., by means of conventional mixing, dissolving, granulating, dragee-making, levigating, emulsifying, encapsulating, entrapping, dissolving or lyophilizing processes. Pharmaceutical compositions for use in accordance with the present invention may be formulated in conventional manner using one or more physiologically acceptable carriers including excipients and auxiliaries that facilitate processing of crystals of the present invention into preparations that can be used pharmaceutically. Proper formulation is dependent upon the route of administration chosen.

For injection or transmucosal administration, a crystal of the present invention or a pharmaceutical composition thereof may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, a crystal of the present invention or a pharmaceutical composition thereof can be formulated by combining a crystal of the present invention with pharmaceutically acceptable carriers well known in the art. Such carriers enable crystals of the present invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, starch and other materials. If desired, disintegrating agents may be added.

For administration by inhalation, a crystal of the present invention or a pharmaceutical composition thereof is conveniently delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of a crystal of the present invention or a pharmaceutical composition thereof, and a suitable powder base such as lactose or starch.

A crystal of the present invention or a pharmaceutical composition thereof may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulating materials such as suspending, stabilizing, and/or dispersing agents.

Pharmaceutical compositions for parenteral administration include aqueous solutions of a water-soluble form of a crystal of the present invention or pharmaceutical composition thereof. Additionally, suspensions of crystals of the present invention or pharmaceutical compositions thereof may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxymethyl cellulose, sorbitol, or dextran. Optionally, the suspension may also contain suitable stabilizers and/or agents that increase the solubility of the crystals of the present invention or a pharmaceutical composition thereof to allow for the preparation of highly concentrated solutions. Alternatively, the active ingredient may be in powder form for constitution with a suitable vehicle, e.g., sterile, pyrogen-free water, before use.

A crystal of the present invention or a pharmaceutical composition thereof may also be formulated in rectal compositions such as suppositories or retention enemas, using, e.g., conventional suppository bases such as cocoa butter or other glycerides.

A preferred mode of administration according to the present invention is transmucosal administration. The term "transmucosal administration" relates to the entering of a pharmaceutical agent through, or across, a mucous membrane. The transmucosal routes of administration of the present invention are preferably intranasal, buccal and/or sublingual.

Nasal or intranasal administration relates to any form of application to the nasal cavity. The nasal cavity is covered by a thin mucosa which is well vascularized. Therefore, a drug molecule can be transferred quickly across the single epithelial cell layer without first-pass hepatic and intestinal metabolism. Intranasal administration is therefore used as an alternative to oral administration of for example tablets and capsules, which lead to extensive degradation in the gut and/or liver.

Buccal administration relates to any form of application that leads to absorption across the buccal mucosa, preferably pertaining to adsorption at the inside of the cheek, the surface of a tooth, or the gum beside the cheek. Sublingual administration refers to administration under the tongue, whereby the chemical comes in contact with the mucous membrane beneath the tongue and diffuses through it.

Pharmaceutical compositions suitable for buccal and/or sub-lingual administration may comprise additional pharmaceutically acceptable carriers or excipients. The active agent can be physically compounded with materials of some or all of classes of ingredients that function as pH controls, preservative agents, viscosity control agents, absorption enhancers, stabilizing agents, solvents, and carrier vehicles. Such agents may be present in either solid or liquid forms of the pharmaceutical composition.

Determination of a therapeutically effective amount and suitable mode of administration is within the capability of those skilled in the art, especially in light of the detailed disclosure provided herein. The amount of a composition administered will, of course, be dependent on the subject being treated, the severity of the affliction, the manner of administration, the judgment of the prescribing physician, etc.

The compositions may, if desired, be presented in a pack or dispenser device, such as an FDA approved kit, which may contain dosage forms containing the active ingredient. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions including a crystal of the present invention formulated in a compatible pharmaceutical carrier may also be prepared, placed in an appropriate container, and labeled for treatment of an indicated condition. Suitable conditions are brain diseases associated with cognitive impairment; preferably those disclosed herein, in particular AD and PD.

Methods:

Based on the disclosure provided herein, a skilled person can produce the inventive crystalline Forms without undue effort. In some embodiments, the method for preparing the crystalline solid Form A, comprises contacting an Alpha-1062 gluconate salt with an organic solvent, preferably MEK, forming a slurry, followed by stirring, filtering and drying the slurry to obtain the solid crystal form.

Organic solvents are a class of volatile carbon-based chemicals capable of dissolving or dispersing one or more other chemical substances. Common organic solvents are classified as aliphatic hydrocarbons, cyclic hydrocarbons, aromatic hydrocarbons, halogenated hydrocarbons, ketones, amines, esters, alcohols, aldehydes, and ethers. The preferred solvent during slurrying, butanone, also known as methyl ethyl ketone (MEK), is an organic compound with the formula $CH_3C(O)CH_2CH_3$. MEK is a ketone with a sharp, sweet odor reminiscent of butterscotch and acetone. It is produced industrially on a large scale, it is soluble in water and is commonly used as an industrial solvent. Also useful may be 1,4-dioxane (dioxane), ethyl acetate (EtOAc) and tetrahydrofuran (THF).

Means for preparing slurries, filtering and drying belong to standard techniques in the pharmaceutical industry, are known to a skilled person and may be employed at laboratory or industrial scale.

The crystal forms or polymorphs of the present invention may also be produced using alternative means to those disclosed herein. A skilled person is capable of adjusting conditions to produce any given crystal form. Generally, polymorph creation is conducted by crystallizing substances from a single or mixed solvent via cooling crystallization, evaporation, or antisolvent crystallization. In addition, heating and cooling rates, crystallization temperature, evaporation rate, the degree of supersaturation, the rate of agitation, pH of the media are variables which can affect the crystallization process and thus, the polymorphs formed. After having identified the surprising crystal forms described herein, a skilled person may adjust these factors in order to reproduce the forms described herein.

BRIEF DESCRIPTION OF THE DRAWINGS

The invention is demonstrated by way of the figures disclosed herein. The figures provide support for a description of potentially preferred, non-limiting embodiments of the invention.

DETAILED DESCRIPTION OF THE PREFERRED EMBODIMENT

Examples

The invention is demonstrated by way of the examples disclosed herein. The examples provide technical support for a detailed description of potentially preferred, non-limiting embodiments of the invention.

Figure 1:
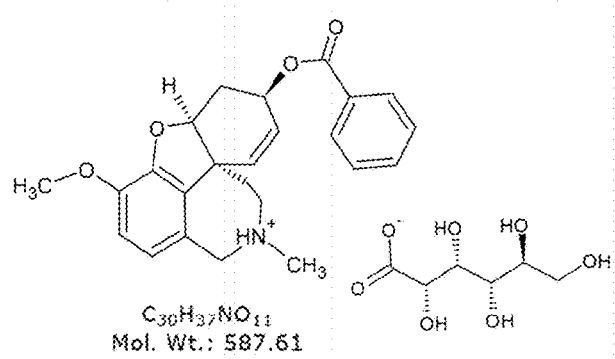
FIG. 1. Chemical Structure of Alpha-1062 Gluconate.
Figure 2:
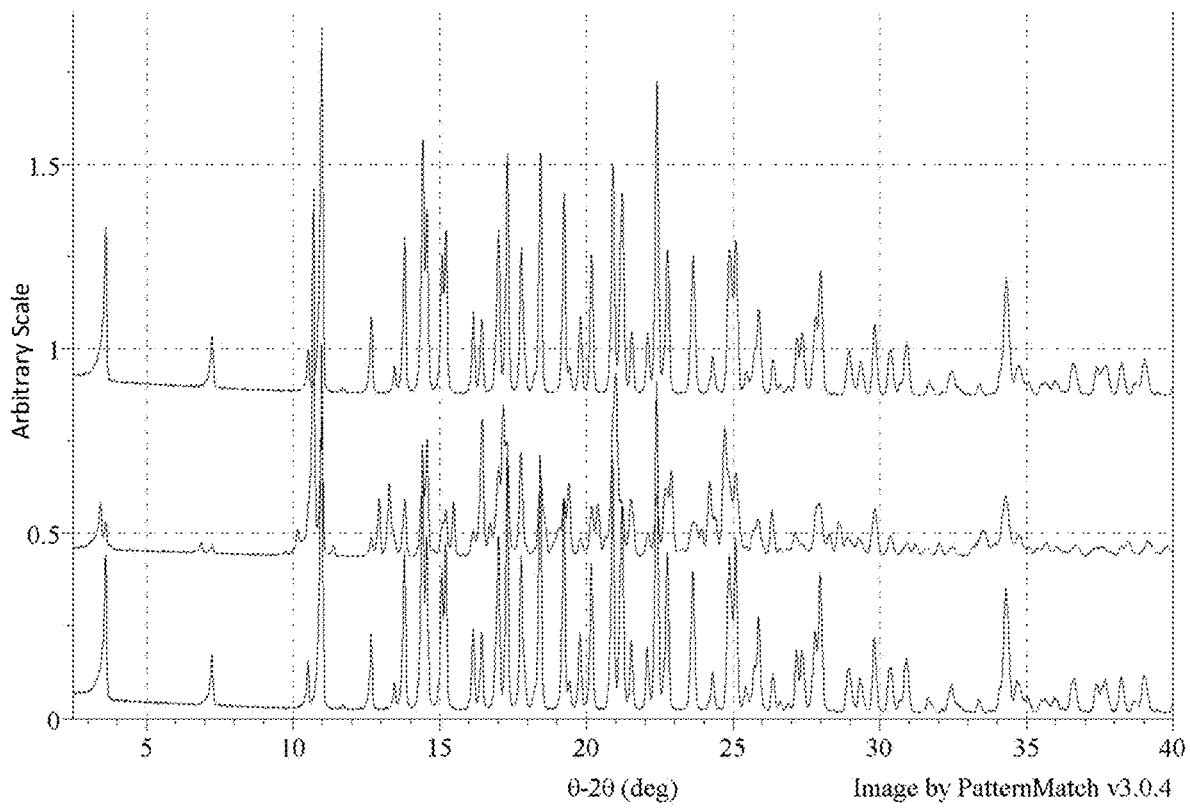
FIG. 2. XRPD patterns of Alpha-1062 Gluconate Study Lots.

Study Materials:

Three lots of Alpha-1062 Gluconate (Galantamine Benzoylester Gluconate) were used to initiate these studies (Table 1). XRPD analyses (FIG. 2) indicate lots CA19-1144 and CA19-0673 are similar. Lot QCL-PLC-I-96 was found to have similar peaks, but also contained many additional peaks, indicative of a mixture of materials.

Figure 3:
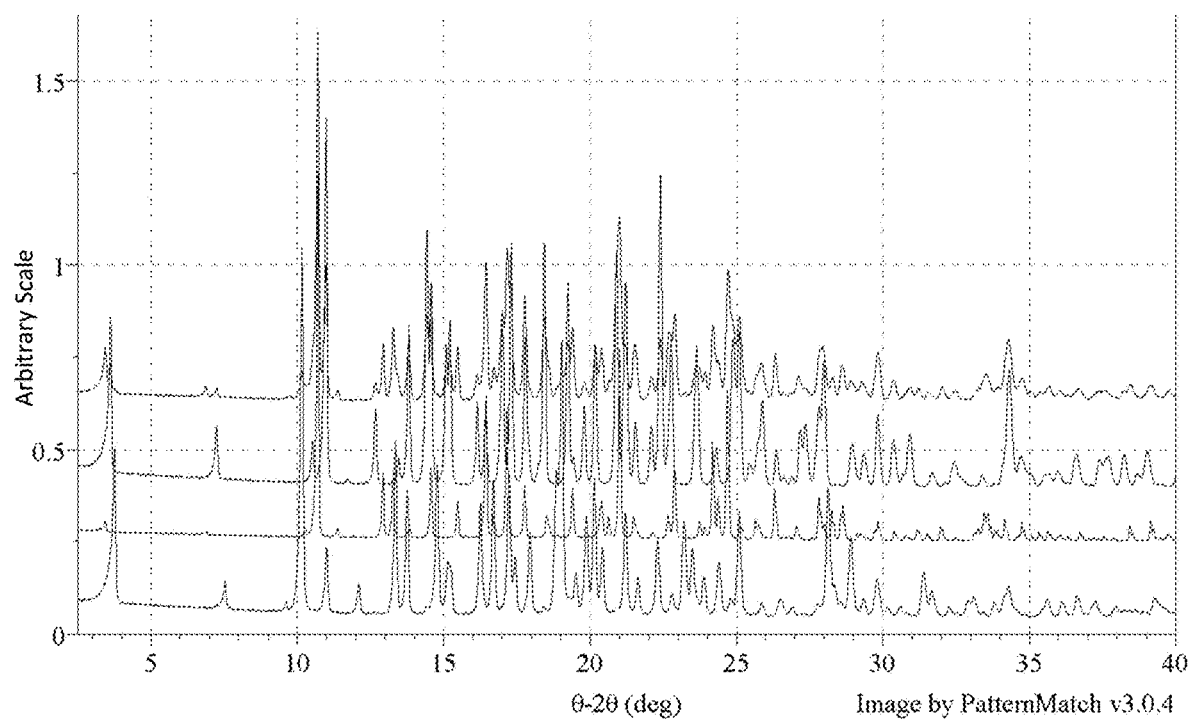
FIG. 3. XRPD pattern comparison of Alpha-1062 Gluconate, lot QCL-PLC-I-96 with pure phases overlaid.
Figure 4:
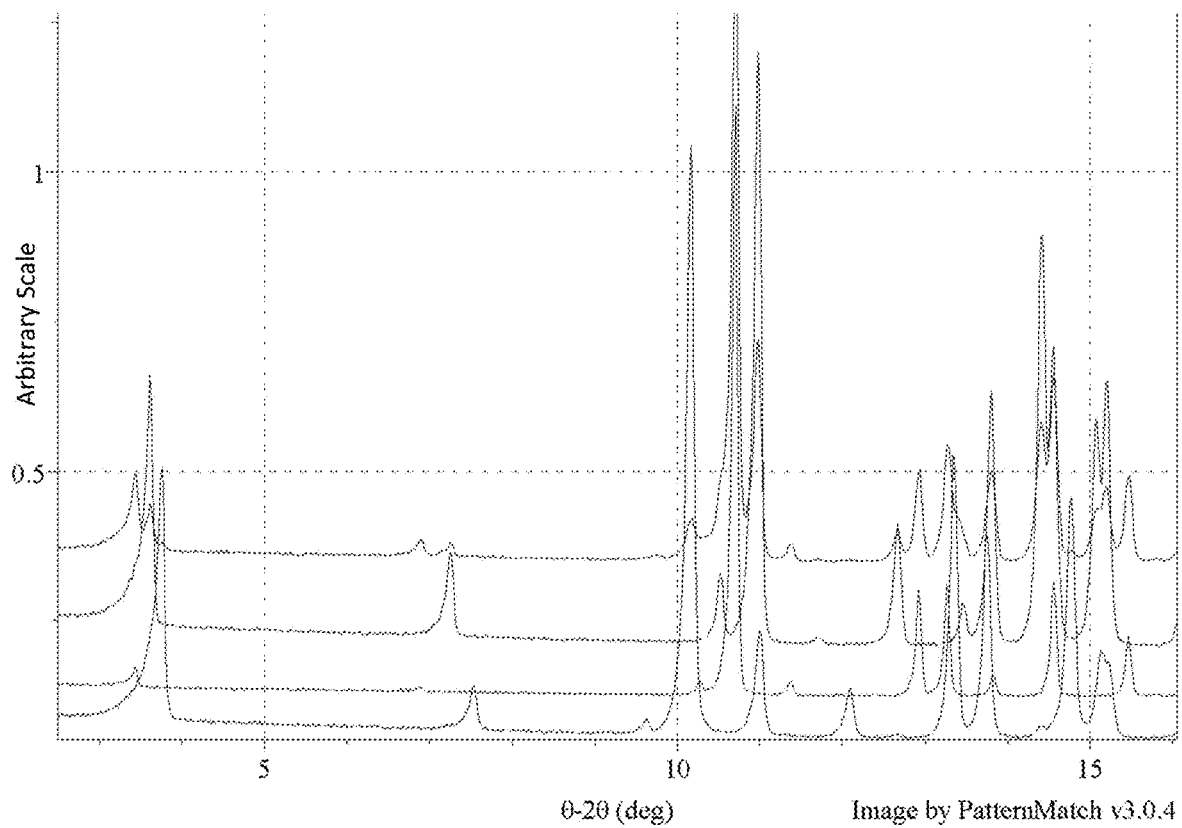
FIG. 4. XRPD pattern comparison of Alpha-1062 Gluconate, lot QCL-PLC-I-96 with pure phases overlaid, expanded view.
Figure 5:
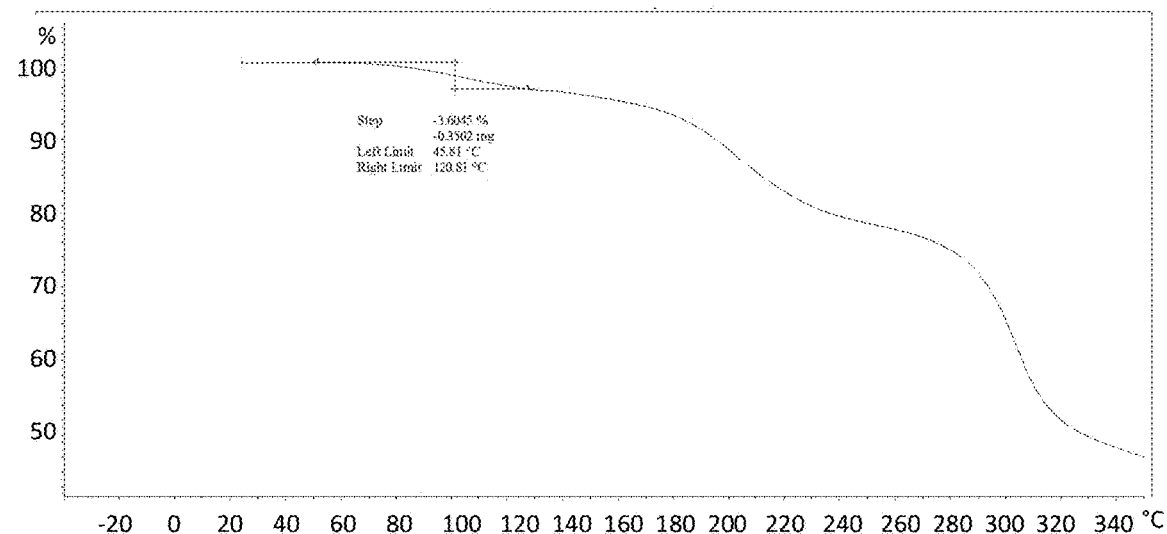
FIG. 5. Thermograms of Alpha-1062 Gluconate, lot QCL-PL-C-I-96, Forms A+B+D.
Figure 5:
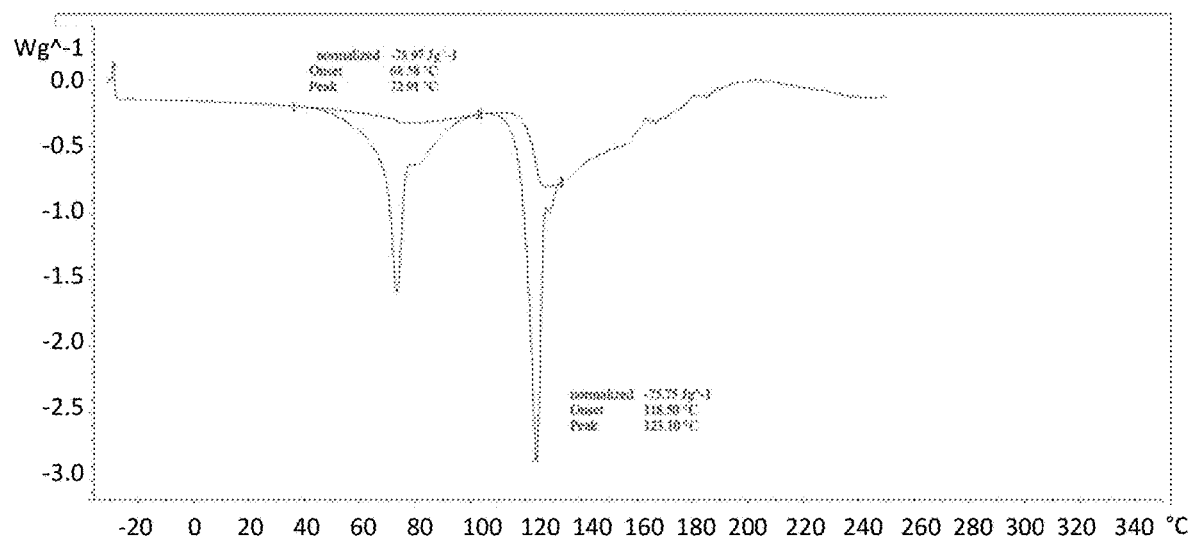

Subsequent studies described below have determined lots CA19-1144 and CA19-0673 to be identified as Form A and determined lot QCL-PLC-I-96 to be a mixture of Forms A, B, and D (FIGS. 3 and 4). Thermal Analysis of the QCL-PLC-I-96 Material (FIG. 5) showed a weight loss of 3.6% up to 121° C. and exhibited a broad endotherm with an onset of 69° C. and a final endotherm with an onset at 119° C. Characterization details of the three lots are provided in Tables 2 through 4. For continuity, lot CA19-1144 is assumed representative of Form A and is discussed further below.

Figure 6:
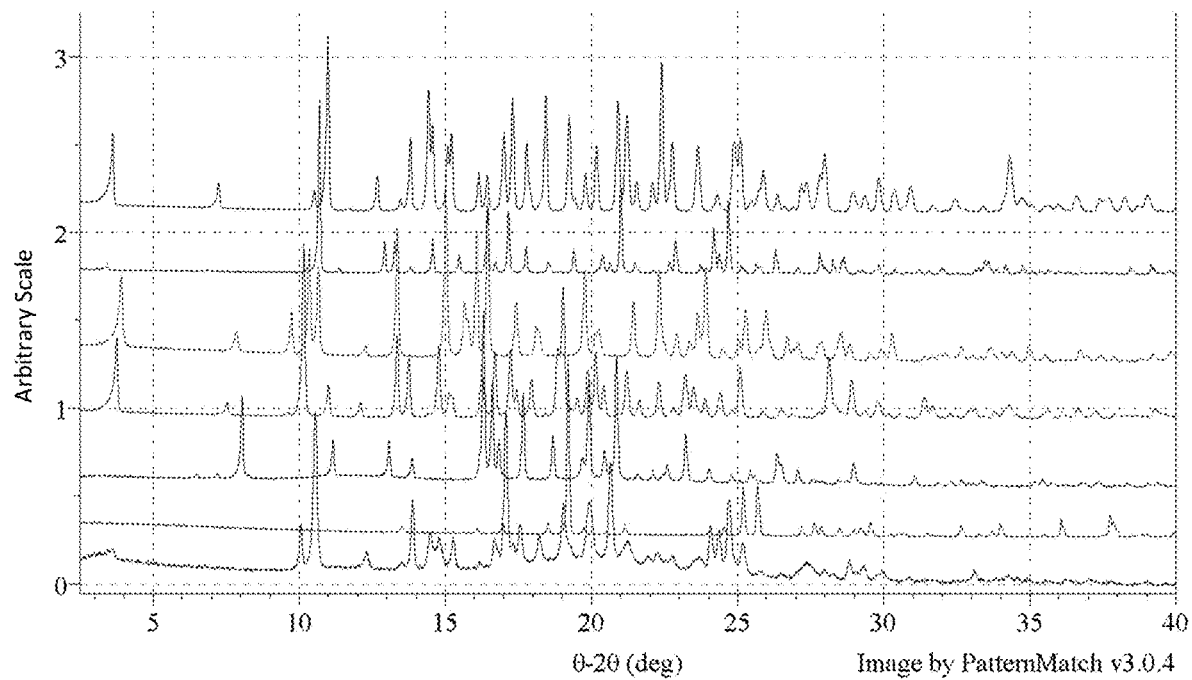
FIG. 6. XRPD patterns.

Polymorph Screening and Stability:

A polymorph screening study was initiated to investigate the presence and identity of various solid materials that may be possible for Alpha-1062 Gluconate. This study used lot CA19-1144 as the starting material and utilized various solvent systems and conditions to isolate and study the materials produced during the studies (Table 5). The various materials were analyzed by XRPD and the various solid forms identified as shown (FIG. 6).

To investigate the stability of the four pure crystalline forms of Alpha-1062 Gluconate, water activity ($a_w$) slurries using a variety of mixed aqueous/organic solvent systems (Table 6) along with relative humidity stressing (Table 7) were used to define the regions of stability for the given hydrates of Alpha-1062 Gluconate. Slurries of each sample in each solvent system were studied for a period of time to determine the interconversion to the most stable form.

From these studies Form A (anhydrate) was found to be the most stable Form at low water activities of less than about 0.12 $a_w$ (12% RH). Above this water activity, up to about 0.5 $a_w$, Form A Anhydrate converts to Form C (Monohydrate) which appears to be the stable Form. Above 0.5 $a_w$, Form B (Tetrahydrate) is formed and is the most stable Form. Form D (Dihydrate) was only observed from exposure at about 75% RH or by drying. Form D does not appear stable at any of the conditions evaluated and readily converts to other dependent Forms dependent upon the storage humidity.

Characterization of the Materials:

Form A: Alpha-1062 Gluconate, lot CA19-1144 (Table 2). Form A is an anhydrous material. Form A was found to undergo conversion to hydrated forms in solvent systems with a water activity above 0.12 $a_w$ (12% RH). Regardless, Form A appears kinetically stable in the solid state at 43% RH (RT) and was sustained up to 5 days at that condition.

Figure 7:
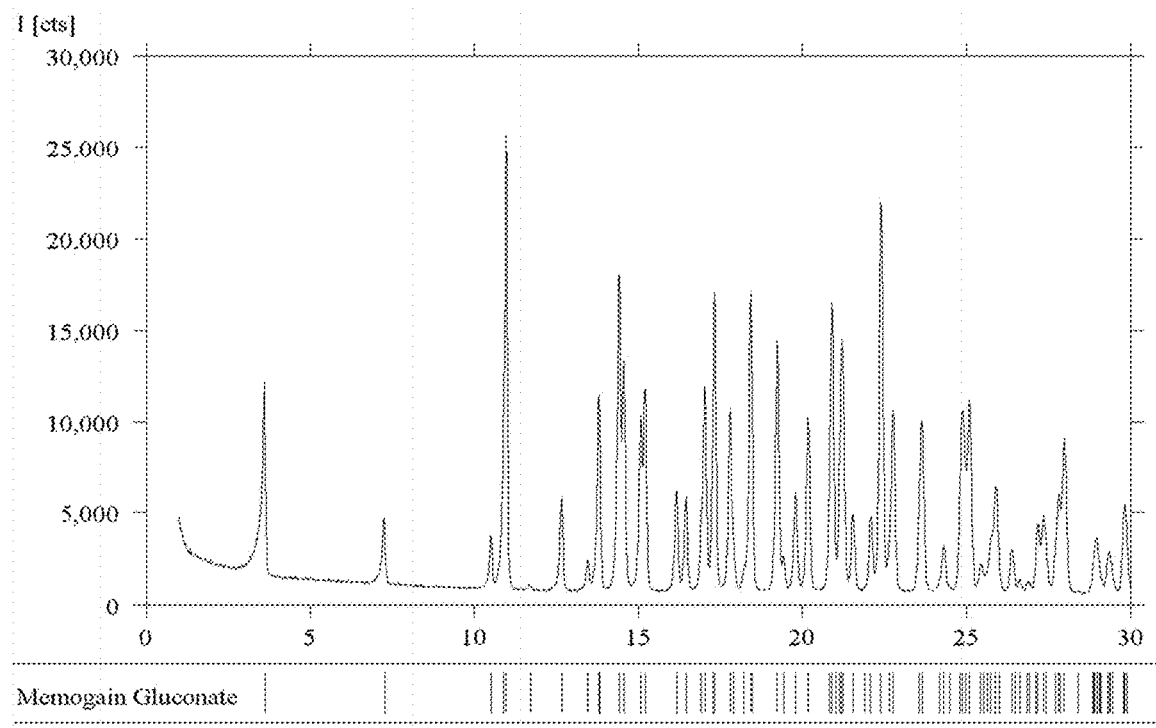
FIG. 7. Tentative indexing solution of Form A: Alpha-1062 Gluconate, lot CA19-1144.

XRPD (FIG. 7). The X-ray powder diffraction pattern of Form A was successfully indexed by a single primitive orthorhombic unit cell and provides a robust description of the crystalline form through tentative crystallographic unit cell parameters and strong evidence that the pattern is representative of a single crystalline phase. The formula unit volume of 688 Å$^3$ calculated from the indexing results generates a calculated density of 1.419 g/cm$^3$. Sugars are known to pack densely due to a large number of hydrogen bonding.

Tabulation of the XRPD pattern (FIG. 8) for Form A lists the observed peak positions and intensities with the most prominent peaks shaded for emphasis. Due to the plate-like nature of the material, the use of a zero background mount in reflectance mode results in the presence of preferred orientation in Form A (FIG. 9) relative to a transmission mode pattern.

Solution NMR spectrum is consistent with the chemical structure and contains 1 mol/mol of gluconic acid, consistent with a 1:1 stoichiometric salt.

Figure 10:
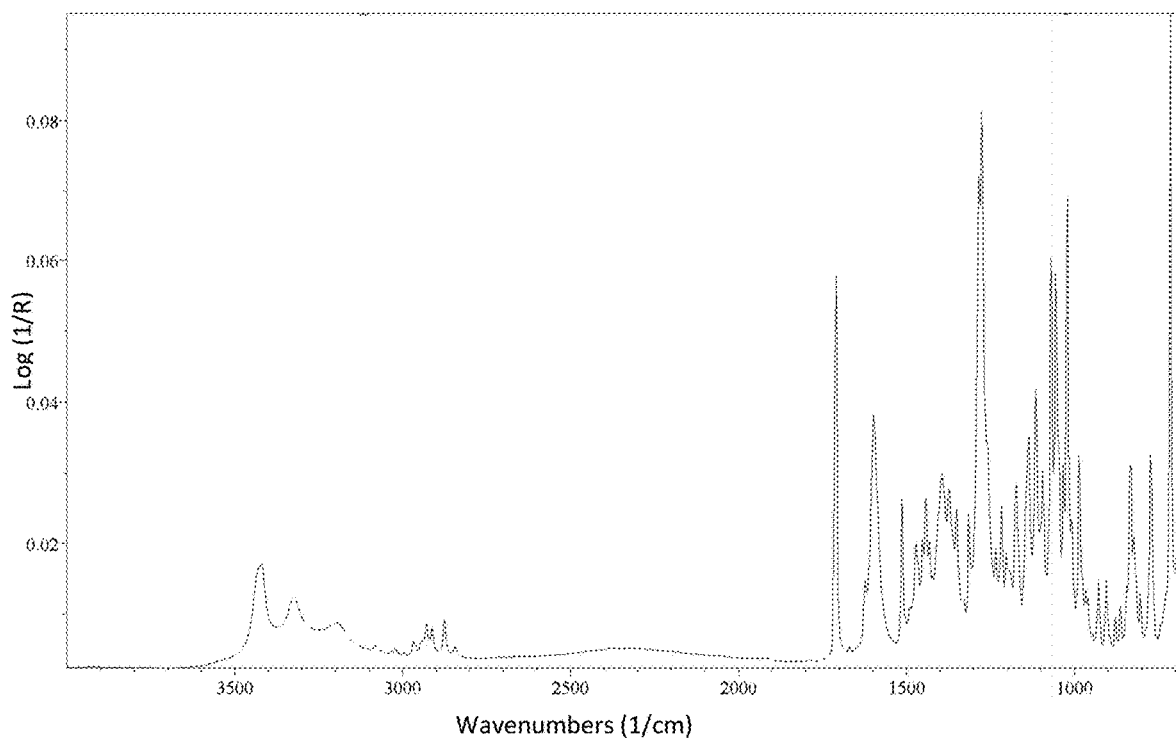
FIG. 10. ATR FTIR Spectrum of Form A: Alpha-1062 Gluconate, lot 2455 RD-00017-002.

FTIR spectral analysis using an ATR collection mode for sample 2455_RD-00017-002 generates an FTIR spectrum (FIG. 10) consistent with the structure of anhydrous Form A Alpha-1062 Gluconate.

Figure 11:
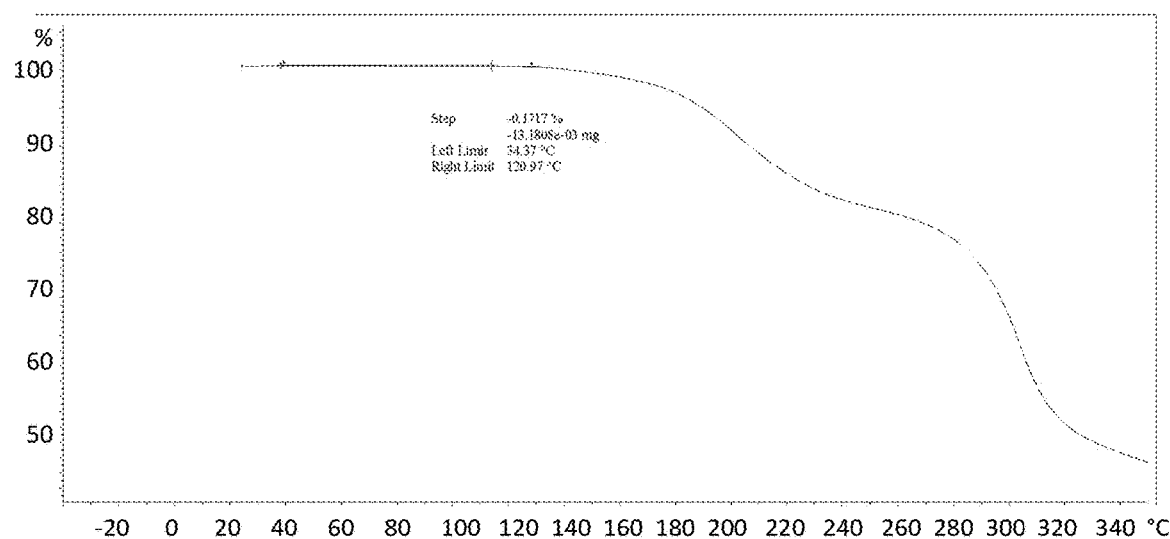
FIG. 11. Thermograms of Form A: Alpha-1062 Gluconate, lot CA19-1144.
Figure 11:
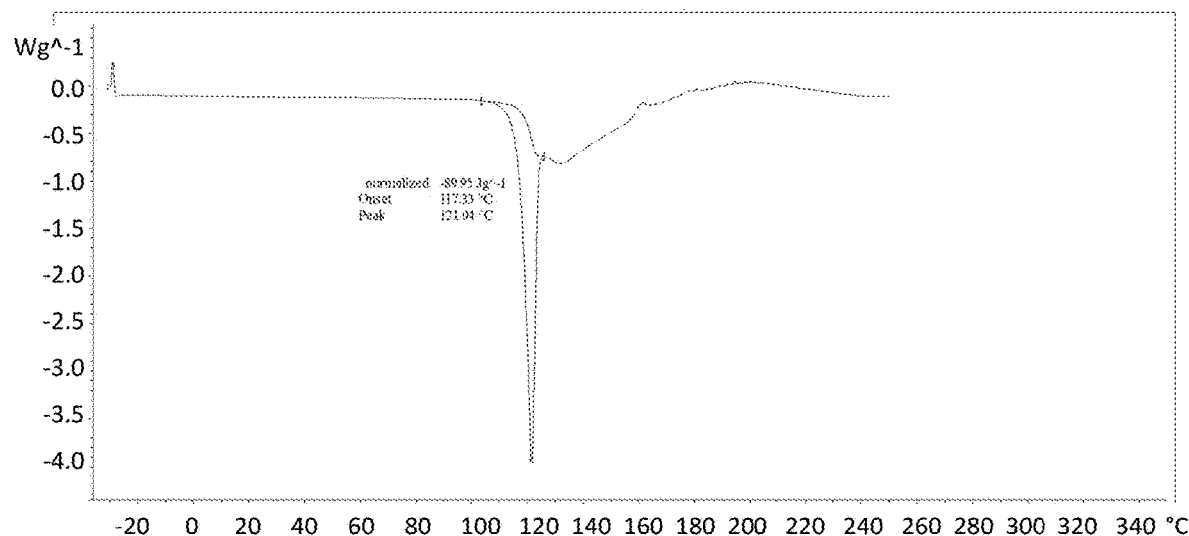

Thermal Analyses (FIG. 11). The TGA thermogram exhibits a 0.17% weight loss up to 121° C. A single endotherm with an onset of 117° C. is observed in the DSC consistent with a melt. Based on the observed weight loss after the melt, decomposition is likely. Heating material to just beyond the melt (125° C.) and subsequent cooling resulted in an amorphous material.

Figure 12:
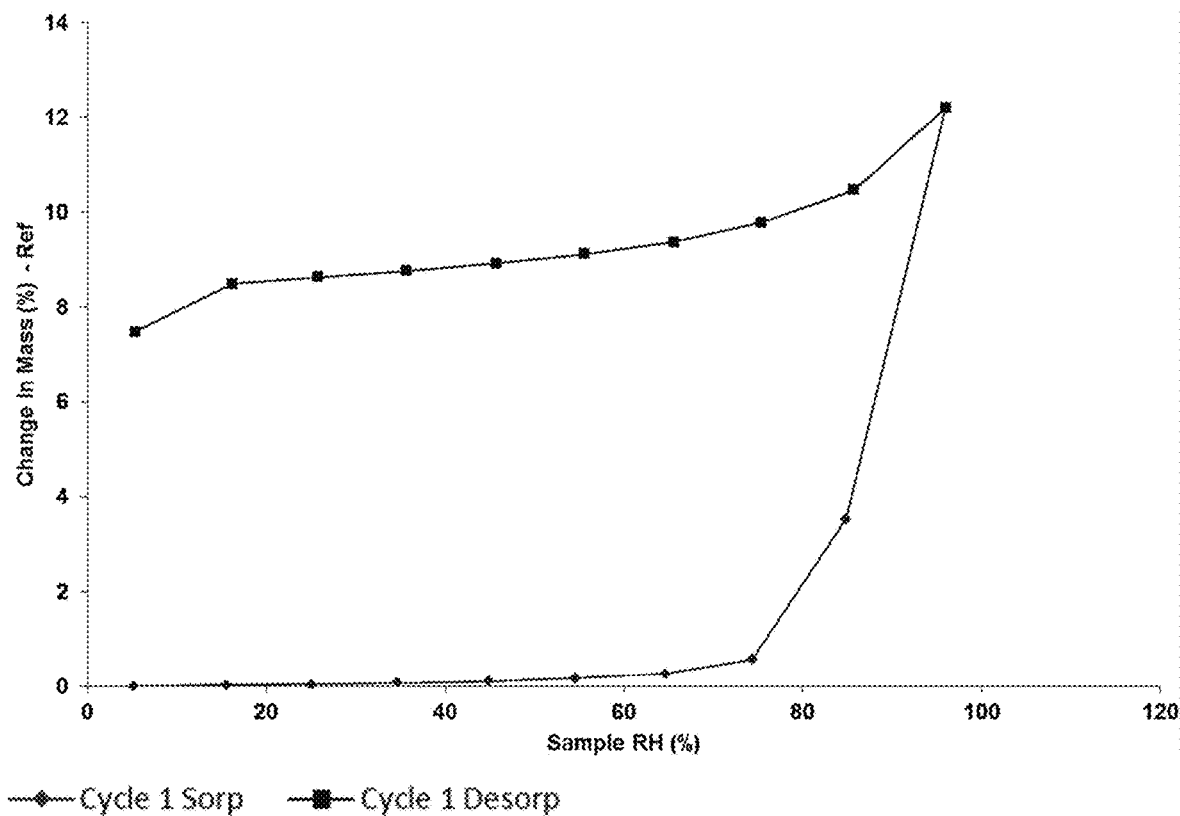
FIG. 12. DVS isotherm of Form A: Alpha-1062 Gluconate, lot CA19-1144.

The dynamic vapor sorption (DVS) isotherm (FIG. 12) indicates Form A exhibits significant hygroscopicity above 75% RH. A 0.57% weight gain was observed from 5 to 75% RH. Weight significantly increased above 75% RH with 2.97% weight gained from 75 to 85% RH and an additional 8.7% weight gained from 85 to 95% RH. Hysteresis was observed on desorption with a stable plateau achieved, suggesting the material likely converted to a hydrated form. The weight achieved within the stable plateau is consistent with the gain of more than 3 mol/mol water and suggests that Form A converted to Form B when above 85% RH. The material recovered from the DVS experiment was identified as Form A+minor peaks of Form B; however, it should be noted that the material was held at 5% RH once the DVS experiment was completed and likely partially dehydrated back to Form A before recovery and testing was performed.

Solubility Studies (Table 9) were performed on Form A in various solvents and the results are tabulated showing high aqueous solubility.

Form B: Alpha-1062 Gluconate, Sample 8235-82-08 (Table 10). Form B is a tetrahydrate crystalline lattice. It appears that at least one of the four water sites in the crystal lattice is somewhat labile. DVS data suggests that Form B can contain approximately 3.6 to 3.9 mol/mol of water in the relative humidity range between 15 and 85% RH. Form B was observed in solvent systems with water activity above 0.52 $a_w$ (52% RH) and in equilibrium with Form C below 0.52 and above 0.31 $a_w$ (31% RH).

Figure 13:
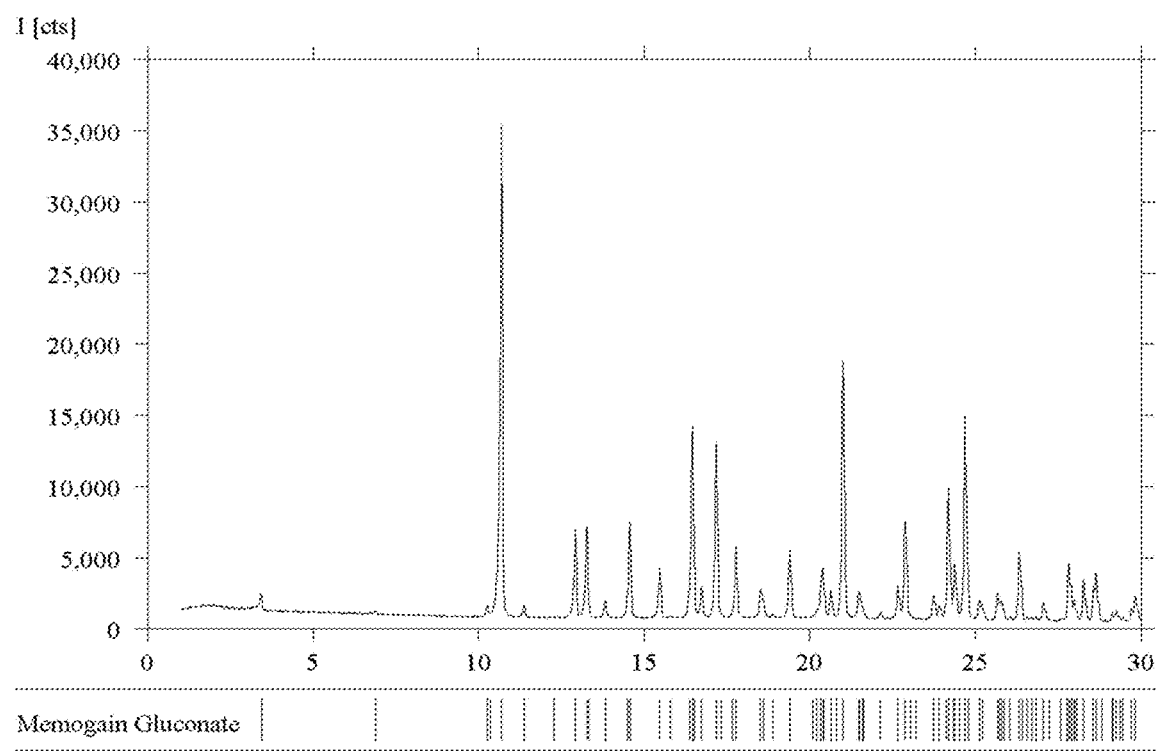
FIG. 13. Tentative indexing solution of Form B: Alpha-1062 Gluconate, sample 8235-85-01.

XRPD (FIG. 13). The XRPD pattern was successfully indexed by a single primitive orthorhombic unit cell. The formula unit volume of 772 Å$^3$ calculated from the indexing results is larger than Form A by 84 Å$^3$. The excess volume, relative to Form A, is sufficient to accommodate up to 4 mol/mol of water and generates a calculated density of 1.420 g/cm$^3$.

Figure 14:
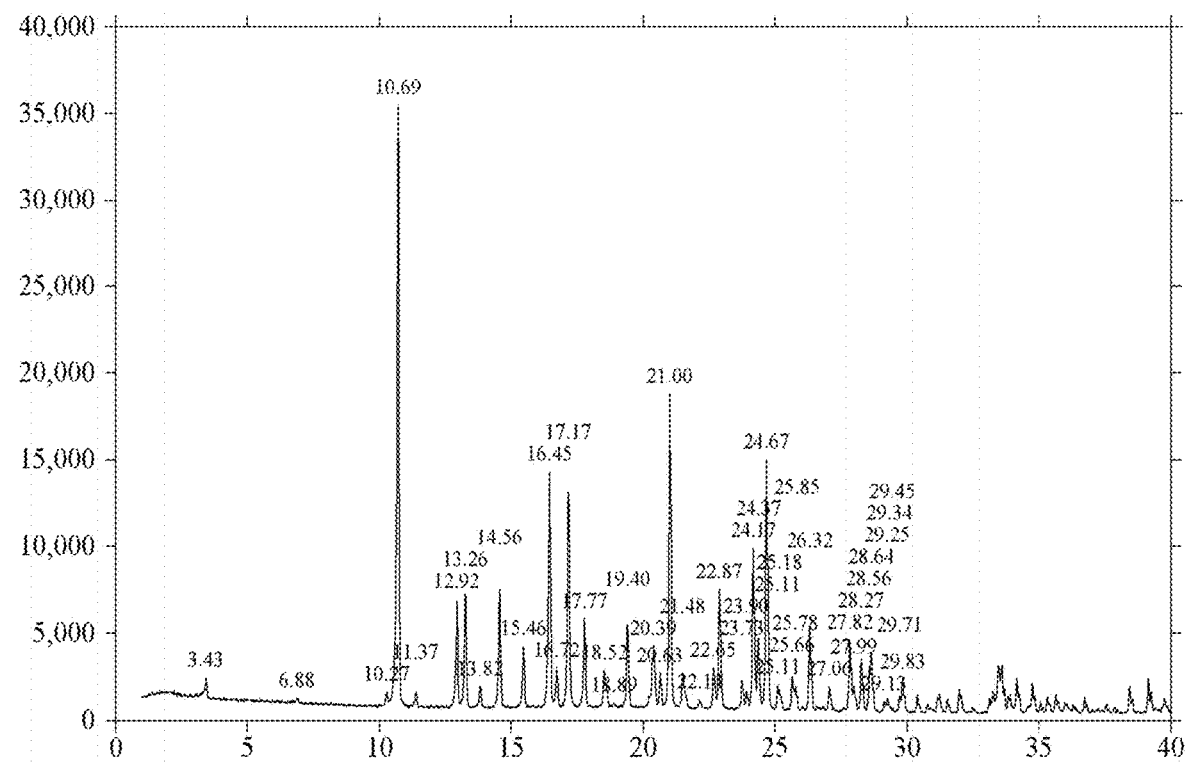
FIG. 14. Observed XRPD peaks of Form B: Alpha-1062 Gluconate, sample 8235-85-01.

Tabulation of the XRPD pattern (FIG. 14) for Form B lists the observed peak positions and intensities with the most prominent peaks shaded for emphasis.

Form B (sample 8296-34-01) was held at 57% RH for four days and analyzed by XRPD and coulometric Karl Fischer (KF) titration. The resulting sample remained Form B and contained 10.2% water (equivalent to ~3.7 mol/mol of water) and is consistent with the indexing results.

Solution NMR spectrum is consistent with the chemical structure and contains 1 mol/mol of gluconic acid, consistent a 1:1 stoichiometric salt; residual organic solvents (such as MEK) were not observed.

Figure 15:
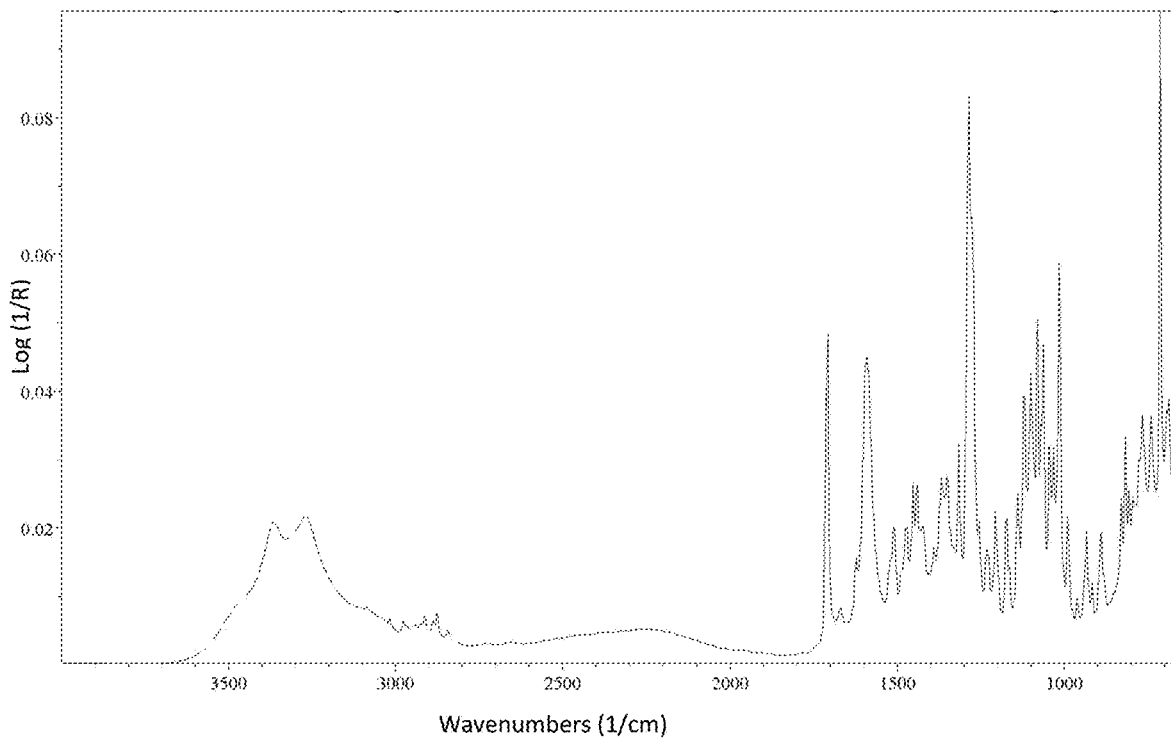
FIG. 15. ATR FTIR Spectrum of Form B: Alpha-1062 Gluconate, sample 8296-41-01.

FTIR spectral analysis using an ATR collection mode for sample 8296-41-01 generates an FTIR spectrum (FIG. 15) consistent with the structure of Form B Alpha-1062 Gluconate.

Figure 16:
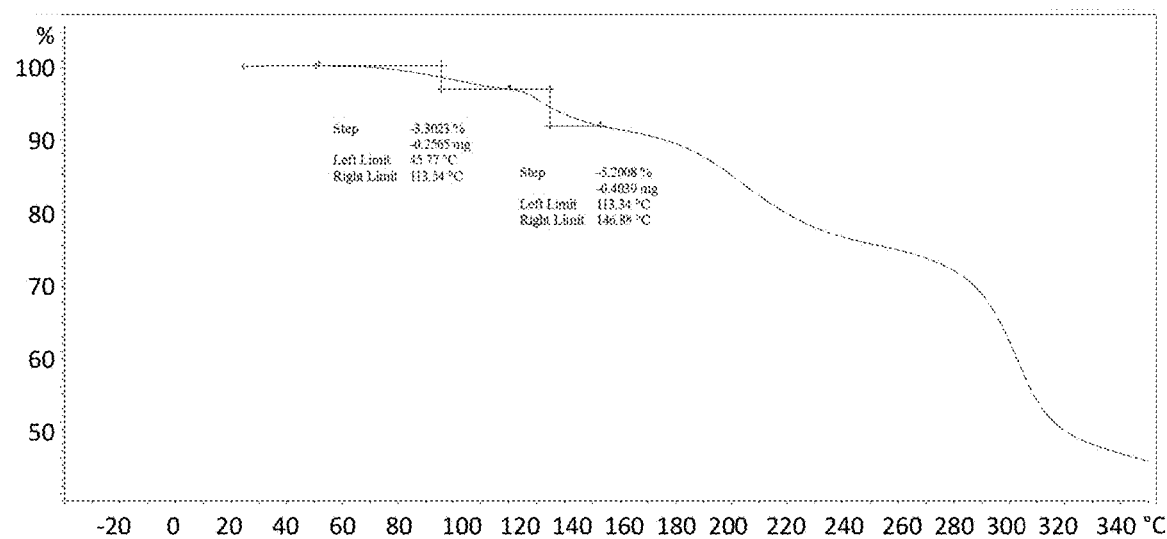
FIG. 16. Thermograms of Form B: Alpha-1062 Gluconate, sample 8235-82-08.
Figure 16:
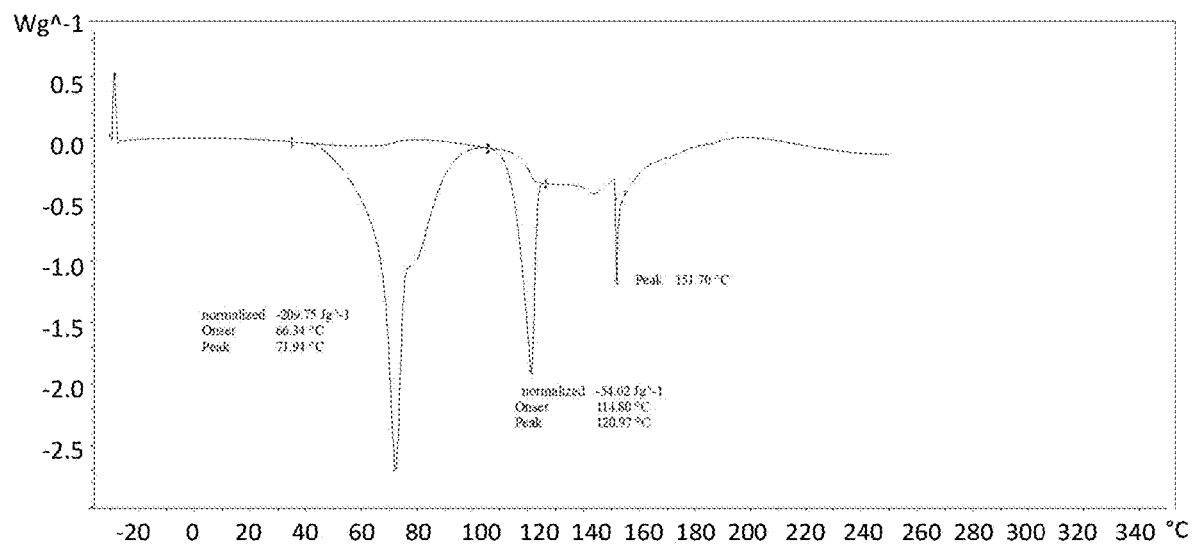

Thermal Analyses (FIG. 16). The TGA thermogram exhibits a 3.3% weight loss up to 114° C. and an additional 5.2% up to 147° C. A broad endotherm with an onset of 66° C. (concurrent with weight loss in the TGA) is observed in the DSC consistent with desolvation. A second endotherm with an onset of 115° C. is observed followed by a weak endotherm at 152° C.

Heating of a sample of Form B at 40-75° C. over 10 minutes was analyzed by XRPD and resulted in partial dehydration and conversion to a mixture of Forms D and C (both purported hydrates, but each at a lower hydration state) and an additional peak.

Form B was shown to dehydrate to Form A at 0% RH after 1 day (Table 7).

Figure 17:
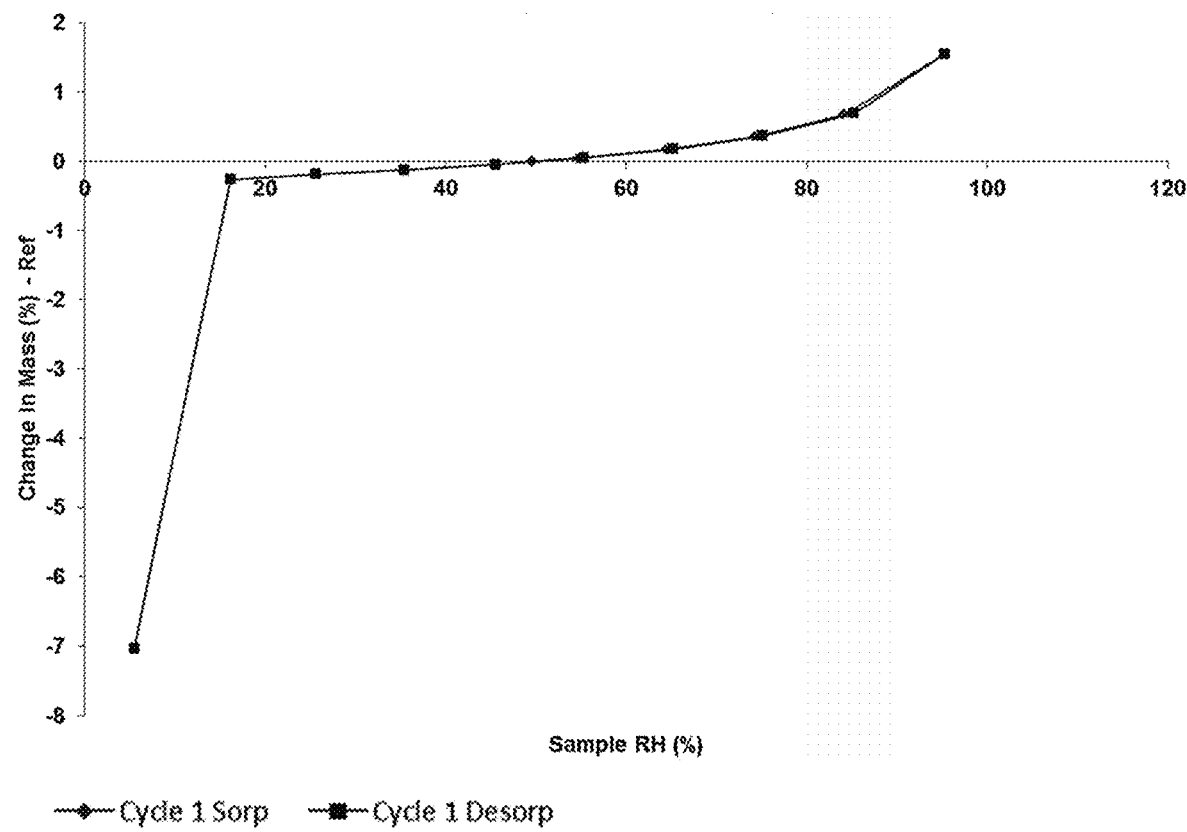
FIG. 17. DVS isotherm of Form B: Alpha-1062 Gluconate, sample 8235-82-08.
Figure 18:
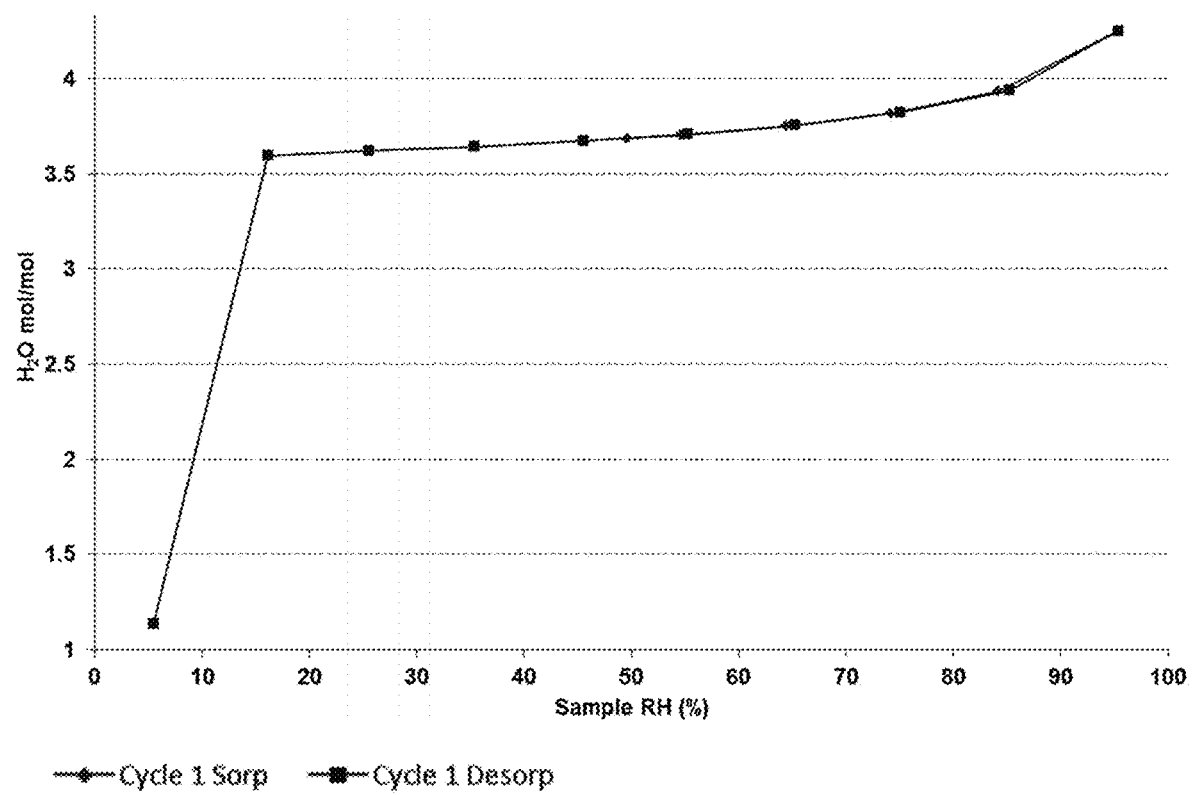
FIG. 18. DVS isotherm of Form B: Alpha-1062 Gluconate, sample 8235-82-08, corrected for water content.

The dynamic vapor sorption (DVS) isotherm (FIG. 17) was collected starting at 50% RH (to avoid conversion from loss of hydration prior to data acquisition). Form B exhibits limited hygroscopicity; with a 1.5% weight gain from 50-95% RH. Upon desorption, 1.8% weight loss from 95-15% RH followed by 6.8% weight loss from 15-5% RH was observed. The DVS data was corrected for water content measured by KF at 57% RH (FIG. 18). A stable plateau of between 3.6 and 3.9 mol/mol of water for Form B is evident between 15 and 85% RH. The material recovered from the DVS experiment was identified as anhydrous Form A.

Form C: Alpha-1062 Gluconate, Sample 8235-87-02 (Table 11). Form C was determined to be a monohydrate crystal lattice occupied at only about 0.4 to 0.5 mol/mol of water. Form C was observed in solvent systems with a water activity between 0.12 and 0.31 $a_w$ (12 and 31% RH) and in equilibrium with Form B above 0.31 and below 0.52 $a_w$ (52% RH).

Figure 19:
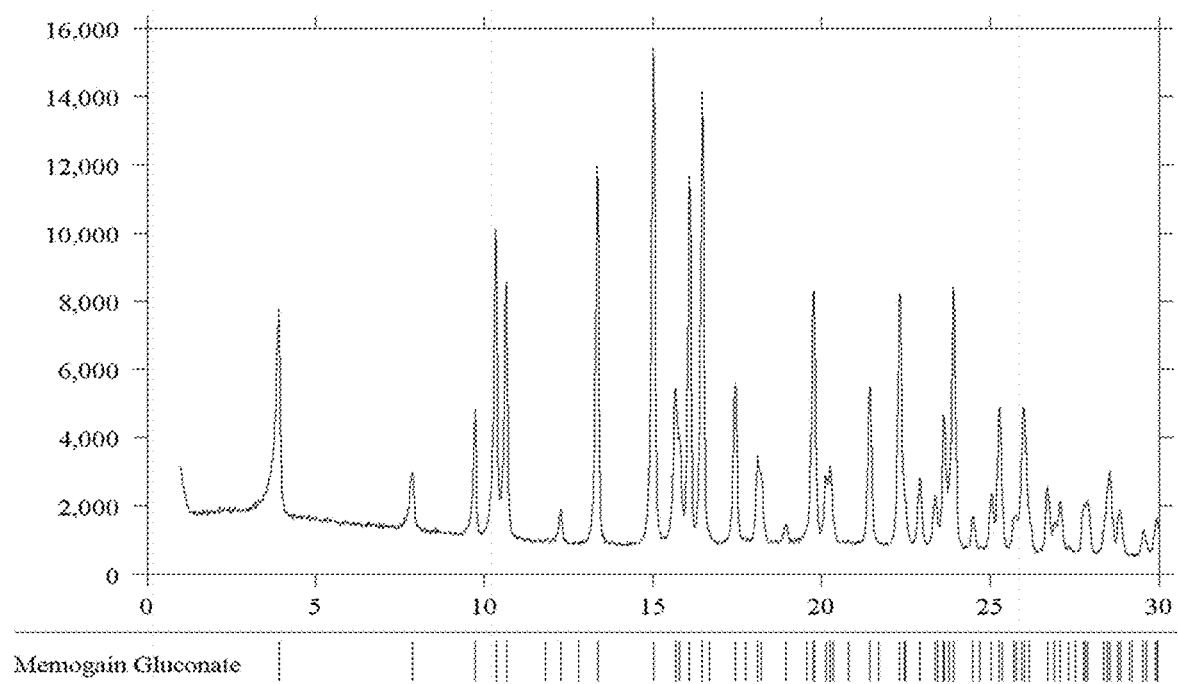
FIG. 19. Tentative indexing solution of Form C: Alpha-1062 Gluconate, sample 8235-87-02.

XRPD (FIG. 19). The XRPD pattern was successfully indexed by a single primitive monoclinic unit cell. The formula unit volume of 706 Å$^3$ calculated from the indexing results is larger than Form A by 18 Å$^3$. The excess volume, relative to Form A, is sufficient to accommodate up to 1 mol/mol of water and generates a calculated density of 1.425 g/cm$^3$.

Figure 20:
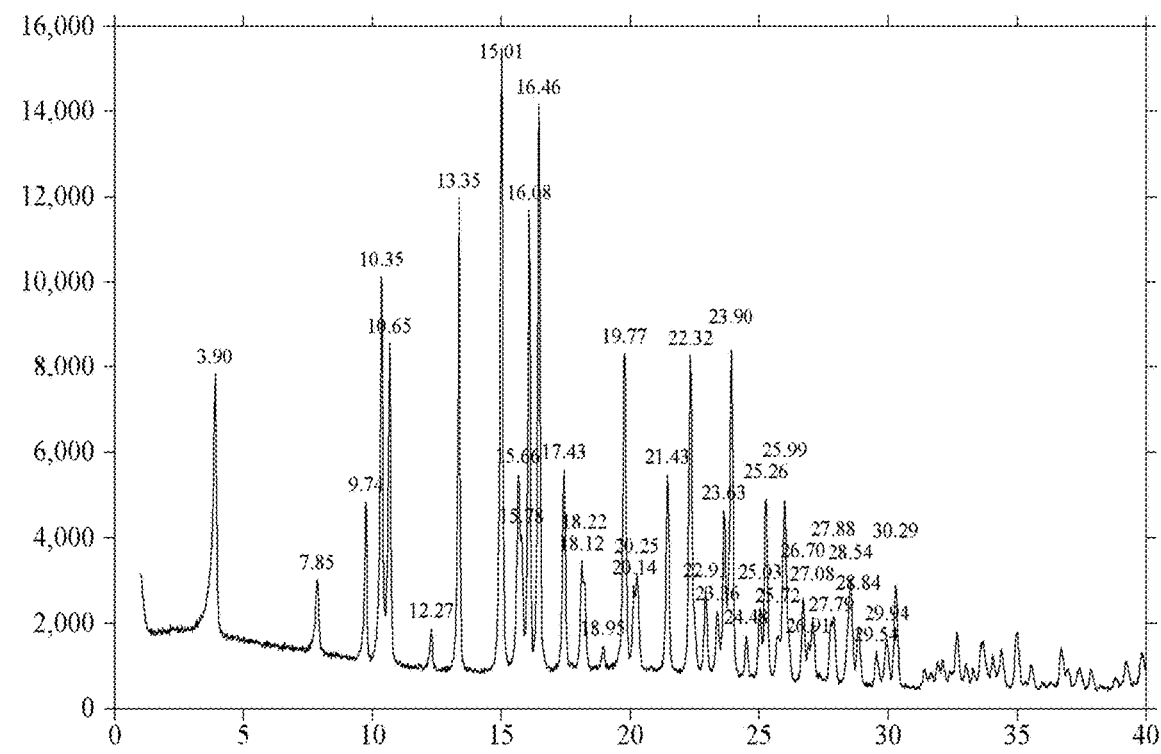
FIG. 20. Observed XRPD peaks of Form C: Alpha-1062 Gluconate, sample 8235-87-02.

Tabulation of the XRPD pattern (FIG. 20) for Form C lists the observed peak positions and intensities with the most prominent peaks shaded for emphasis.

Form C (sample 8296-34-02) was held at 11% RH for four days and analyzed by XRPD and coulometric Karl Fischer (KF) titration. The resulting sample remained Form C and contained 1.3% water (equivalent to ~0.4 mol/mol of water).

Figure 21:
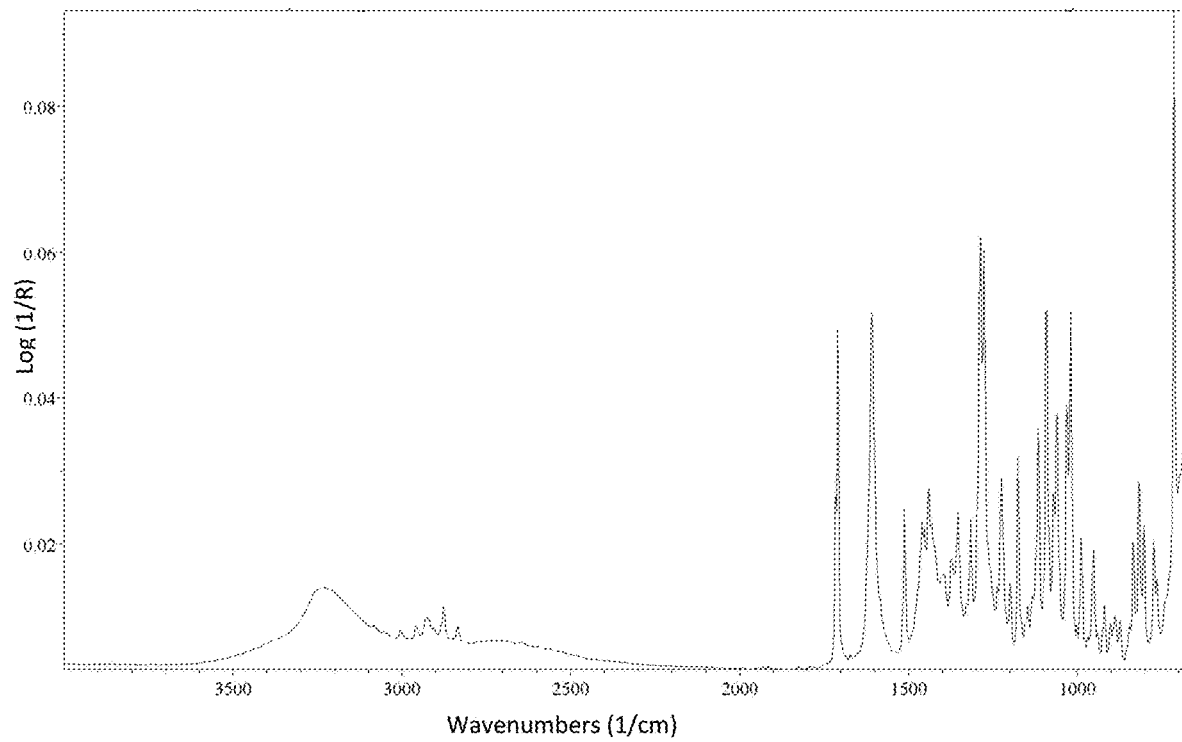
FIG. 21. ATR FTIR Spectrum of Form C: Alpha-1062 Gluconate, lot 2455 RD-00049-001.

FTIR spectral analysis using an ATR collection mode for sample 2455_RD-00049-001 generates an FTIR spectrum (FIG. 21) consistent with the structure of Form C Alpha-1062 Gluconate.

Figure 22:
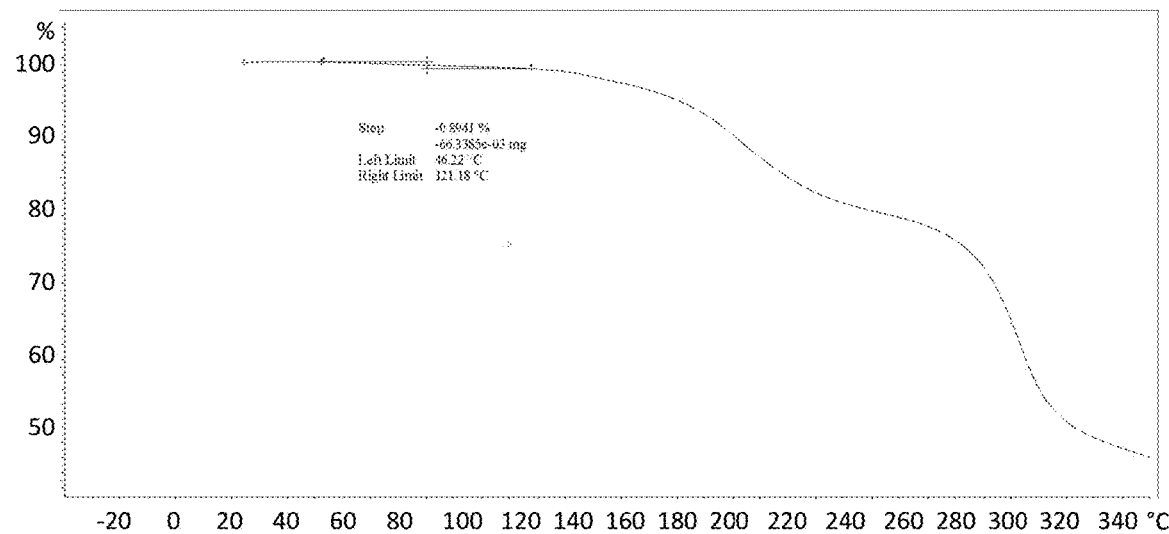
FIG. 22. Thermograms of Form C: Alpha-1062 Gluconate, sample 8235-87-02.
Figure 22:
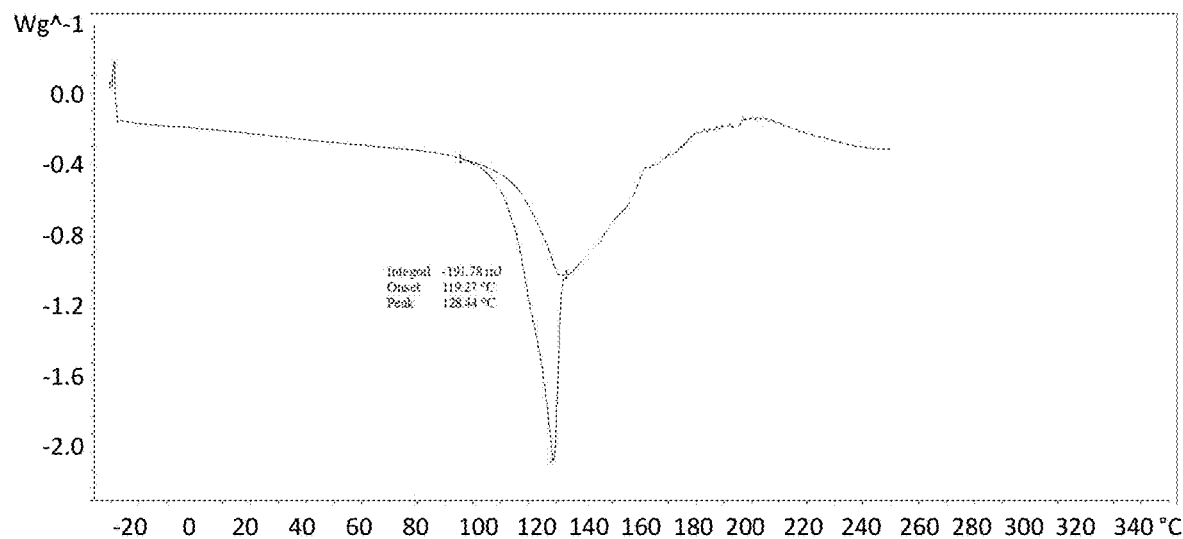

Thermal Analyses (FIG. 22). The TGA thermogram exhibits a 0.9% weight loss up to 121° C. An endotherm with an onset of 119° C. is observed in the DSC.

Figure 23:
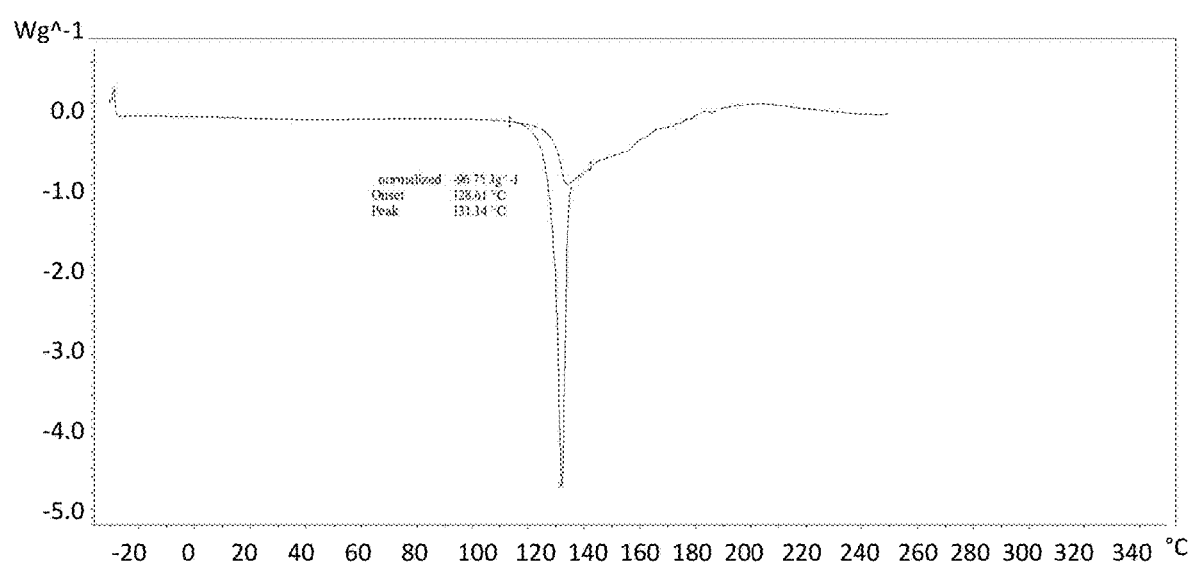
FIG. 23. DSC thermogram of Form C: Alpha-1062 Gluconate Form C, sample 8296-08-01.

Form C (sample 8235-92-04) was held at 11% RH for seven days and analyzed by XRPD and DSC for comparison (sample 8296-08-01). The resulting sample remained Form C and a single sharp endotherm with an onset of 129° C. is observed in the DSC (FIG. 23).

Form C (sample 8235-93-02) was stored at 45° C. under a vacuum for three hours and was analyzed by XRPD. The resulting sample remained Form C with the presence of a minor amount of Form A.

Figure 24:
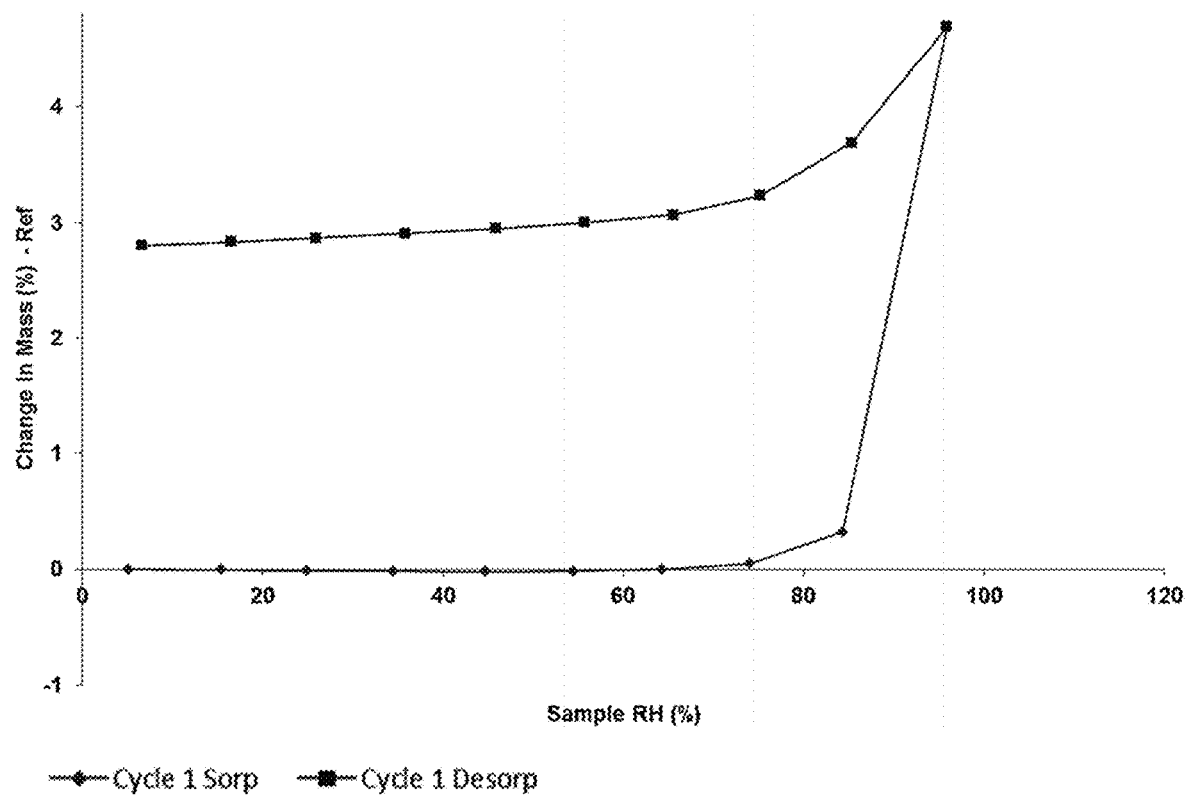
FIG. 24. DVS data of Form C: Alpha-1062 Gluconate, sample 8235-92-11.
Figure 25:
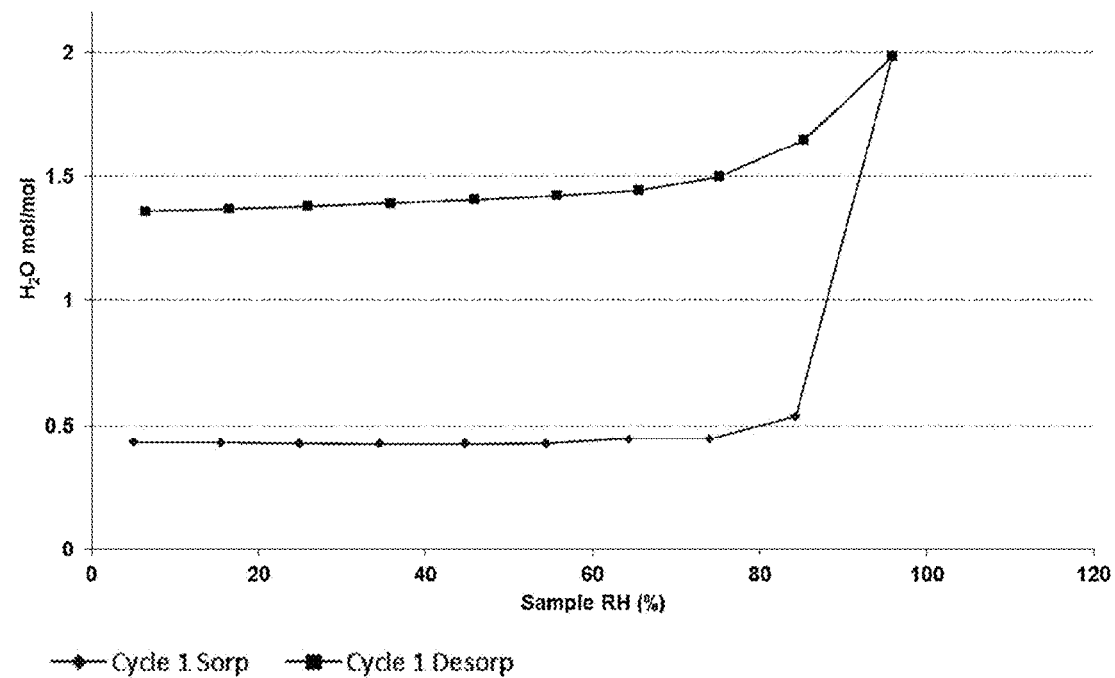
FIG. 25. DVS isotherm of Form C: Alpha-1062 Gluconate, sample 8235-92-11, corrected for water content.

The dynamic vapor sorption (DVS) isotherm (FIG. 24, sample 8235-92-11) indicates that Form C exhibits significant hygroscopicity above 75% RH. The sample exhibited no significant weight gain from 5-75% RH but 4.6% weight gain was observed from 75-95%. Upon desorption, a 1.5% weight loss is observed from 95-75% RH. The DVS data was corrected for water content measured by KF at 11% RH (FIG. 25). The sample retained ~1.4 mol/mol water. The material recovered from the DVS experiment was identified by XRPD as a mixture of Forms C and B.

Form D: Alpha-1062 Gluconate, Sample 8235-86-01 (Table 12). Form D was determined to be a dihydrate crystal lattice that is not thermodynamically stable and will eventually convert to other more stable hydrates with time, dependent upon the RH conditions. Form D is formed by the exposure of Form A at about 75% RH. Attempts to generate pure Form D as a single crystalline phase resulted in mixtures contaminated with minor amounts of either Form A or Form B.

Figure 26:
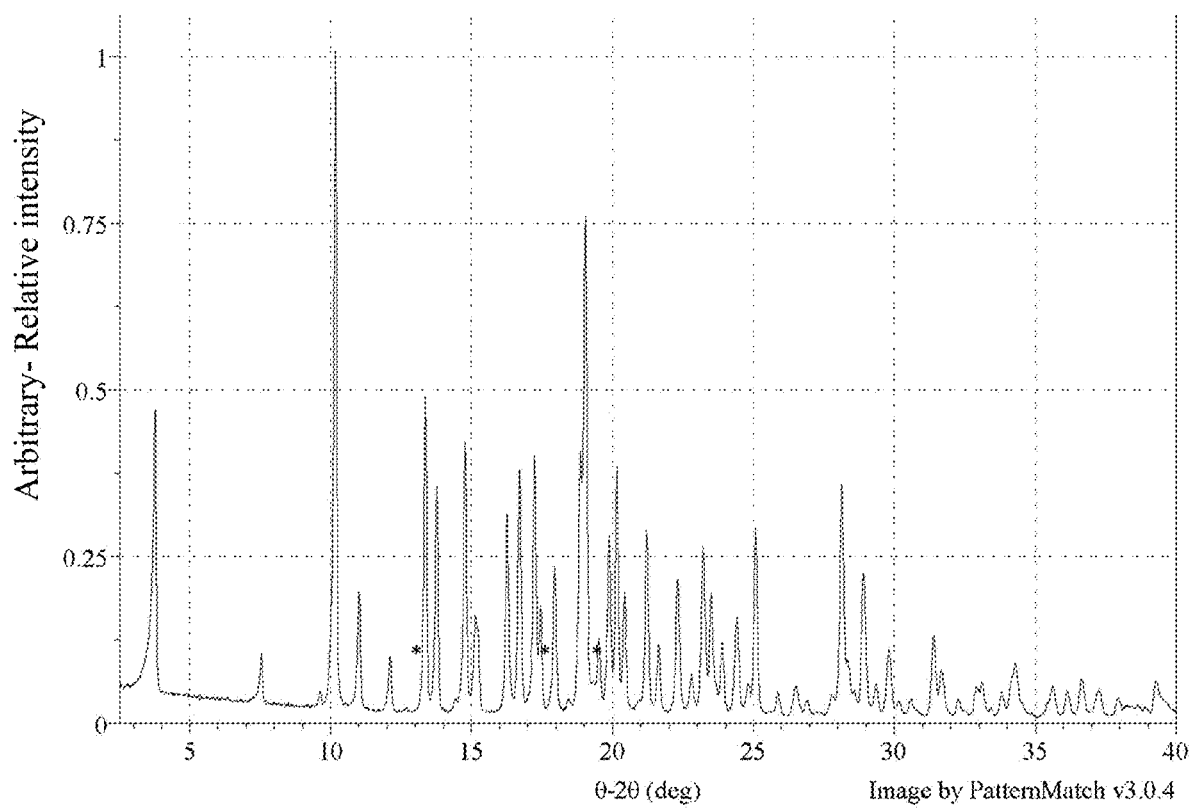
FIG. 26. XRPD pattern of Form D: Alpha-1062 Gluconate, sample 8235-86-01.
Figure 27:
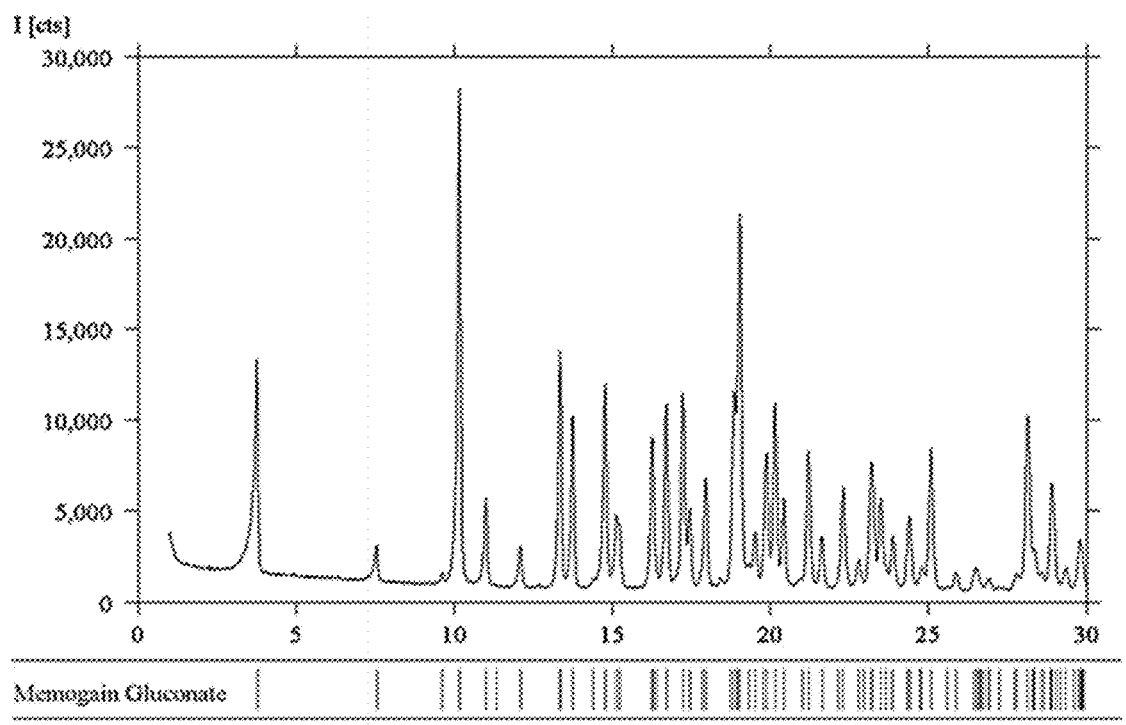
FIG. 27. Tentative indexing solution of Form D: Alpha-1062 Gluconate, sample 8235-86-01.

XRPD (FIGS. 26-27). The XRPD pattern represents a mixture of Form D and minor peaks of Form A. Small peaks near 12.68, 18.43, and 20.91° (2θ) are consistent with Form A and were purposefully ignored during indexing. Form D was successfully indexed from the remaining peaks by a single primitive orthorhombic unit cell. The formula unit volume of 733 Å$^3$ calculated from the indexing results is larger than Form A by 45 Å$^3$. The excess volume, relative to Form A, is sufficient to accommodate up to 2 mol/mol of water and generates a calculated density of 1.413 g/cm$^3$.

Figure 28:
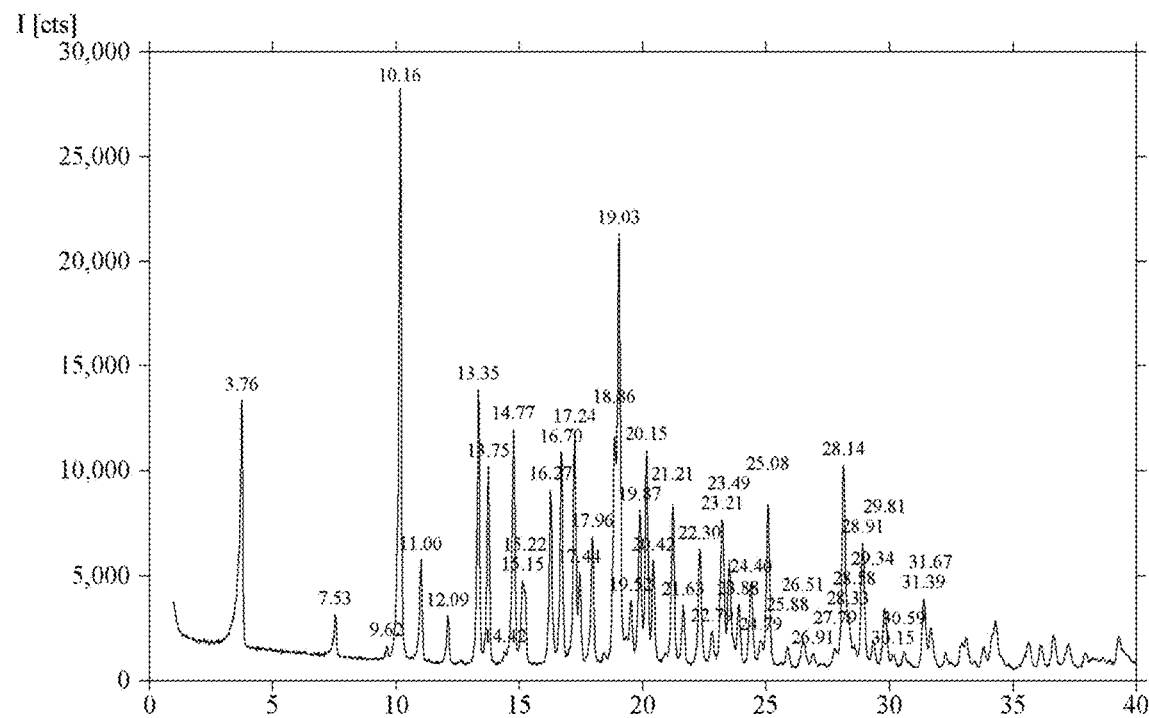
FIG. 28. Observed XRPD peaks of Form D: Alpha-1062 Gluconate, sample 8235-86-01.

Tabulation of the XRPD pattern (FIG. 28) for Form D lists the observed peak positions and intensities with the most prominent peaks shaded for emphasis.

Figure 29:
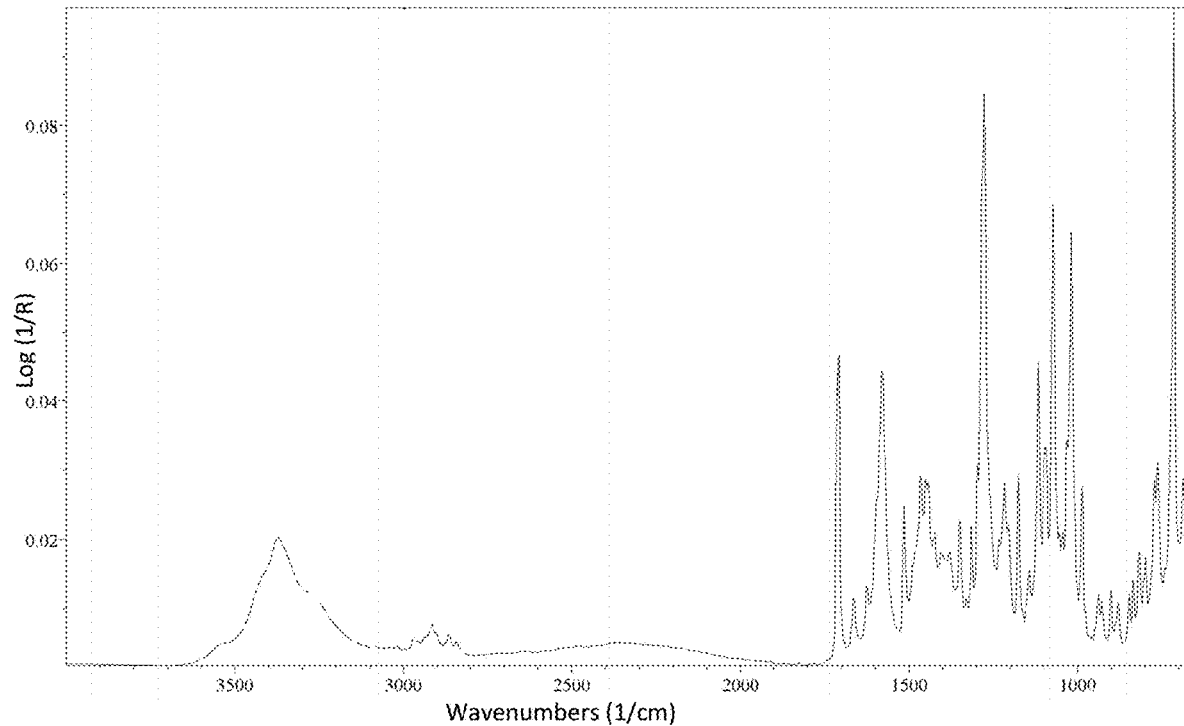
FIG. 29. ATR FTIR Spectrum of Form D: Alpha-1062 Gluconate, sample 8235-86-01.

FTIR spectral analysis using an ATR collection mode for sample 8235-86-01 generates an FTIR spectrum (FIG. 29) consistent with the structure of Form D Alpha-1062 Gluconate.

A sample of Form D and minor Form B (8235-34-03) was held at 75% RH for one day (to limit conversion) and analyzed by XRPD and Karl Fischer (KF) titration. The sample increased only slightly in Form B but, overall, remained similar to the initial composition. The sample contained 4.3% water or ~1.5 mol/mol of water.

Water activity slurries and relative humidity stressing studies (Tables 6-7) suggests that Form D is a metastable form at all conditions evaluated and eventually converts to Form B with extended exposure to relative humidity ≥52% RH or converts to Form C at relative humidity <52% RH.

Material E: Sample 8235-76-04 (Table 13). The material generated from evaporation of a Dichloromethane (DCM) solution is not consistent with Alpha-1062 Gluconate.

Figure 30:
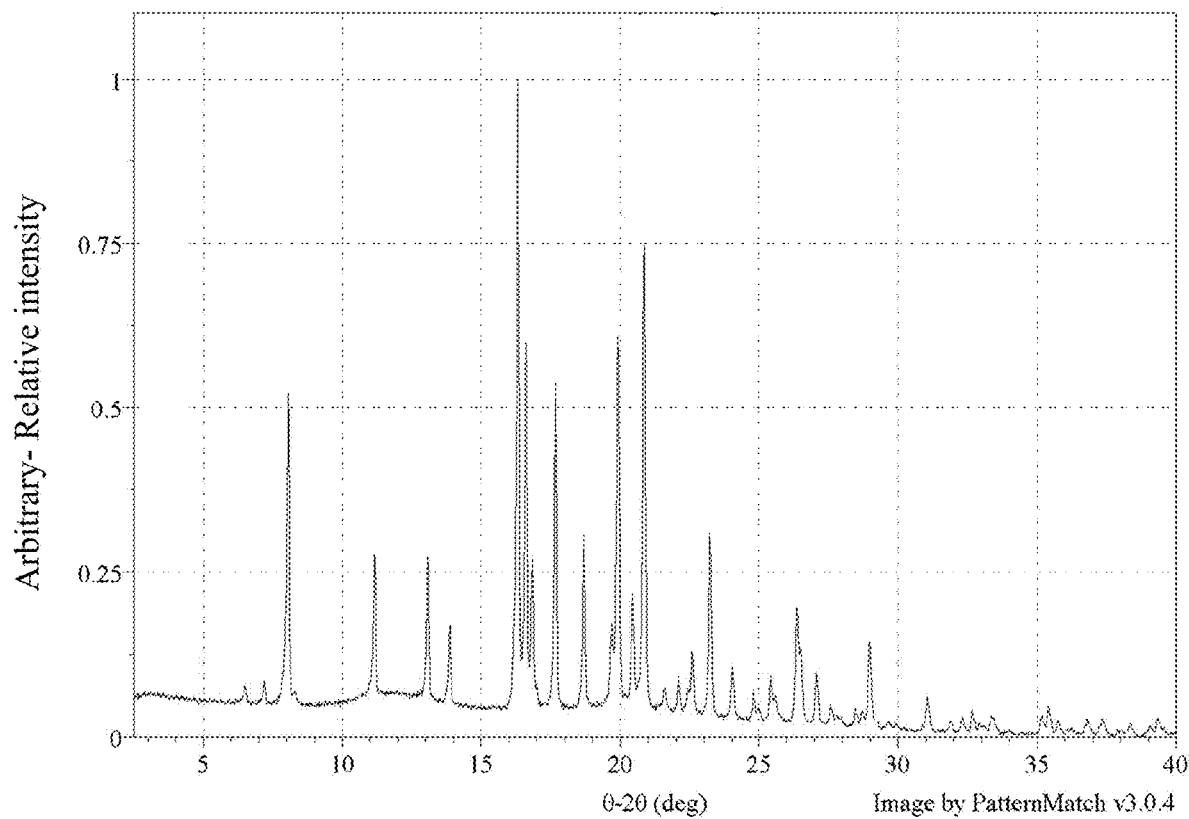
FIG. 30. XRPD pattern of Material E, sample 8235-76-04.

XRPD (FIG. 30). The XRPD pattern was indexed (not provided), but the volume is not sufficient to contain an Alpha-1062 Gluconate molecule suggesting this to be the free base or a decomposition product.

Solution NMR spectrum contains a non-stoichiometric amount of gluconate. Two molecular species are present in the spectrum. Also, 0.6 mol/mol of DCM is observed. The NMR spectrum is not consistent with the salt.

Figure 31:
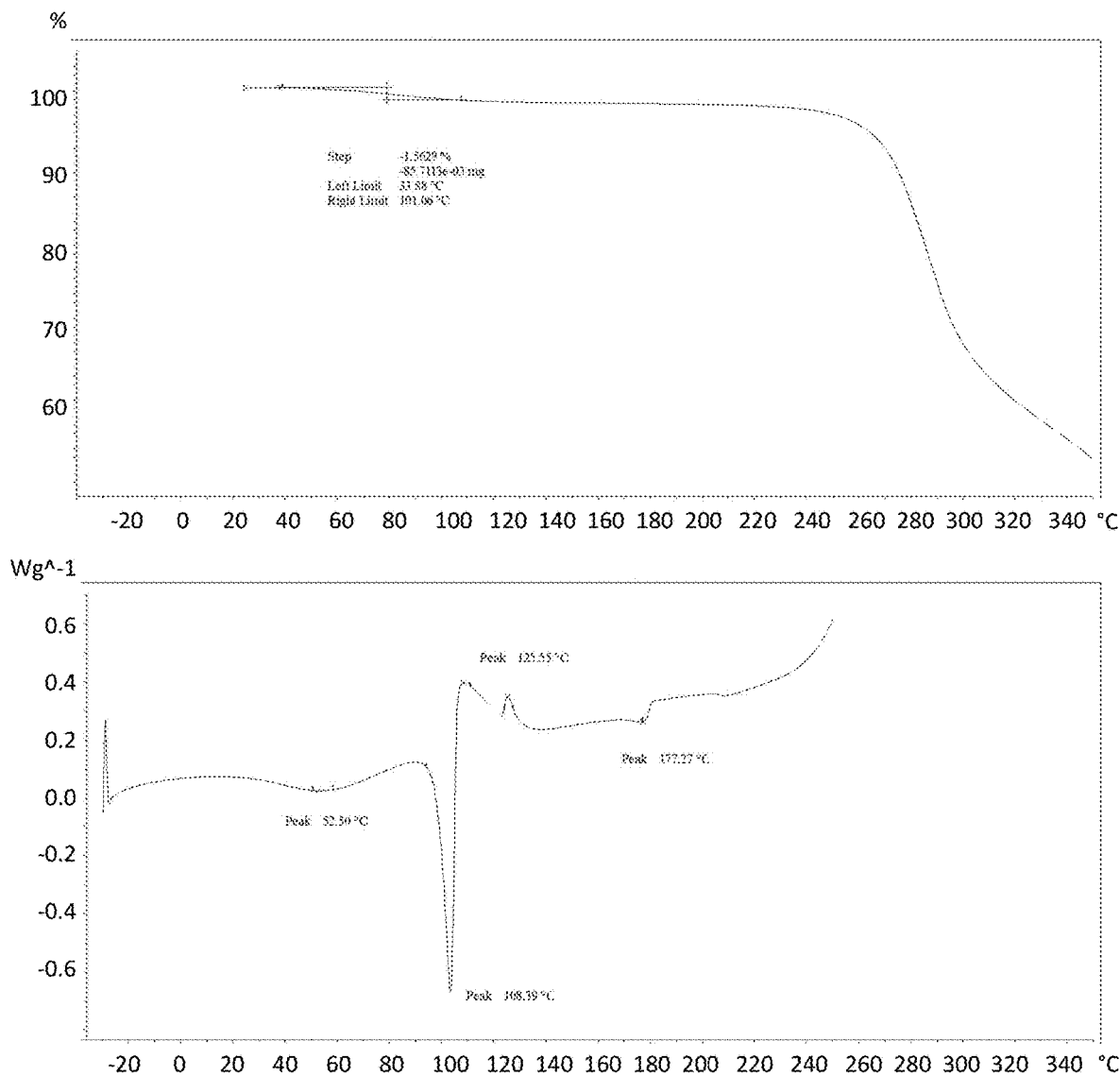
FIG. 31. Thermograms of Material E, sample 8235-76-04.

Thermal Analyses (FIG. 31). A 1.6% weight loss up to 101° C. was observed in the TGA. Multiple endothermic events are observed in the DSC.

Figure 32:
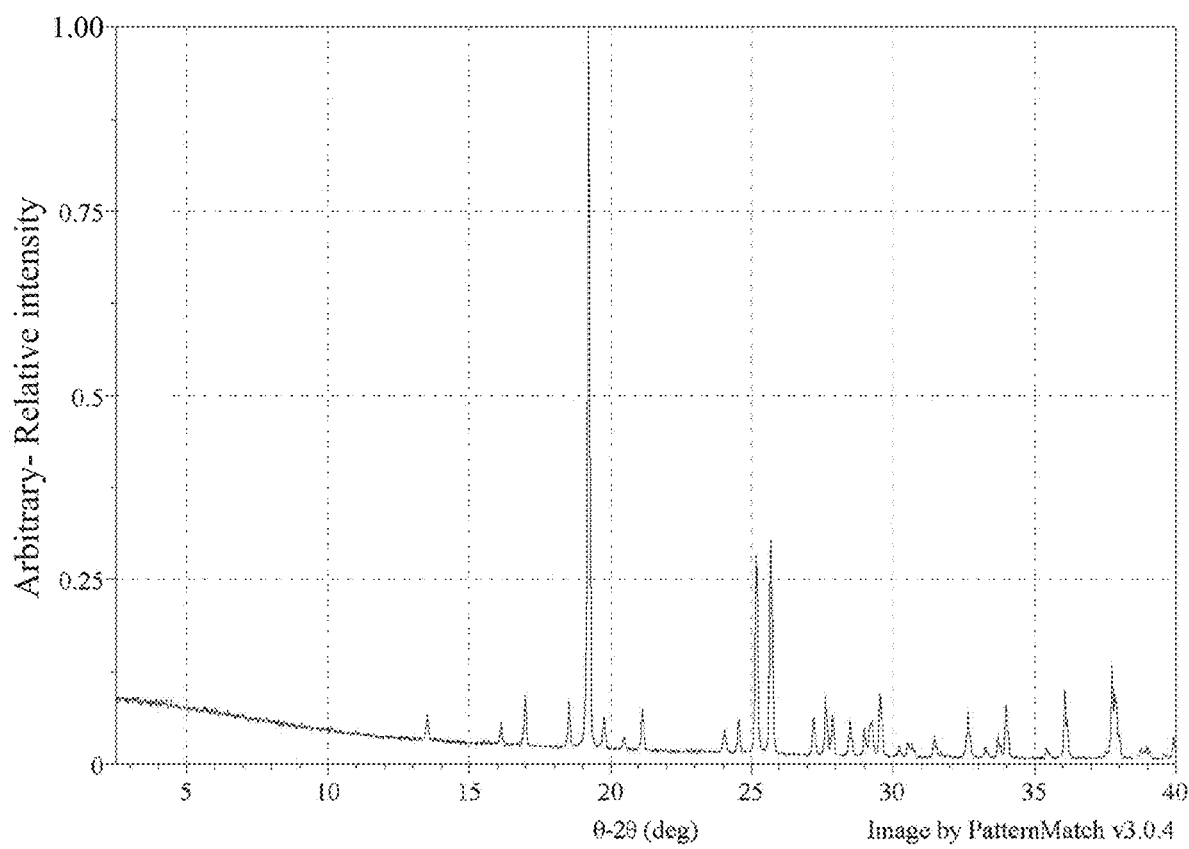
FIG. 32. XRPD pattern of Material F, sample 8235-76-07.

Material F: Sample 8235-76-07 (Table 14). A likely decomposition product generated from evaporation of a Dichloromethane (DCM) slurry.
  XRPD (FIG. 32). The XRPD pattern was indexed (not provided), but the volume is not sufficient to contain either Alpha-1062 free base or its salt suggesting this to be a simple Gluconate salt or a decomposition product.

Figure 33:
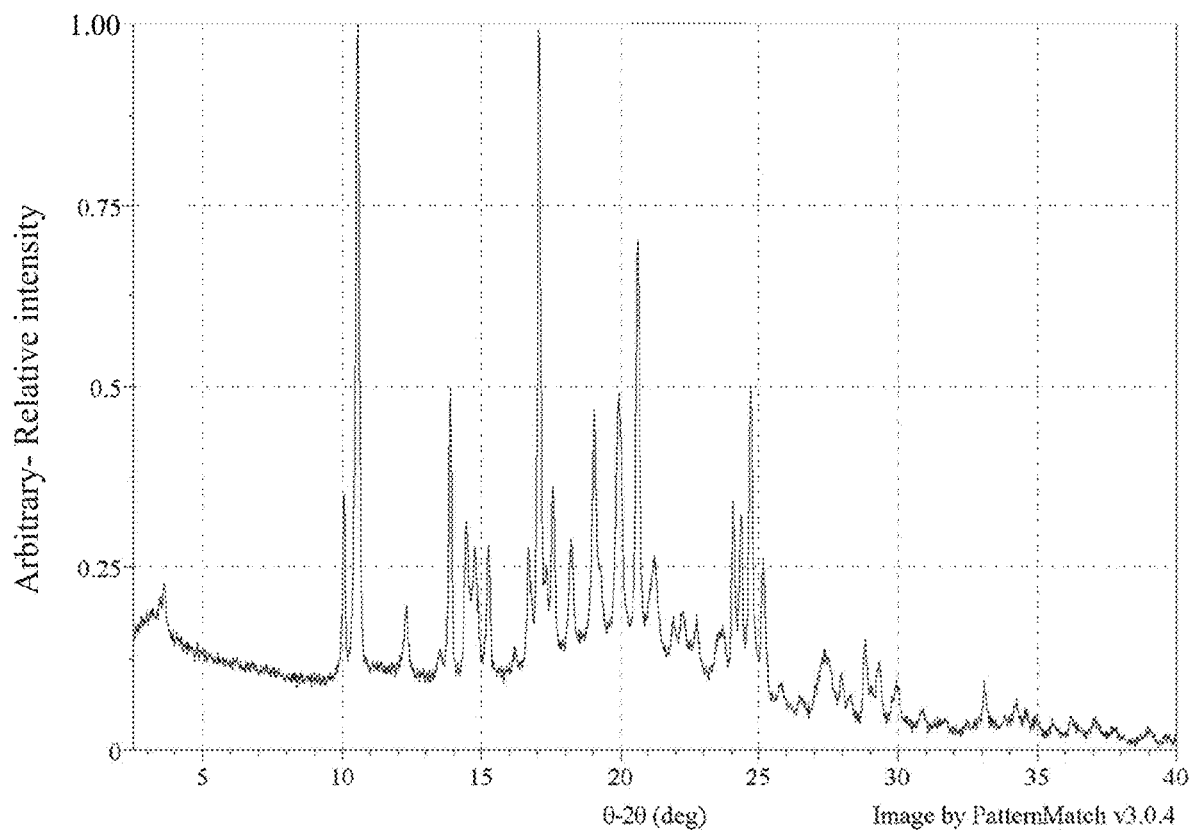
FIG. 33. XRPD pattern of Material G, sample 8235-100-02.

Material G: Alpha-1062 Gluconate, Samples 8235-87-01 and 8235-100-02 (Table 15). Material G has been observed from evaporative experiments of both 1,4-dioxane and THF. The material was waxy upon isolation but contained fine aciculars dispersed throughout.
  XRPD (FIG. 33) of sample 8235-100-02 shows much amorphous character due to its waxy nature. A reanalysis of 8235-87-01 after five weeks indicated the sample has partially converted to Form B (evidence of a minor amount of Form B was present in the initial pattern). Based on the spontaneous conversion, Material G is metastable with Form B at that condition. Material G was not observed during any of the water activity slurries or relative humidity work.

Figure 34:
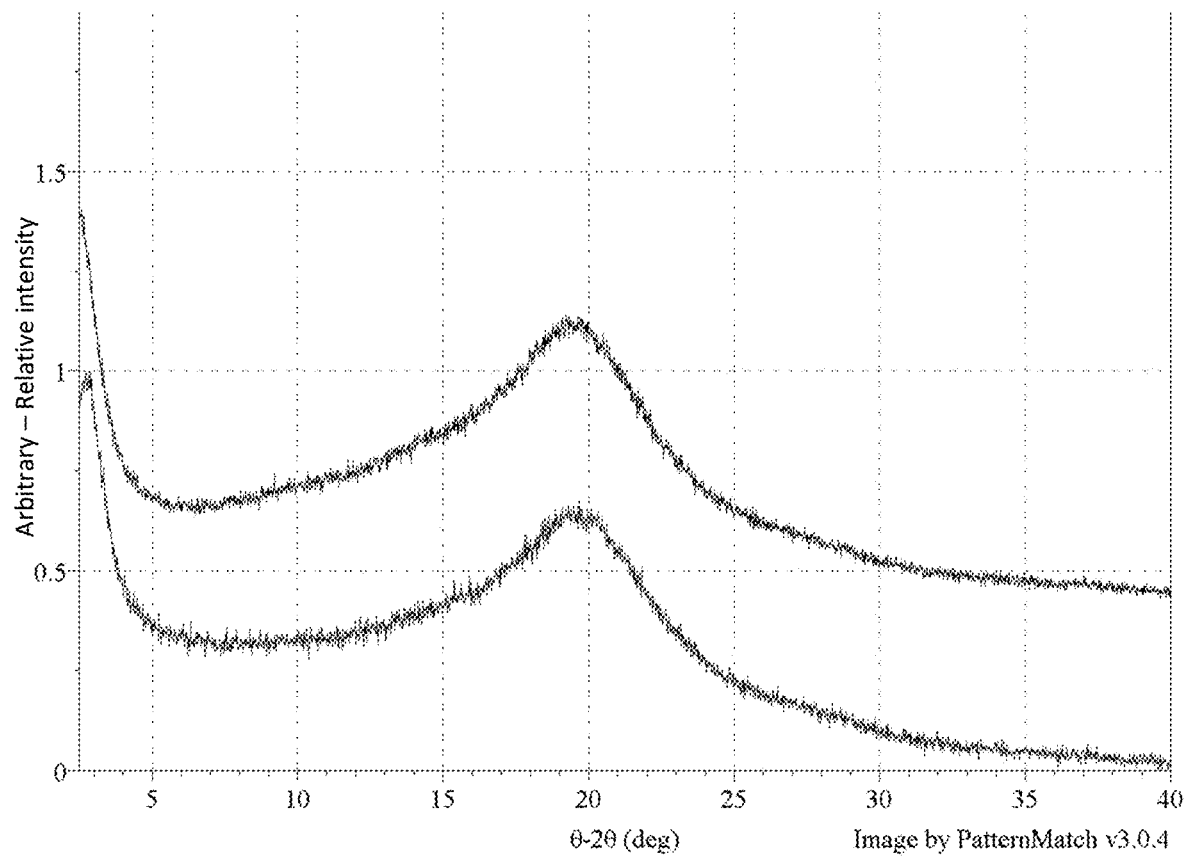
FIG. 34. XRPD pattern of amorphous Alpha-1062 Gluconate, sample 8235-92-10.
Figure 35:
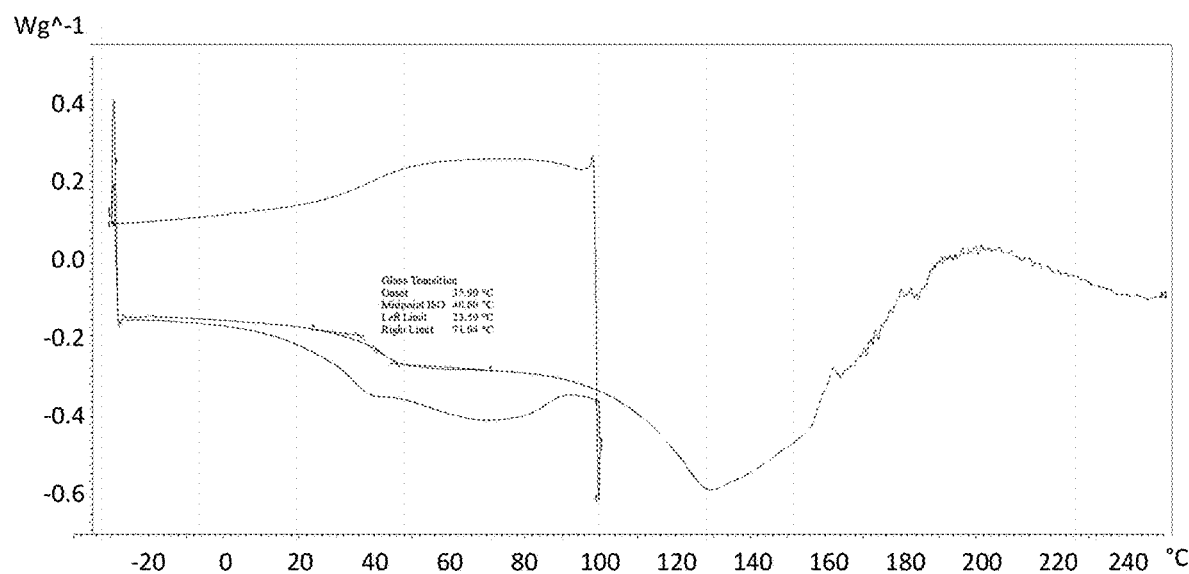
FIG. 35. Cyclic DSC of amorphous Alpha-1062 Gluconate, sample 8235-92-10.

Amorphous: Alpha-1062 Gluconate, sample 8235-76-13 (Table 16) has been observed from slow evaporation from methanol (Table 5). During Alpha-1062 Gluconate synthesis the material does not readily crystallize from solution and must be seeded. Typically, oils and tacky films are first generated which then nucleate over time.
  Sample 8235-76-13 spontaneously crystallized to a mixture of Forms B and C after 13 days.
  XRPD (FIG. 34) of an amorphous material generated via a melt quench was observed to remain amorphous after 5 weeks. No significant impurity increases were observed by $^1$H NMR.
  Thermal Analysis (FIG. 35). A cyclic DSC was conducted to determine the glass transition ($T_g$) temperature of the amorphous solid. The glass transition temperature was determined to be near 41° C. Decomposition was observed upon continued heating with no nucleation.

TABLE 1

Study Materials (Alpha-1062 Gluconate)

| Lot No. | Storage | Quantity (g) |
|---|---|---|
| CA19-1144 | ambient | 6.0 |
| QCL-PLC-I-96 | ambient | 0.7 |
| CA19-0673 | ambient | 0.5 |

TABLE 2

Characterization for Alpha-1062 Gluconate, Lot CA19-1144

| Technique | Details | Result |
|---|---|---|
| XRPD | indexed | Form A |
| $^1$H NMR | D$_2$O | consistent with structure |
| FTIR ATR | 2455_RD-00017-002 | consistent with structure |
| TGA | ambient to 350° C. | 0.17% wt. loss up to 121° C. |
| DSC | −30 to 250° C. | endotherm with onset of 117° C. |
| DSC | 120-125° C. @ 1°/min | amorphous glass upon cooling (8235-92-10) brittle, off white, NB |
| DVS | 5 to 95 to 5% RH | 0.57% wt. gain from 5 to 75% RH |
| | | 2.96% wt. gain from 75 to 85% RH |
| | | 8.67% wt. gain from 85 to 95% RH |
| | | 1.73% wt. loss from 95 to 85% RH |
| | | 2.98% wt. loss from 85 to 5% RH |
| | | hysteresis observed |
| XRPD of post DVS | 8118-78-01 | Form A + B (trace) conversion occurred in instrument after run completed as sample held at 5% RH |

TABLE 3

Characterization for Alpha-1062 Gluconate Lot QCL-PLC-I-96

| Technique | Details | Result |
|---|---|---|
| XRPD | — | Form A + B + D |
| TGA | ambient to 350° C. | 3.6% wt. loss up to 121° C. |
| DSC | −30 to 250° C. | broad endotherm onset at 69° C. final endotherm onset at 119° C. |

TABLE 4

Characterization for Alpha-1062 Gluconate Lot CA19-0673

| Technique | Details | Result |
|---|---|---|
| XRPD | — | Form A |

TABLE 5

Polymorph Screen of Alpha-1062 Gluconate (using Lot CA19-1144 [Form A])

| Solvent | Method[1] | Observation[2] | Result | Sample |
|---|---|---|---|---|
| acetone | slow cool, reflux 1. ambient 2. refrigerated, 1 d 3. freezer, 7 d | 1. oiled 2. no changes 3. waxy film, NB, no singles | — | 8235-92-08 |
| | slurry, ambient, 14 d | white fines, B | C + D | 8235-76-01 |
| ACN | slurry, ambient, 14 d | white fines, B | C | 8235-76-02 |
| ACN/H$_2$O 97:03 v/v | cooling of solution source: 8235-93-02 filtrate + seed | fine blades, limited, too thin for single analysis | — | 8296-02-01 |
| DCM | 1. fast evaporation 2. scratched | 1. film, NB 2. nucleated, fines, B | E | 8235-76-04 |
| | slurry, ambient, 14 d | fines, B | F | 8235-76-07 |

TABLE 5-continued

Polymorph Screen of Alpha-1062 Gluconate (using Lot CA19-1144 [Form A])

| Solvent | Method[1] | Observation[2] | Result | Sample |
|---|---|---|---|---|
| 1,4-dioxane | 1. fast evaporation source: 8235-76-10 solution # step 3 2. scratched, left capped, 1 d | 1. waxy film with limited rosettes of fine aciculars 2. increased nucleation bulk waxy | G + B | 8235-87-01 |
| | slow cool, 53° C. 1. refrigerated, 1 d 2. freezer, hrs. 3. warmed ambient | 1. clear solution 2. froze 3. clear solution | — | 8235-76-10 |
| | solvent: anti-solvent w/Et$_2$O source: 8235-76-10 solution # step 3 filtered solids | flocculent formed deliquesced upon isolation, 36% RH | — | 8235-87-03 |
| | slurry, ambient, 14 d source: 8235-76-11 sub sampled wet | fines, B fines, B | A A | 8235-76-11 8235-100-03 |
| EtOH | 1. slow evaporation 2. scraped | 1. tacky film, limited fines 2. no nucleation | — | 8235-76-05 |
| | slow cool, reflux 1. ambient 2. refrigerated, 5d | 1. tacky film in base 2. white solids, fines aggregated | C + A minor | 8235-76-15 |
| | slurry, ambient, 14 d | white fines, B | C + A | 8235-76-06 |
| EtOAc | slurry, ambient, 14 d | white fines, B | A | 8235-76-03 |
| IPA | slow cool, 53° C. 1. ambient 2. refrigerator, 1 d 3. filtered, briefly dried under N$_2$ | 1. irregular masses, NB 2. increase in solids 3. irregular masses, fines, damp, B | C + diffuse scatter | 8235-76-08 |
| | 8235-76-08 step 1 spotted on slide | soft material, flowed | — | 8235-81-01 |
| | slurry, ambient, 14 d | fines, B | C | 8235-76-09 |
| IPA/H$_2$O 96:04 v/v | fast evaporation source: 8235-92-04 filtrate + seed (c) | limited fine aciculars, thin tacky film, bulk of materials | amorph + C | 8296-02-03 |
| IPA/H$_2$O 97:03 v/v | cooling of solution source: 8235-92-03 filtrate | film deposited, no singles, limited material | — | 8296-02-02 |
| MEK/H$_2$O 98:02 v/v 0.42 a$_w$ | 1. heat to 55° C., 5 min. 2. removed, cooled briefly 3. sonicated 4. heat to 55° C., few hrs. 5. cooled to ambient; left overnight | 1. partially dissolved 2. turbid 3. slurry 4. slurry 5. fine aciculars, B | C + B | 8235-86-02 |
| | solids wetted, left at ambient, 22 d | very fine aciculars, increased size, no singles | — | 8235-92-15 |
| MeOH | slow evaporation | film, soft, areas brittle scraped with pick | amorph | 8235-76-13[3] |
| | 1. rotary evaporation 2. vacuum dried, ambient, 1 d 3. treated with heptane sonicated 4. filtered, N$_2$ dried | 1. oil 2. tacky film, NB 3. solidified 4. opaque solids, NB | amorph + C | 8235-92-13 |
| | vapor diffusion w/Et$_2$O 1. ambient 2. refrigerated, 1 d 3. freezer, 7 d 4. slurry, ambient 34 d | 1. oil 2. oil 3. opaque, oil 4. oil | — | 8235-79-01 |
| THF | fast evaporation source: 8235-76-14 filtrate | oily/waxy residue, fines and limited wispy rosettes, B, mixed | G | 8235-100-02 |
| | slurry, ambient, 14 d | fines, B | A | 8235-76-14 |
| THF/H$_2$O 95:05 v/v 0.76 a$_w$ | cooling of solution refrigerated, 1 d | white fines, B | B | 8235-92-05 |
| water | 1. fast evaporation 2. mixed with pick 3. left at ambient | 1. film, zone of aciculars, B 2. tacky, no nucleation 3. nucleated | C + B | 8235-76-12 |
| | solvent: anti-solvent 1. added to ACN 2. ambient, 1 d | 1. white flocculent then clumped/dissolved 2. oil droplets in base | amorph | 8235-92-09 |

TABLE 5-continued

Polymorph Screen of Alpha-1062 Gluconate (using Lot CA19-1144 [Form A])

| Solvent | Method[1] | Observation[2] | Result | Sample |
|---|---|---|---|---|
| | 3. refrigerated, 1 d | 3. no changes | | |
| | 4. freezer, 7 d | 4. off white solids, tacky film, NB | | |
| | solvent: anti-solvent | 1. seed remained | C | 8235-92-11 |
| | 1. ACN seeded with 8235-87-02 (C) | 2. turbid, seed retained | | |
| | 2. water/API added | 3. opaque white, NB | | |
| | 3. slurry, ambient, 4 d | | | |

[1]Times and temperatures are approximate unless noted.
[2]B-birefringent and NB = non birefringent when material viewed using polarized light microscopy.
[3]Solutions treated with activated charcoal prior to evaporation. Yellow hue removed or reduced upon treatment.

TABLE 6

Water Activity for Slurries of Alpha-1062 Gluconate

| Solvent | Source | Temp | Time | Result | Sample |
|---|---|---|---|---|---|
| ACN/H$_2$O 88:12 v/v; 0.90 a$_w$ | 8296-34-01: Form B 8296-34-02: Form C 8296-34-03: Form D | ambient | 13 d | B | 8296-39-07 |
| THF/H$_2$O 95:05 v/v; 0.76 a$_w$ | lot CA19-1144: Form A | ambient | 1 d | B | 8235-92-06 |
| | 8296-34-01: Form B 8296-34-02: Form C 8296-34-03: Form D | ambient | 13 d | B | 8296-39-06 |
| MEK/H$_2$O 93:07 v/v; 0.71 a$_w$ | lot CA19-1144: Form A | ambient | 7 d | B | 8235-82-06[1] |
| | | | 1 d | B | 8235-85-01 |
| MEK/H$_2$O 95:05 v/v; 0.64 a$_w$ | lot CA19-1144: Form A | ambient | 7 d | B | 8235-82-07 |
| | | | 2 d | B | 8296-34-01 |
| | | | 1 d | B | 8235-85-02 |
| | 8296-34-01: Form B 8296-34-02: Form C 8296-34-03: Form D | ambient | 13 d | B | 8296-39-05 |
| MEK/H$_2$O 97:03 v/v; 0.52 a$_w$ | lot CA19-1144: Form A | ambient | 2 d | B | 8235-82-08 |
| | | | 1 d | B | 8235-85-03 |
| | 8235-82-03: Forms B + D | ambient | 7 d | B + C | 8296-09-03 |
| | 8296-34-01: Form B 8296-34-02: Form C 8296-34-03: Form D | ambient | 13 d | B | 8296-39-04 |
| ACN/H$_2$O 97:03 v/v; 0.50 a$_w$ | lot CA19-1144: Form A | ambient | 7 d | C | 8235-93-02 |
| | | | 7 d | C | 8296-09-01 |
| MEK/H$_2$O 98:02 v/v; 0.42 a$_w$ | lot CA19-1144: Form A | ambient | 2 d | C + B | 8235-82-09 |
| | | | 1 d | C + B | 8235-85-04 |
| | 8235-94-02: Form B | ambient | 7 d | B | 8296-09-02 |
| | 8296-34-01: Form B 8296-34-02: Form C 8296-34-03: Form D | ambient | 13 d | C + B | 8296-39-03 |
| IPA/H$_2$O 96:04 v/v; 0.38 a$_w$ | lot CA19-1144: Form A | ambient | 7 d | C | 8235-92-04 |
| IPA/H$_2$O 97:03 v/v; 0.31 a$_w$ | lot CA19-1144: Form A | ambient | 7 d | C | 8235-92-03 |
| | | | 2 d | C | 8235-34-02 |
| | 8235-34-02 sub sample | ambient | 1 d | C | 8235-34-04 |
| | 8235-82-03: Forms B + D | ambient | 7 d | B | 8296-09-04 |
| | 8296-34-01: Form B 8296-34-02: Form C 8296-34-03: Form D | ambient | 13 d | C + B | 8296-39-02 |
| MEK/H$_2$O 99:01 v/v; 0.27 a$_w$ | lot CA19-1144: Form A | ambient | 7 d | C + A | 8235-82-10 |
| | | | 1 d | A | 8235-85-05 |
| | 8235-82-10: Forms C + A | ambient | 3 d | C | 8296-07-01 |
| IPA/H$_2$O 99:01 v/v; 0.12 a$_w$ | 8296-34-01: Form B 8296-34-02: Form C 8296-34-03: Form D | ambient | 13 d | C + minor B | 8296-39-01 |
| MEK ~0 a$_w$ | lot CA19-1144: Form A | ambient | 7 d | A | 8235-92-14 |
| | | | 1 d | A | 8235-85-06 |

[1]Sample observed to dissolve to partially dissolve with oiling, nucleated with stirring.

TABLE 7

Relative Humidity Stressing of Alpha-1062 Gluconate Samples

| Source | Condition | Result | Sample |
|---|---|---|---|
| Form A lot CA19-1144 | 75% RH, 1 d | D + minor A | 8235-86-01 8235-92-12 |
| | 75% RH, 2 d | D + minor B | 8235-34-03 |
| | 43% RH, 5 d | A | 8235-92-07 |
| Form B 8235-82-08 | 0% RH, P$_2$O$_5$, 1 d | A | 8235-94-01 |
| | 43% RH, 5 d | B | 8235-94-02 |
| Form B 8296-34-01 | 57% RH, 4 d | B | 8296-41-01 |
| Form C 8235-92-04 | 43% RH, 7 d | C | 8296-08-02 |
| | 11% RH, 7 d | C | 8296-08-01 |
| Form C 8296-34-02 | 11% RH, 4 d | C | 8296-41-02 |
| Form C 8235-93-02 | 0% RH, P$_2$O$_5$, 1 d | C + minor A | 8296-03-01 |
| Form C + B 8235-82-09 | 0% RH, P$_2$O$_5$, 1 d | C + A | 8235-97-01 |
| Form D + A 8235-86-01 | 75% RH, 1 d | D + minor A | 8235-93-01 |
| Form D + A 8235-93-01 | 75% RH, 4 d | B + D | 8235-98-01 |
| Form D + A 8235-92-12 | 75% RH, 1 d | D + B | 8296-03-03 |
| Form D + B 8235-34-03 | 75% RH, 1 d | D + B | 8296-43-01 |

TABLE 8

Overlay of XRPD Prominent Peaks of Alpha-1062 Gluconate, Forms A, B, C & D

| Exemplary Prominent Two Theta (2 theta) | | | | Peak positions for found Crystalline Forms | | | |
|---|---|---|---|---|---|---|---|
| Form A | Form B | Form C | Form D | Form A | Form B | Form C | Form D |
| 3.61 | | | | | | 16.08 | |
| | | | 3.76 | | 16.45 | 16.46 | 16.27 |
| | | 3.90 | | | | | 16.70 |
| | | 9.74 | | 17.02 | | | |
| | | | 10.16 | | 17.17 | | 17.24 |
| | | 10.35 | | 17.31 | | 17.43 | |
| | 10.69 | 10.65 | | 17.79 | | | |
| 10.98 | | | | | | | 17.96 |
| | 12.92 | | | 18.44 | | | |
| | | | | | | | 18.86 |
| | 13.26 | 13.35 | 13.35 | 19.24 | | | |
| 13.80 | | | 13.75 | | 19.77 | | 19.87 |
| 14.41 | | | | 20.18 | | | 20.15 |
| 14.56 | 14.56 | | | | | | |
| | | | 14.77 | 20.91 | 21.00 | | |
| 15.08 | 15.01 | | | 21.22 | | | 21.21 |
| 15.20 | | | | | | 21.43 | |
| | | 15.66 | | 22.40 | | 22.32 | |

TABLE 9

Approximate Ambient Solubility of Form A: Alpha-1062 Gluconate, Lot CA19-1144

| Solvent | Solubility (mg/mL) | Sample |
|---|---|---|
| acetone | <3 | 8235-76-01 |
| ACN (acetonitrile) | <3 | 8235-76-02 |
| DCM (dichloromethane) | <3 | 8235-76-04 |
| 1,4-dioxane | <3 | 8235-76-10 |
| EtOH (ethanol) | 3 | 8235-76-05 |
| EtOAc (ethyl acetate) | <2 | 8235-76-03 |
| IPA (isopropanol) | <2 | 8235-76-08 |

TABLE 9-continued

Approximate Ambient Solubility of Form A: Alpha-1062 Gluconate, Lot CA19-1144

| Solvent | Solubility (mg/mL) | Sample |
|---|---|---|
| MeOH (methanol) | 37 | 8235-76-13 |
| MEK (methyl ethyl ketone) | <4 | 8235-92-14 |
| THF (tetrahydrofuran) | <3 | 8235-76-14 |
| water | >123 | 8235-76-12 |

TABLE 10

Characterization for Form B: Alpha-1062 Gluconate

| Technique | Details | Result | Sample |
|---|---|---|---|
| XRPD | — | Form B | 8235-82-08 |
| | indexed | | 8235-85-01 |
| | held @ 57% RH; 4 d | | 8296-41-01 |
| $^1$H NMR | $D_2O$ | consistent with structure | 8235-82-08 |
| FTIR | ATR | consistent with structure | 8296-41-01 |
| TGA | ambient - 350° C. | 3.3% wt. loss up to 113° C. + 5.2% wt. loss up to 147° C. | 8235-82-08 |
| DSC | −30 to 250° C. | broad endotherm onset of 66° C. followed by endotherm with onset of 115° C., weak endotherm with peak max of 152° C. | 8235-82-08 |
| DSC on 8235-82-07 | 40-75° C., 10 min; Analyzed by XRPD | Form D + C + peak | 8235-94-03 |
| DVS | 50-95-5% RH | 1.5% wt. gain from 50-95% RH 1.8% wt. loss from 95-15% RH 6.8% wet loss from 15-5% RH | 8235-82-08 |
| | post DVS sample; Analyzed by XRPD | Form A | 8118-83-01 |
| coulometric KF | held @ 57% RH; 4 d | 10.2% water content | 8296-41-01 |

TABLE 11

Characterization for Form C: Alpha-106 Gluconate

| Technique | Details | Result | Sample |
|---|---|---|---|
| XRPD | indexed | Form C | 8235-87-02 |
| | held @ 11% RH; 4 d | | 8296-41-02 |
| | held @ 11% RH; 7 d | | 8296-08-01 |
| FTIR | ATR | consistent with structure | 2455_RD-00049-01 |
| TGA | ambient - 350° C. | 0.9% wt. loss up to 121° C. | 8235-87-02 |
| DSC | −30 to 250° C. | broad endotherm, onset of 119° C. | 8235-87-02 |
| DSC | held @ 11% RH; 7 d | endotherm, onset of 129° C. | 8296-08-01 |
| XRPD | — | Form C | 8235-92-11 |
| DVS | 5-95-5% RH | 0% wt. gain from 5-65% RH | 8235-92-11 |
| | | 4.6% wt. gain from 75-95% RH | |
| | | 1.5% wt. loss from 95-75% RH | |
| | | ~3% wt. retained from 75-5% RH | |
| | | hysteresis observed | |
| | post DVS sample; Analyzed by XRPD | Form C + B | 8118-85-01 |
| coulometric KF | held @ 11% RH; 4 d | 1.3% water content | 8296-41-02 |
| XRPD | vacuum; 45° C.; 3hrs | C + minor A | 8296-03-02 |

TABLE 12

Characterization for Form D: Alpha-1062 Gluconate

| Technique | Details | Result | Sample |
|---|---|---|---|
| XRPD | indexed | Form D + minor A | 8235-86-01 |
| FTIR | ATR | consistent with structure | 8235-86-01 |
| XRPD | held @ 75% RH; 1 d | Form D + minor B | 8296-43-01 |
| coulometric KF | held @ 75% RH; 1 d | 4.3% water content | 8296-43-01 |

TABLE 13

Characterization for Material E

| Technique | Details | Result |
|---|---|---|
| XRPD | indexed | Material E indexing volume consistent with free form volume and not the salt |
| ¹H NMR | D₂O | non stoichiometric amount of gluconic acid present (evaporative experiment), two species present, and 0.6 mol/mol DCM |
| TGA | ambient - 350° C. | 1.5% weight loss up to 101° C. |
| DSC | −30 to 250° C. | broad endotherm with peak max at 53° C. endotherm with peak max at 108° C. series of weak events above 120° C. |

TABLE 14

Characterization for Material F

| Technique | Details | Result |
|---|---|---|
| XRPD | indexed | Material F indexing volume less than that of the API, likely a simple gluconate salt (Na, Ca, etc.) |

TABLE 15

Characterization for Material G

| Technique | Details | Result | Sample |
|---|---|---|---|
| XRPD | — | Material G | 8235-100-02 |
| | reanalyzed, 5 weeks | Material G + Form B | 8235-87-01 |

TABLE 16

Characterization for amorphous Alpha-1062 Gluconate

| Technique | Details | Result | Sample |
|---|---|---|---|
| XRPD | — | amorphous | 8235-76-13 |
| | reanalyzed, 13 days | Form B + C | 8235-76-13 |
| | melt generated | amorphous | 8235-92-10 |
| | reanalyzed, 5 weeks | amorphous | 8235-92-10 |
| ¹H NMR | D₂O | consistent with structure, no significant increase in impurities | 8235-92-10 |
| DSC | cyclic | glass transition: 41° C. no crystallization upon further heating | 8235-92-10 |

Re-Processing Alpha-1062 Gluconate:

Alpha-1062 gluconate (CA19-0673) was re-processed and assessed to determine if multiple, potentially insoluble, polymorph or pseudopolymorph forms could be produced.

Experiment 1

The Alpha-1062 gluconate (CA19-0673) was re-slurried in MEK/H2O at 5.6 g of Alpha-1062 gluconate was used in 19.3 g MEK+1.9 g H2O. The slurry was stirred for 30 min before washing of the filter cake with 4.1 g MEK, re-filtration and drying.

The reaction mixture was yellow to orange. The suspension was initially relatively thin, then became thicker upon longer stirring. After 30 min a very thick paste-like suspension was obtained that was difficult to stir and transfer to filter. The suspension was deemed too thick and therefore unsuitable for production. The isolated material was slightly yellowish (white to pale yellow).

Experiment 2

The Alpha-1062 gluconate (CA19-0673) was re-slurried in MEK/H2O at 5.6 g of Alpha-1062 gluconate was used in 38.6 g MEK+3.8 g H2O. The slurry was stirred for 30 min before washing of the filter cake with 8.2 g MEK, re-filtration and drying. The reaction mixture was yellow to orange. The suspension was initially relatively thin, then became thicker upon longer stirring. After 30 min a suspension was obtained that was notably less thick than in experiment 1 and was able to be easily stirred and transferred to filter. The material was washed in MEK and dried in a rotator at 30° C./20 mbar for approx. 2 hours.

The isolated material was comparable in color to batch CA19-0673. The relative retention time (RRT) in HPLC was consistent with earlier measurements and a recovery of approx. 90% was obtained. Powder X-Ray diffraction spectra were obtained by measuring the dried product. The pattern revealed a mixture of multiple Forms, including Form A and one or more of Forms B-D, likely a mixture of Forms A, B and C.

Experiment 3

The Alpha-1062 gluconate (CA19-0673) was re-slurried in MEK at 20° C., without water. 5.6 g of Alpha-1062 gluconate was used in 38.6 g MEK. The slurry was stirred for 30 min before drying.

The reaction mixture was lighter than the previous experiments, a light yellow. The suspension was of consistent viscosity upon stirring. After 30 min a suspension was obtained that was notably less thick than in experiment 1 and was able to be easily stirred and transferred to filter. The material was dried in a rotator at 30° C./20 mbar for approx. 2 hours.

Figure 8:
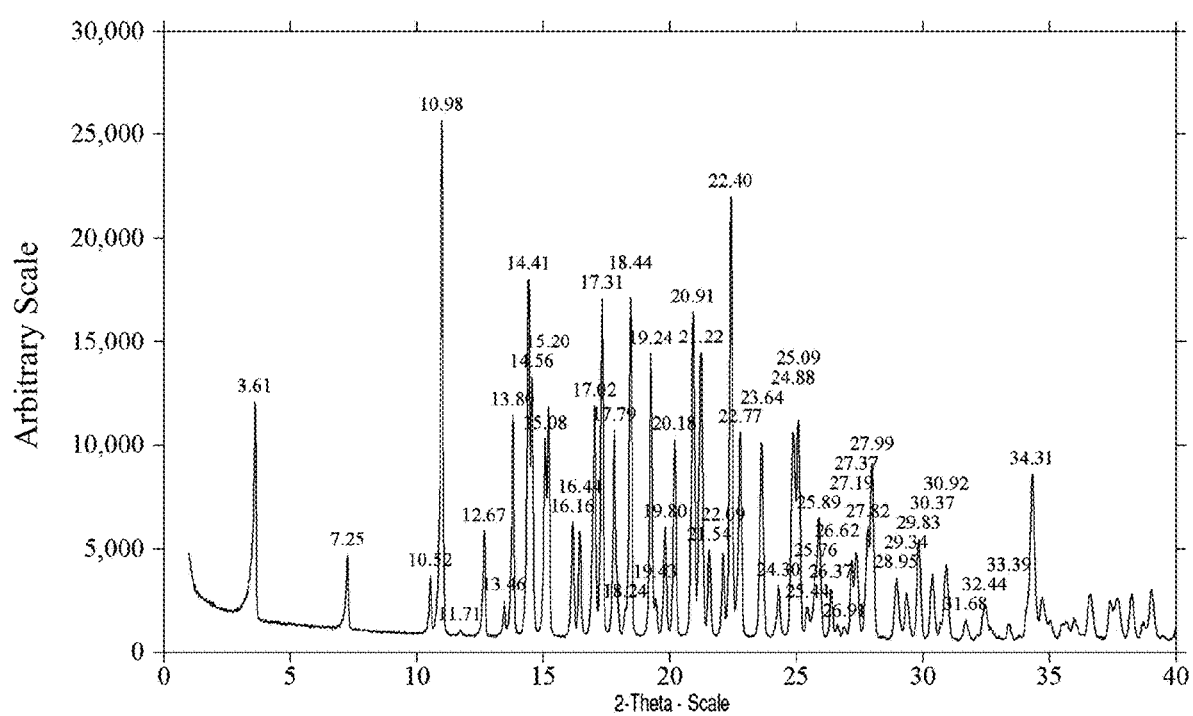
FIG. 8. Observed XRPD peaks of Form A: Alpha-1062 Gluconate, lot CA19-1144.
Figure 9:
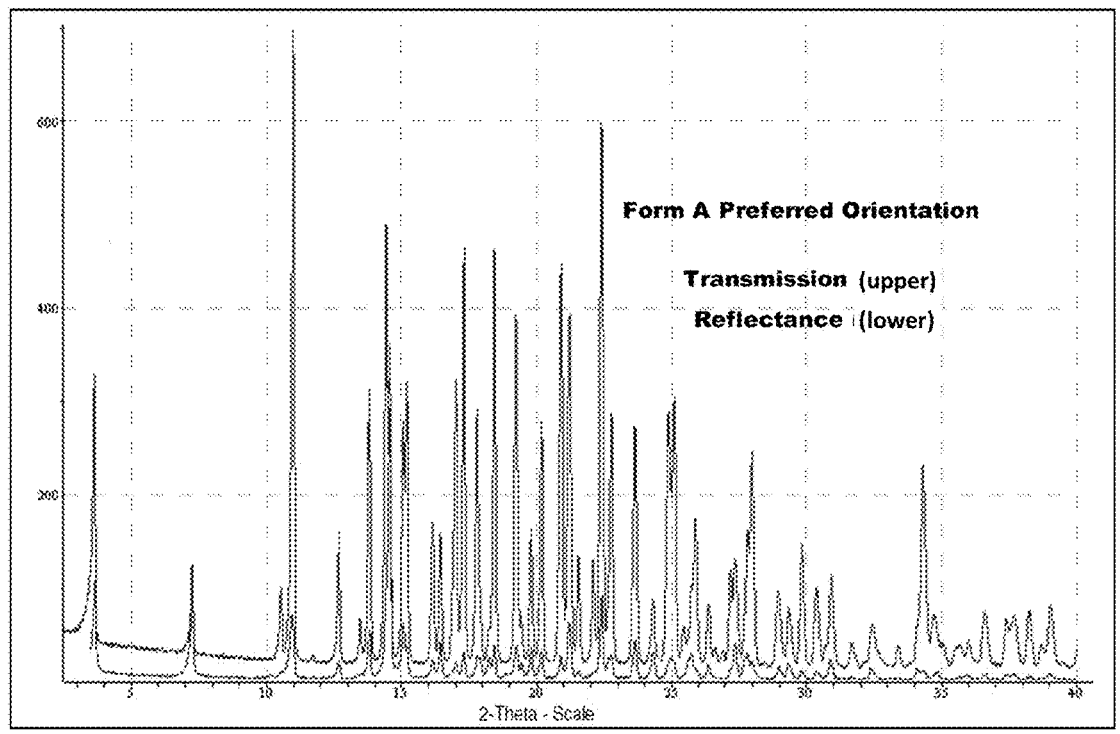
FIG. 9. Overlay of Transmission and Reflectance XRPD patterns of Form A.

The isolated material was comparable in color to batch CA19-0673. The relative retention time (RRT) in HPLC was consistent with earlier measurements and a recovery of approx. 95% was obtained. Powder X-Ray diffraction spectra were obtained by measuring the dried product. The pattern corresponded to Form A, as shown in FIG. 8.

Synthesis of Alpha-1062 Gluconate:

The gluconate salt of Alpha-1062 was created according to the following previously established general scheme:

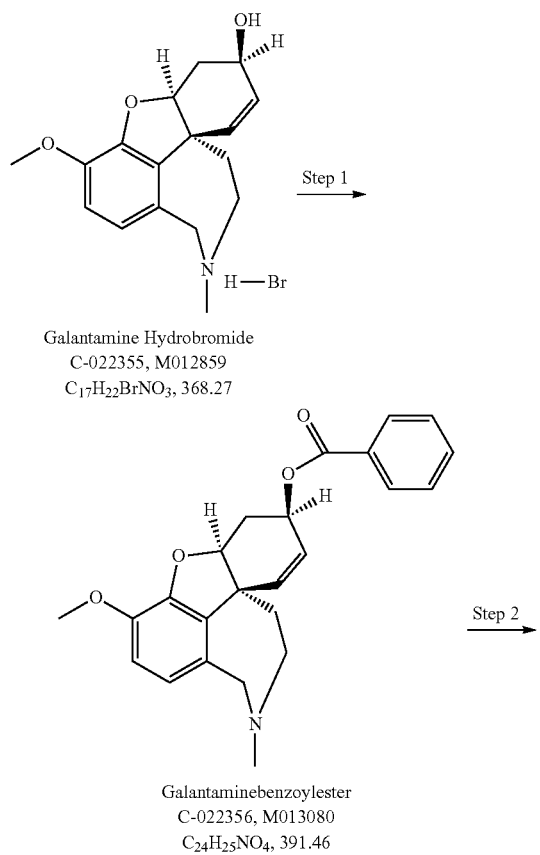

Galantamine Hydrobromide
C-022355, M012859
$C_{17}H_{22}BrNO_3$, 368.27

Galantaminebenzoylester
C-022356, M013080
$C_{24}H_{25}NO_4$, 391.46

-continued

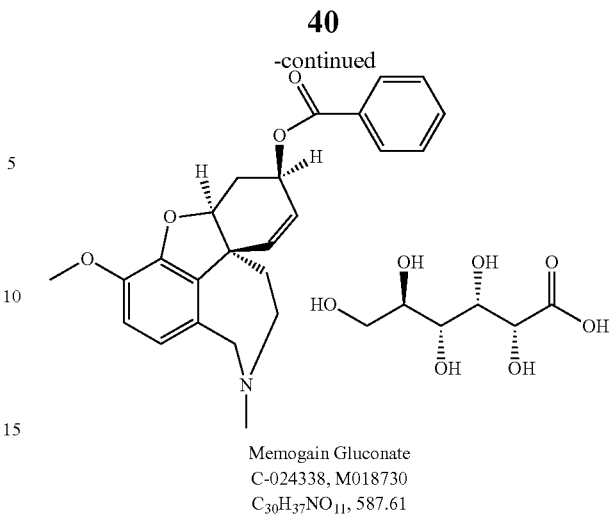

Memogain Gluconate
C-024338, M018730
$C_{30}H_{37}NO_{11}$, 587.61

What is claimed is:

1. A crystalline solid form of Alpha-1062 gluconate (Form C), wherein said crystalline form has prominent peaks at 3.90, 9.74, 10.35 and 21.43 degrees 2-theta (±0.2) in a powder X-ray diffraction pattern.

2. The crystalline solid form according to claim 1, wherein said crystalline form has one or more additional prominent peaks at 15.66 and/or 23.90 degrees 2-theta (±0.2) in a powder X-ray diffraction pattern.

3. The crystalline solid form according to claim 1, wherein said crystalline form further has at least another prominent peak selected from the group consisting of 10.65, 13.35, 15.01, 15.66, 16.08, 16.46, 17.43, 19.77 and 22.32 degrees 2-theta (±0.2) in a powder X-ray diffraction pattern.

4. The crystalline solid form according to claim 1, wherein said crystalline form further has prominent peaks at 13.35, 15.01, 16.08 and 16.46 degrees 2-theta (±0.2).

5. The crystalline solid form according to claim 4, wherein the prominent peaks at 10.35, 13.35, 15.01, 16.08 and 16.46 degrees 2-theta (±0.2) are the five peaks with the highest relative intensity in a powder X-ray diffraction pattern obtained using analysis in transmission mode.

6. The crystalline solid form according to claim 1, wherein said crystalline form further has a peak at 7.85 degrees 2-theta (±0.2).

7. The crystalline solid form according to claim 1, wherein said crystalline form exhibits an onset of melting at a temperature of 115-125° C. when assessed using differential scanning calorimetry (DSC).

8. The crystalline solid form according to claim 7, wherein said crystalline form exhibits an onset of melting at a temperature of 119° C.

9. The crystalline solid form according to claim 1, wherein said crystalline form exhibits a weight loss of 0.5-1.5% when assessed using Thermo-Gravimetric Analysis (TGA).

10. The crystalline solid form according to claim 9, wherein said crystalline form exhibits a weight loss of 0.9%.

11. A pharmaceutical composition in solid form comprising the crystalline solid form according to claim 1 (Form C), wherein said composition additionally comprises one or more pharmaceutically acceptable excipients.

12. The pharmaceutical composition according to claim 11, wherein the composition is suitable for oral or transmucosal administration.

13. A method of treating Alzheimer's disease in a subject in need thereof, comprising administering an effective amount of a pharmaceutical composition comprising the crystalline solid form of Alpha-1062 gluconate (Form C) according to claim 1 and one or more pharmaceutically acceptable excipients to the subject.

* * * * *

UNITED STATES PATENT AND TRADEMARK OFFICE
CERTIFICATE OF CORRECTION

PATENT NO. : 12,157,743 B2
APPLICATION NO. : 18/463157
DATED : December 3, 2024
INVENTOR(S) : Fred D. Sancilio Page 1 of 1

It is certified that error appears in the above-identified patent and that said Letters Patent is hereby corrected as shown below:

In the Specification

In Column 2, Line 21, delete "a carboxyesterase, resulting" and insert --a carboxylesterase, resulting--.

In Column 3, Line 20, delete "Scanning calorimetry [DSC]" and insert --Scanning Calorimetry [DSC]--.

In Column 4, Line 51, delete "need be detected" and insert --need to be detected--.

In Column 7, Line 53, delete "need be detected" and insert --need to be detected--.

In Column 7, Line 63, delete "on XRPD" and insert --on XRPD comparisons.--.

In Column 8, Line 1, delete "and/or degrees 2-theta" and insert --and/or 15.46 degrees 2-theta--.

In Column 9, Line 46, delete "need be detected" and insert --need to be detected--.

In Column 11, Line 12, delete "need be detected" and insert --need to be detected--.

In Column 13, Line 27, delete "examples below" and insert --examples below.--.

In Column 16, Line 5, delete "intranasally, bucally or" and insert --intranasally, buccally or--.

In Column 19, Line 60, delete "Scanning calorimetry) is" and insert --Scanning Calorimetry) is--.

In Column 38, Line 46, delete "MEK/H2O at 5.6 g" and insert --MEK/$H_2$O at 20° C. 5.6 g--.

In Column 38, Line 61, delete "MEK/H2O at 5.6 g" and insert --MEK/$H_2$O at 20° C. 5.6 g--.

Signed and Sealed this
Fourth Day of March, 2025

Coke Morgan Stewart
*Acting Director of the United States Patent and Trademark Office*